(12) United States Patent
Voegele et al.

(10) Patent No.: US 11,000,707 B2
(45) Date of Patent: May 11, 2021

(54) ULTRASONIC SURGICAL INSTRUMENTS

(71) Applicant: Ethicon LLC, Guaynabo, PR (US)

(72) Inventors: Aaron C. Voegele, Loveland, OH (US); Scott A. Nield, Morrow, OH (US); Shan Wan, Plymouth, MN (US)

(73) Assignee: Ethicon LLC, Guaynabo, PR (US)

( * ) Notice: Subject to any disclaimer, the term of this patent is extended or adjusted under 35 U.S.C. 154(b) by 0 days.

(21) Appl. No.: 16/552,700

(22) Filed: Aug. 27, 2019

(65) Prior Publication Data
US 2019/0381339 A1 Dec. 19, 2019

Related U.S. Application Data

(63) Continuation of application No. 15/352,145, filed on Nov. 15, 2016, now Pat. No. 10,512,795, which is a (Continued)

(51) Int. Cl.
*H01L 41/09* (2006.01)
*A61N 7/02* (2006.01)
(Continued)

(52) U.S. Cl.
CPC ............. *A61N 7/02* (2013.01); *A61B 8/4209* (2013.01); *A61B 8/4494* (2013.01); *A61B 17/320068* (2013.01); *H01L 41/0906* (2013.01); *A61B 2017/0023* (2013.01); *A61B 2017/00402* (2013.01); *A61B 2017/320069* (2017.08); *A61B 2017/320071* (2017.08); *A61B 2017/320072* (2013.01); *A61B 2017/320078* (2017.08);
(Continued)

(58) Field of Classification Search
CPC ......... H01L 41/0906; A61B 17/320068; A61B 8/4209; A61B 8/4494; A61N 7/02
See application file for complete search history.

(56) References Cited

U.S. PATENT DOCUMENTS 4,057,660 A 11/1977 Yoshida et al.
4,169,984 A 10/1979 Parisi
(Continued)

FOREIGN PATENT DOCUMENTS

CA 837241 A 3/1970
CN 106077718 A 11/2016
(Continued)

OTHER PUBLICATIONS

Emam, Tarek A. et al., "How Safe is High-Power Ultrasonic Dissection?," Annals of Surgery, (2003), pp. 186-191, vol. 237, No. 2, Lippincott Williams & Wilkins, Inc., Philadelphia, PA.
(Continued)

*Primary Examiner* — J. San Martin

(57) ABSTRACT

In one general aspect, various embodiments are directed to an ultrasonic surgical instrument that comprises a transducer configured to produce vibrations along a longitudinal axis at a predetermined frequency. In various embodiments, an ultrasonic blade extends along the longitudinal axis and is coupled to the transducer. In various embodiments, the ultrasonic blade includes a body having a proximal end and a distal end, wherein the distal end is movable relative to the longitudinal axis by the vibrations produced by the transducer.

18 Claims, 36 Drawing Sheets

Related U.S. Application Data continuation of application No. 14/270,722, filed on May 6, 2014, now Pat. No. 9,498,245, which is a continuation of application No. 13/717,084, filed on Dec. 17, 2012, now Pat. No. 8,754,570, which is a continuation of application No. 12/490,906, filed on Jun. 24, 2009, now Pat. No. 6,334,635.

(51) Int. Cl.
*A61B 8/00* (2006.01)
*A61B 17/32* (2006.01)
*A61B 17/00* (2006.01)
*A61B 18/00* (2006.01)

(52) U.S. Cl.
CPC ............ *A61B 2017/320088* (2013.01); *A61B 2017/320089* (2017.08); *A61B 2018/00607* (2013.01); *Y10T 29/42* (2015.01); *Y10T 29/49005* (2015.01); *Y10T 29/49155* (2015.01)

(56) References Cited

U.S. PATENT DOCUMENTS

| | | |
|---|---|---|
| 4,352,459 A | 10/1982 | Berger et al. |
| 4,452,473 A | 6/1984 | Ruschke |
| 4,696,667 A | 9/1987 | Masch |
| 4,783,997 A | 11/1988 | Lynnworth |
| 4,978,067 A | 12/1990 | Berger et al. |
| 5,047,043 A | 9/1991 | Kubota et al. |
| 5,057,119 A | 10/1991 | Clark et al. |
| 5,058,570 A | 10/1991 | Idemoto et al. |
| 5,059,210 A | 10/1991 | Clark et al. |
| 5,096,532 A | 3/1992 | Neuwirth et al. |
| 5,156,613 A | 10/1992 | Sawyer |
| 5,159,226 A | 10/1992 | Montgomery |
| 5,209,776 A | 5/1993 | Bass et al. |
| 5,242,385 A | 9/1993 | Strukel |
| 5,289,436 A | 2/1994 | Terhune |
| 5,306,280 A | 4/1994 | Bregen et al. |
| 5,312,327 A * | 5/1994 | Bales ........................ A61B 1/12 604/21 |
| 5,324,297 A | 6/1994 | Hood et al. |
| 5,342,292 A | 8/1994 | Nita et al. |
| 5,372,585 A | 12/1994 | Tiefenbrun et al. |
| 5,383,883 A | 1/1995 | Wilk et al. |
| 5,391,144 A | 2/1995 | Sakurai et al. |
| 5,397,293 A | 3/1995 | Alliger et al. |
| 5,400,267 A | 3/1995 | Denen et al. |
| 5,413,107 A | 5/1995 | Oakley et al. |
| 5,496,411 A | 3/1996 | Candy |
| 5,527,273 A | 6/1996 | Manna et al. |
| 5,575,799 A | 11/1996 | Bolanos et al. |
| 5,647,851 A | 7/1997 | Pokras |
| 5,735,875 A | 4/1998 | Bonutti et al. |
| 5,807,310 A | 9/1998 | Hood |
| 5,810,869 A | 9/1998 | Kaplan et al. |
| 5,853,290 A | 12/1998 | Winston |
| 5,879,363 A | 3/1999 | Urich |
| 5,893,880 A | 4/1999 | Egan et al. |
| 5,895,412 A | 4/1999 | Tucker |
| 5,910,150 A | 6/1999 | Saadat |
| 5,941,887 A | 8/1999 | Steen et al. |
| 6,001,120 A | 12/1999 | Levin |
| 6,053,906 A | 4/2000 | Honda et al. |
| 6,063,050 A | 5/2000 | Manna et al. |
| 6,187,003 B1 | 2/2001 | Buysse et al. |
| 6,206,877 B1 | 3/2001 | Kese et al. |
| 6,217,591 B1 | 4/2001 | Egan et al. |
| 6,270,471 B1 | 8/2001 | Hechel et al. |
| 6,409,743 B1 | 6/2002 | Fenton, Jr. |
| 6,416,525 B1 | 7/2002 | Shibata |
| 6,498,421 B1 | 12/2002 | Oh et al. |
| 6,526,976 B1 | 3/2003 | Baran |
| 6,562,059 B2 | 5/2003 | Edwards et al. |
| 6,569,109 B2 | 5/2003 | Sakurai et al. |
| 6,575,929 B2 | 6/2003 | Sussman et al. |
| 6,602,229 B2 | 8/2003 | Coss |
| 6,623,444 B2 | 9/2003 | Babaev |
| 6,648,839 B2 | 11/2003 | Manna et al. |
| 6,656,124 B2 | 12/2003 | Flesch et al. |
| 6,689,086 B1 | 2/2004 | Nita et al. |
| 6,695,782 B2 | 2/2004 | Ranucci et al. |
| 6,699,214 B2 | 3/2004 | Gellman |
| 6,702,761 B1 | 3/2004 | Damadian et al. |
| 6,712,805 B2 | 3/2004 | Weimann |
| 6,832,988 B2 | 12/2004 | Sproul |
| 6,887,221 B1 | 5/2005 | Baillargeon et al. |
| 6,908,466 B1 | 6/2005 | Bonutti et al. |
| 6,932,876 B1 | 8/2005 | Statnikov |
| 6,989,017 B2 | 1/2006 | Howell et al. |
| 7,002,283 B2 | 2/2006 | Li et al. |
| 7,018,354 B2 | 3/2006 | Tazi |
| 7,131,983 B2 | 11/2006 | Murakami |
| 7,135,029 B2 | 11/2006 | Makin et al. |
| 7,182,762 B2 | 2/2007 | Bortkiewicz |
| 7,282,836 B2 | 10/2007 | Kwon et al. |
| 7,338,463 B2 | 3/2008 | Vigil |
| 7,533,830 B1 | 5/2009 | Rose |
| 7,563,269 B2 | 7/2009 | Hashiguchi |
| 7,578,166 B2 | 8/2009 | Ethridge et al. |
| 7,686,763 B2 | 3/2010 | Vaezy et al. |
| 7,815,658 B2 | 10/2010 | Murakami |
| 7,828,808 B2 | 11/2010 | Hinman et al. |
| 7,834,521 B2 | 11/2010 | Habu et al. |
| 7,883,465 B2 | 2/2011 | Donofrio et al. |
| 7,922,716 B2 | 4/2011 | Malecki et al. |
| 8,006,358 B2 | 8/2011 | Cooke et al. |
| 8,016,843 B2 | 9/2011 | Escaf |
| 8,137,263 B2 | 3/2012 | Marescaux et al. |
| 8,394,096 B2 | 3/2013 | Moses et al. |
| 8,435,258 B2 | 5/2013 | Young et al. |
| 8,610,334 B2 | 12/2013 | Bromfield |
| 8,691,268 B2 | 4/2014 | Weimann |
| 8,870,867 B2 | 10/2014 | Walberg et al. |
| 9,023,072 B2 | 5/2015 | Young et al. |
| 9,301,772 B2 | 4/2016 | Kimball et al. |
| 9,486,235 B2 | 11/2016 | Harrington et al. |
| 9,826,976 B2 | 11/2017 | Parihar et al. |
| 10,363,058 B2 | 7/2019 | Roberson et al. |
| 10,368,894 B2 | 8/2019 | Madan et al. |
| 10,561,436 B2 | 2/2020 | Asher et al. |
| 10,677,764 B2 | 6/2020 | Ross et al. |
| 10,779,848 B2 | 9/2020 | Houser |
| 10,856,896 B2 | 12/2020 | Eichmann et al. |
| 2002/0002378 A1 | 1/2002 | Messerly |
| 2003/0120306 A1 | 6/2003 | Burbank et al. |
| 2004/0039242 A1 | 2/2004 | Tolkoff et al. |
| 2004/0147946 A1 | 7/2004 | Mastri et al. |
| 2004/0199194 A1 | 10/2004 | Witt et al. |
| 2005/0085728 A1 | 4/2005 | Fukuda |
| 2006/0030848 A1 | 2/2006 | Craig et al. |
| 2006/0257819 A1 | 11/2006 | Johnson |
| 2008/0097281 A1 | 4/2008 | Zusman et al. |
| 2008/0294051 A1 | 11/2008 | Koshigoe et al. |
| 2009/0143797 A1 * | 6/2009 | Smith ..................... A61N 7/02 606/169 |
| 2010/0042126 A1 | 2/2010 | Houser et al. |
| 2010/0228191 A1 | 9/2010 | Alvarez et al. |
| 2011/0291526 A1 | 12/2011 | Abramovich et al. |
| 2012/0078249 A1 | 3/2012 | Eichmann et al. |
| 2012/0136279 A1 | 5/2012 | Tanaka et al. |
| 2013/0231691 A1 | 9/2013 | Houser |
| 2013/0331873 A1 | 12/2013 | Ross et al. |
| 2014/0207163 A1 | 7/2014 | Eichmann et al. |
| 2016/0240768 A1 | 8/2016 | Fujii et al. |
| 2017/0027624 A1 | 2/2017 | Wilson et al. |
| 2017/0036044 A1 | 2/2017 | Ito |
| 2018/0177545 A1 | 6/2018 | Boudreaux et al. |
| 2018/0296239 A1 | 10/2018 | Houser et al. |
| 2018/0310983 A1 | 11/2018 | Worrell et al. |
| 2019/0350615 A1 | 11/2019 | Messerly et al. |
| 2019/0380733 A1 | 12/2019 | Stulen et al. |
| 2019/0381340 A1 | 12/2019 | Voegele et al. |

(56) References Cited

U.S. PATENT DOCUMENTS

| | | |
|---|---|---|
| 2020/0008857 A1 | 1/2020 | Conlon et al. |
| 2020/0015798 A1 | 1/2020 | Wiener et al. |
| 2020/0015838 A1 | 1/2020 | Robertson |
| 2020/0046401 A1 | 2/2020 | Witt et al. |
| 2020/0054386 A1 | 2/2020 | Houser et al. |
| 2020/0054899 A1 | 2/2020 | Wiener et al. |
| 2020/0085462 A1 | 3/2020 | Robertson |
| 2020/0085466 A1 | 3/2020 | Faller et al. |
| 2020/0323551 A1 | 10/2020 | Faller et al. |

FOREIGN PATENT DOCUMENTS

| | | |
|---|---|---|
| EP | 1543854 A1 | 6/2005 |
| FR | 2454351 A1 | 11/1980 |
| JP | H04161078 A | 6/1992 |
| JP | H07185457 A | 7/1995 |
| JP | H07299415 A | 11/1995 |
| JP | 2000210296 A | 8/2000 |
| JP | 2001057985 A | 3/2001 |
| JP | 2001170066 A | 6/2001 |
| JP | 2001198137 A | 7/2001 |
| JP | 2002233533 A | 8/2002 |
| JP | 2003230567 A | 8/2003 |
| JP | 3841627 B2 | 11/2006 |
| WO | WO-9805437 A1 | 2/1998 |
| WO | WO-0132087 A1 | 5/2001 |
| WO | WO-02076685 A1 | 10/2002 |

OTHER PUBLICATIONS

Feil, Wolfgang, M.D., et al., "Ultrasonic Energy for Cutting, Coagulating, and Dissecting," (2005), pp. IV, 17, 21, and 23; ISBN 3-13-127521-9 (New York, NY, Thieme, New York).

McCarus, Steven D. M.D., "Physiologic Mechanism of the Ultrasonically Activated Scalpel," the Journal of the American Association of Gynecologic Laparoscopists; (Aug. 1996), vol. 3, No. 4., pp. 601-606 and 608.

* cited by examiner

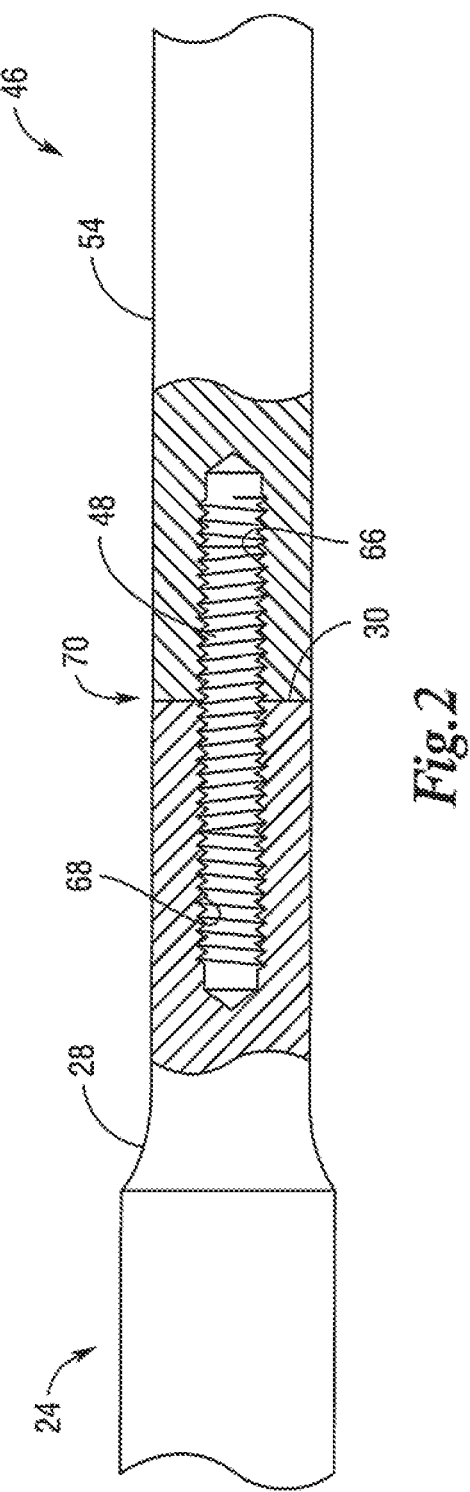

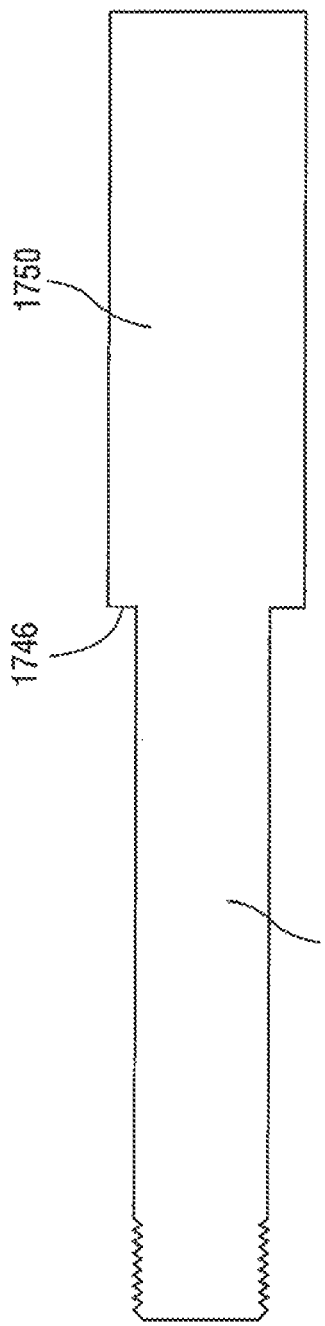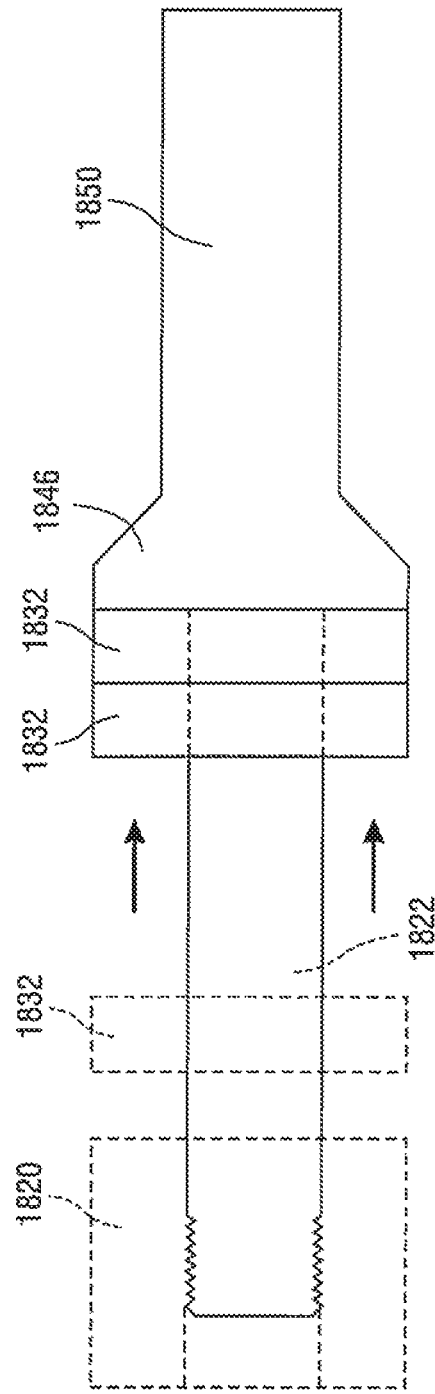

ULTRASONIC SURGICAL INSTRUMENTS

CROSS-REFERENCE TO RELATED APPLICATIONS

This application is a continuation application under 35 U.S.C. § 120 of U.S. patent application Ser. No. 15/352,145, filed on Nov. 15, 2016, entitled ULTRASONIC SURGICAL INSTRUMENTS which issued on Dec. 24, 2019 as U.S. Pat. No. 10,512,795, which is a continuation application under 35 U.S.C. § 120 of U.S. patent application Ser. No. 14/270,722, filed on May 6, 2014, entitled ULTRASONIC SURGICAL INSTRUMENTS, which issued on Nov. 22, 2016 as U.S. Pat. No. 9,498,245, which is a continuation application under 35 U.S.C. § 120 of U.S. patent application Ser. No. 13/717,084, filed on Dec. 17, 2012, entitled ULTRASONIC SURGICAL INSTRUMENTS COMPRISING TRANSDUCER ARRANGEMENTS, which issued on Jun. 17, 2014 as U.S. Pat. No. 8,754,570, which is a continuation application under 35 U.S.C. § 120 of U.S. patent application Ser. No. 12/490,906, filed on Jun. 24, 2009, entitled TRANSDUCER ARRANGEMENTS FOR ULTRASONIC SURGICAL INSTRUMENTS, which issued on Dec. 18, 2012 as U.S. Pat. No. 8,334,635, all of which are hereby incorporated by reference herein in their respective entireties.

BACKGROUND

The present invention relates, in general, to ultrasonic surgical instruments. Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end effector at ultrasonic frequencies. Ultrasonic vibrations, when transmitted to organic tissue at suitable energy levels and using a suitable end effector, may be used to cut, dissect, elevate or cauterize tissue or to separate muscle tissue from bone. Ultrasonic instruments utilizing solid core technology are particularly advantageous because of the amount of ultrasonic energy that may be transmitted from the ultrasonic transducer, through a waveguide, and to the surgical end effector. Such instruments may be used for open procedures or minimally invasive procedures, such as endoscopic or laparoscopic procedures, wherein the end effector is passed through a trocar to reach the surgical site.

Activating or exciting the end effector (e.g., cutting blade) of such instruments at ultrasonic frequencies induces longitudinal vibratory movement that generates localized heat within adjacent tissue. Because of the nature of ultrasonic instruments, a particular ultrasonically actuated end effector may be designed to perform numerous functions, including, for example, cutting and coagulation. Ultrasonic vibration is induced in the surgical end effector by electrically exciting a transducer, for example. The transducer may be constructed of one or more piezoelectric or magnetostrictive elements in the instrument hand piece. Vibrations generated by the transducer are transmitted to the surgical end effector via an ultrasonic waveguide extending from the transducer to the surgical end effector. The waveguide and end effector are designed to resonate at the same frequency as the transducer. Therefore, when an end effector is attached to a transducer, the overall system frequency is the same frequency as the transducer itself.

The amplitude of the longitudinal ultrasonic vibration at the tip, d, of the end effector behaves as a simple sinusoid at the resonant frequency as given by:

$$d = A \sin(\omega t)$$

where:
$\omega$=the radian frequency which equals a times the cyclic frequency, f; and
A=the zero-to-peak amplitude.
The longitudinal excursion of the end effector tip is defined as the peak-to-peak (p-t-p) amplitude, which is just twice the amplitude of the sine wave or 2A. Often, the end effector can comprise a blade which, owing to the longitudinal excursion, can cut and/or coagulate tissue. U.S. Pat. No. 6,283,981, which issued on Sep. 4, 2001 and is entitled METHOD OF BALANCING ASYMMETRIC ULTRASONIC SURGICAL BLADES; U.S. Pat. No. 6,309,400, which issued on Oct. 30, 2001 and is entitled CURVED ULTRASONIC BLADE HAVING A TRAPEZOIDAL CROSS SECTION; and U.S. Pat. No. 6,436,115, which issued on Aug. 20, 2002 and is entitled BALANCED ULTRASONIC BLADE INCLUDING A PLURALITY OF BALANCE ASYMMETRIES, the entire disclosures of which are hereby incorporated by reference herein, disclose various ultrasonic surgical instruments.

SUMMARY

In various embodiments, an ultrasonic surgical instrument is disclosed including a housing, an end effector including an ultrasonic blade, a waveguide extending to the ultrasonic blade, and a vibration generating system including a transducer attachable to the housing and a switch positioned on the housing. The transducer includes piezoelectric elements. The piezoelectric elements vibrate at a magnitude proportional to at least one electrical input. The vibration generating system is selectively operable from the switch in a plurality of energizing operating states and a non-energizing operating state. The plurality of energizing operating states includes a first operating state in which the transducer vibrates at a first vibration magnitude and a second operating state in which the transducer vibrates at a second vibration magnitude. The first vibration magnitude is different than the second vibration magnitude. The switch is configured to select the first operating state, the second operating state, or the non-energizing operating state.

In various embodiments, an ultrasonic surgical instrument is disclosed including a housing including a switch, an end effector including a curved ultrasonic blade, a transducer attachable to the housing, a waveguide extending from the transducer to the curved ultrasonic blade, and a vibration generating system selectively operable by the switch in a plurality of energizing operating states and a non-energizing operating state. The transducer includes piezoelectric elements. The piezoelectric elements vibrate at a magnitude proportional to at least one electrical input. The plurality of energizing operating states includes a first operating state and a second operating state. The transducer vibrates at a first vibration magnitude in the first operating state. The transducer vibrates at a second vibration magnitude in the second operating state. The first vibration magnitude is different than the second vibration magnitude. The switch is configured to select the first operating state, the second operating state, or the non-energizing operating state.

In various embodiments, an ultrasonic surgical instrument is disclosed including a housing, an end effector including an ultrasonic blade, a waveguide extending to the ultrasonic blade, and an ultrasonic energy delivery system including a transducer attachable to the housing and a switch configured to selectively operate the ultrasonic energy delivery system in a plurality of energizing operating states and a non-energizing operating state. The transducer includes piezoelectric elements. The piezoelectric elements vibrate at a magnitude proportional to at least one electrical input. The plurality of energizing operating states includes a first operating state in which the transducer vibrates at a first vibration magnitude and a second operating state in which the transducer vibrates at a second vibration magnitude. The first vibration magnitude is different than the second vibration magnitude. The switch is configured to selectively switch the ultrasonic energy delivery system between the first operating state, the second operating state, and the non-energizing operating state.

FIGURES

The features of various embodiments are set forth with particularity in the appended claims. The various embodiments, however, both as to organization and methods of operation, together with further objects and advantages thereof, may best be understood by reference to the following description, taken in conjunction with the accompanying drawings as follows.

FIG. 2 illustrates an embodiment of a connection union/joint for an ultrasonic instrument.

FIG. 33 illustrates an embodiment of an integral wave guide and end effector.

FIG. 34 illustrates an embodiment of a transducer comprising piezoelectric elements assembled directly to a wave guide.

DESCRIPTION

Figure 1:
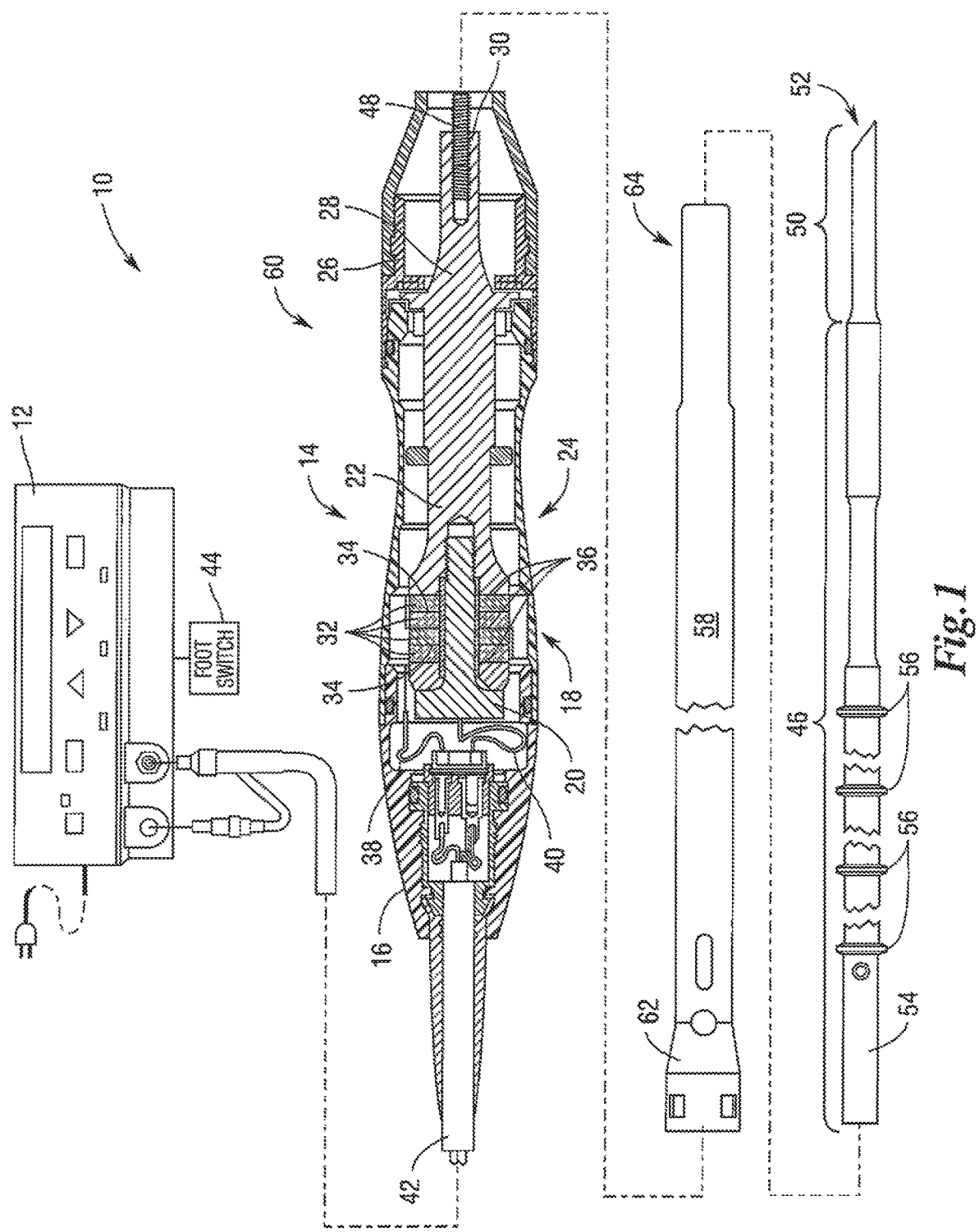
FIG. 1 illustrates an embodiment of an ultrasonic surgical instrument system.

Before explaining various embodiments in detail, it should be noted that such embodiments are not limited in their application or use to the details of construction and arrangement of parts illustrated in the accompanying drawings and description. The illustrative embodiments may be implemented or incorporated in other embodiments, variations and modifications, and may be practiced or carried out in various ways. For example, the surgical instruments disclosed below are illustrative only and not meant to limit the scope or application thereof. Furthermore, unless otherwise indicated, the terms and expressions employed herein have been chosen for the purpose of describing the illustrative embodiments for the convenience of the reader and are not to limit the scope thereof.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments is defined solely by the claims. The features illustrated or described in connection with one exemplary embodiment may be combined with the features of other embodiments. Such modifications and variations are intended to be included within the scope of the claims.

Various embodiments described herein relate, in general, to ultrasonic surgical instruments and blades for use therewith. Examples of ultrasonic surgical instruments and blades are disclosed in U.S. Pat. Nos. 5,322,055; 5,954,736; 6,309,400; 6,278,218; 6,283,981; and 6,325,811, wherein the entire disclosures of which are incorporated by reference herein. Also incorporated by reference in its entirety is commonly-owned U.S. patent application Ser. No. 11/726,625, now U.S. Pat. No. 8,911,460, entitled ULTRASONIC SURGICAL INSTRUMENTS, filed on Mar. 22, 2007. The disclosures of the following commonly-owned United States Patent Applications are incorporated herein by reference in their entirety:

(1) U.S. patent application Ser. No. 12/490,906, now U.S. Pat. No. 8,334,635, entitled TRANSDUCER ARRANGEMENTS FOR ULTRASONIC SURGICAL INSTRUMENTS, filed on Jun. 24, 2009;

(2) U.S. patent application Ser. No. 12/490,922, now U.S. Pat. No. 8,650,728, entitled ULTRASONIC SURGICAL INSTRUMENTS, filed on Jun. 24, 2009;

(3) U.S. patent application Ser. No. 12/490,933, now U.S. Pat. No. 8,344,596, entitled TRANSDUCER ARRANGEMENTS FOR ULTRASONIC SURGICAL INSTRUMENTS, filed on Jun. 24, 2009;

(4) U.S. patent application Ser. No. 12/490,948, now U.S. Pat. No. 8,319,400, entitled ULTRASONIC SURGICAL INSTRUMENTS, filed on Jun. 24, 2009; and (5) U.S. patent application Ser. No. 13/555,523, now U.S. Pat. No. 8,546,999, entitled HOUSING ARRANGEMENTS FOR ULTRASONIC SURGICAL INSTRUMENTS, filed on Jun. 23, 2012.

An ultrasonic instrument and blade according to various embodiments can be of particular benefit, among others, in orthopedic procedures where it is desirable to remove cortical bone and/or tissue while controlling bleeding. Due to its cutting and coagulation characteristics, a blade of an ultrasonic surgical instrument may be useful for general soft tissue cutting and coagulation. In certain circumstances, a blade according to various embodiments may be useful to simultaneously cut and hemostatically seal or cauterize tissue. A blade may be straight or curved, and useful for either open or laparoscopic applications. A blade according to various embodiments may be useful in spine surgery, especially to assist in posterior access in removing muscle from bone.

FIG. 1 illustrates one embodiment of an ultrasonic system 10. One embodiment of the ultrasonic system 10 comprises an ultrasonic signal generator 12 coupled to an ultrasonic transducer 14, a hand piece assembly 60 comprising a hand piece housing 16, and an end effector 50. The ultrasonic transducer 14, which is known as a "Langevin stack", generally includes a transduction portion 18, a first resonator or end-bell 20, and a second resonator or fore-bell 22, and ancillary components. In various embodiments, the ultrasonic transducer 14 is preferably an integral number of one-half system wavelengths (nλ/2) in length as will be described in more detail below. An acoustic assembly 24 can include the ultrasonic transducer 14, a mount 26, a velocity transformer 28, and a surface 30.

It will be appreciated that the terms "proximal" and "distal" are used herein with reference to a clinician gripping the hand piece assembly 60. Thus, the end effector 50 is distal with respect to the more proximal hand piece assembly 60. It will be further appreciated that, for convenience and clarity, spatial terms such as "top" and "bottom" also are used herein with respect to the clinician gripping the hand piece assembly 60. However, surgical instruments are used in many orientations and positions, and these terms are not intended to be limiting and absolute.

The distal end of the end-bell 20 is connected to the proximal end of the transduction portion 18, and the proximal end of the fore-bell 22 is connected to the distal end of the transduction portion 18. The fore-bell 22 and the end-bell 20 have a length determined by a number of variables, including the thickness of the transduction portion 18, the density and modulus of elasticity of the material used to manufacture the end-bell 20 and the fore-bell 22, and the resonant frequency of the ultrasonic transducer 14. The fore-bell 22 may be tapered inwardly from its proximal end to its distal end to amplify the ultrasonic vibration amplitude of the velocity transformer 28, or, alternately, fore-bell 22 may have no amplification.

Referring again to FIG. 1, end-bell 20 can include a threaded member extending therefrom which can be configured to be threadably engaged with a threaded aperture in fore-bell 22. In various embodiments, piezoelectric elements, such as piezoelectric elements 32, for example, can be compressed between end-bell 20 and fore-bell 22 when end-bell 20 and fore-bell 22 are assembled together. Piezoelectric elements 32 may be fabricated from any suitable material, such as, for example, lead zirconate-titanate, lead meta-niobate, lead titanate, and/or any suitable piezoelectric crystal material, for example.

In various embodiments, as discussed in greater detail below, transducer 14 can further comprise electrodes, such as positive electrodes 34 and negative electrodes 36, for example, which can be configured to create a voltage potential across one or more piezoelectric elements 32. Each of the positive electrodes 34, negative electrodes 36, and the piezoelectric elements 32 can comprise a bore extending through the center which can be configured to receive the threaded member of end-bell 20. In various embodiments, the positive and negative electrodes 34 and 36 are electrically coupled to wires 38 and 40, respectively, wherein the wires 38 and 40 can be encased within a cable 42 and electrically connectable to the ultrasonic signal generator 12 of the ultrasonic system 10.

In various embodiments, the ultrasonic transducer 14 of the acoustic assembly 24 converts the electrical signal from the ultrasonic signal generator 12 into mechanical energy that results in primarily longitudinal vibratory motion of the ultrasonic transducer 24 and the end effector 50 at ultrasonic frequencies. A suitable generator is available as model number GEN01, from Ethicon Endo-Surgery, Inc., Cincinnati, Ohio. When the acoustic assembly 24 is energized, a vibratory motion standing wave is generated through the acoustic assembly 24. A suitable vibrational frequency range may be about 20 Hz to 120 kHz and a well-suited vibrational frequency range may be about 30-70 kHz and one example operational vibrational frequency may be approximately 55.5 kHz.

The amplitude of the vibratory motion at any point along the acoustic assembly 24 may depend upon the location along the acoustic assembly 24 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node (i.e., where motion is usually maximal). The distance between an anti-node and its nearest node is one-quarter wavelength ($\lambda/4$).

As outlined above, the wires 38 and 40 transmit an electrical signal from the ultrasonic signal generator 12 to the positive electrodes 34 and the negative electrodes 36. The piezoelectric elements 32 are energized by the electrical signal supplied from the ultrasonic signal generator 12 in response to a foot switch 44, for example, to produce an acoustic standing wave in the acoustic assembly 24. The electrical signal causes disturbances in the piezoelectric elements 32 in the form of repeated small displacements resulting in large compression forces within the material. The repeated small displacements cause the piezoelectric elements 32 to expand and contract in a continuous manner along the axis of the voltage gradient, producing longitudinal waves of ultrasonic energy.

In various embodiments, the ultrasonic energy produced by transducer 14 can be transmitted through the acoustic assembly 24 to the end effector 50 via an ultrasonic transmission waveguide 46. In order for the acoustic assembly 24 to deliver energy to the end effector 50, the components of the acoustic assembly 24 are acoustically coupled to the end effector 50. For example, the distal end of the ultrasonic transducer 14 may be acoustically coupled at the surface 30 to the proximal end of the ultrasonic transmission waveguide 46 by a threaded connection such as a stud 48.

The components of the acoustic assembly 24 can be acoustically tuned such that the length of any assembly is an integral number of one-half wavelengths ($n\lambda/2$), where the wavelength $\lambda$ is the wavelength of a pre-selected or operating longitudinal vibration drive frequency $f_d$ of the acoustic assembly 24, and where n is any positive integer. It is also contemplated that the acoustic assembly 24 may incorporate any suitable arrangement of acoustic elements.

The ultrasonic end effector 50 may have a length substantially equal to an integral multiple of one-half system wavelengths ($\lambda/2$). A distal end 52 of the ultrasonic end effector 50 may be disposed at, or at least near, an antinode in order to provide the maximum, or at least nearly maximum, longitudinal excursion of the distal end. When the transducer assembly is energized, in various embodiments, the distal end 52 of the ultrasonic end effector 50 may be configured to move in the range of, for example, approximately 10 to 500 microns peak-to-peak and preferably in the range of approximately 30 to 150 microns at a predetermined vibrational frequency.

As outlined above, the ultrasonic end effector 50 may be coupled to the ultrasonic transmission waveguide 46. In various embodiments, the ultrasonic end effector 50 and the ultrasonic transmission guide 46 as illustrated are formed as a single unit construction from a material suitable for transmission of ultrasonic energy such as, for example, Ti6Al4V (an alloy of titanium including aluminum and vanadium), aluminum, stainless steel, and/or any other suitable material. Alternately, the ultrasonic end effector 50 may be separable (and of differing composition) from the ultrasonic transmission waveguide 46, and coupled by, for example, a stud, weld, glue, quick connect, or other suitable known methods. The ultrasonic transmission waveguide 46 may have a length substantially equal to an integral number of one-half system wavelengths ($\lambda/2$), for example. The ultrasonic transmission waveguide 46 may be preferably fabricated from a solid core shaft constructed out of material that propagates ultrasonic energy efficiently, such as titanium alloy (i.e., Ti6Al4V) or an aluminum alloy, for example.

In various embodiments, referring to FIG. 2, the ultrasonic transmission waveguide 46 can comprise a longitudinally projecting attachment post 54 at a proximal end to couple to the surface 30 of the acoustic assembly by a threaded connection such as the stud 48. The distal end of the ultrasonic transmission waveguide 46 may be coupled to the proximal end of the end effector 50 by an internal threaded connection, for example, preferably at or near an antinode. It is contemplated that the end effector 50 may be attached to the ultrasonic transmission waveguide 46 by any suitable means, such as a welded joint or the like, for example. Although the end effector 50 may be detachable from the ultrasonic transmission waveguide 46, it is also contemplated that the end effector 50 and the ultrasonic transmission waveguide 46 may be formed as a single unitary piece.

In various embodiments, further to the above, FIG. 2 illustrates one embodiment of a connection union/joint 70 for an ultrasonic instrument. The connection union/joint 70 may be formed between the attachment post 54 of the ultrasonic transmission waveguide 46 and the surface 30 of the velocity transformer 28 at the distal end of the acoustic assembly 24. The proximal end of the attachment post 54 comprises a female threaded substantially cylindrical recess 66 to receive a portion of the threaded stud 48 therein. The distal end of the velocity transformer 28 also may comprise a female threaded substantially cylindrical recess 68 to receive a portion of the threaded stud 48. The recesses 66, 68 are substantially circumferentially and longitudinally aligned.

In the embodiment illustrated in FIG. 1, the ultrasonic transmission waveguide 46 comprises a plurality of stabilizing silicone rings or compliant supports 56 positioned at, or at least near, a plurality of nodes. The silicone rings 56 can dampen undesirable vibration and isolate the ultrasonic energy from a sheath 58 at least partially surrounding waveguide 46, thereby assuring the flow of ultrasonic energy in a longitudinal direction to the distal end 52 of the end effector 50 with maximum efficiency.

As shown in FIG. 1, the sheath 58 can be coupled to the distal end of the handpiece assembly 60. The sheath 58 generally includes an adapter or nose cone 62 and an elongated tubular member 64. The tubular member 64 is attached to and/or extends from the adapter 62 and has an opening extending longitudinally therethrough. In various embodiments, the sheath 58 may be threaded or snapped onto the distal end of the housing 16. In at least one embodiment, the ultrasonic transmission waveguide 46 extends through the opening of the tubular member 64 and the silicone rings 56 can contact the sidewalls of the opening and isolate the ultrasonic transmission waveguide 46 therein. In various embodiments, the adapter 62 of the sheath 58 is preferably constructed from Ultem®, for example, and the tubular member 64 is fabricated from stainless steel, for example. In at least one embodiment, the ultrasonic transmission waveguide 46 may have polymeric material, for example, surrounding it in order to isolate it from outside contact.

In various embodiments, as described above, a surgical instrument can comprise a transducer configured to produce longitudinal vibrations, an end effector and/or wave guide operably coupled to the transducer, and other various acoustic assembly components which operably connect, and/or support, the transducer, wave guide, and/or end effector. In certain embodiments, as also described above, the transducer can produce vibrations which can be transmitted to the end effector, wherein the vibrations can drive the transducer, the wave guide, the end effector, and/or the other various components of the acoustic assembly at, or near, a resonant frequency. In resonance, a longitudinal strain pattern, or longitudinal stress pattern, can develop within the transducer, the wave guide, and/or the end effector, for example. In various embodiments, referring now to FIGS. 3 and 4, such a longitudinal strain pattern, or longitudinal stress pattern, can cause the longitudinal strain, or longitudinal stress, to vary along the length of the transducer, wave guide, and/or end effector, in a sinusoidal, or at least substantially sinusoidal, manner. In at least one embodiment, for example, the longitudinal strain pattern can have maximum peaks and zero points, wherein the strain values can vary in a non-linear manner between such peaks and zero points.

Figure 3:
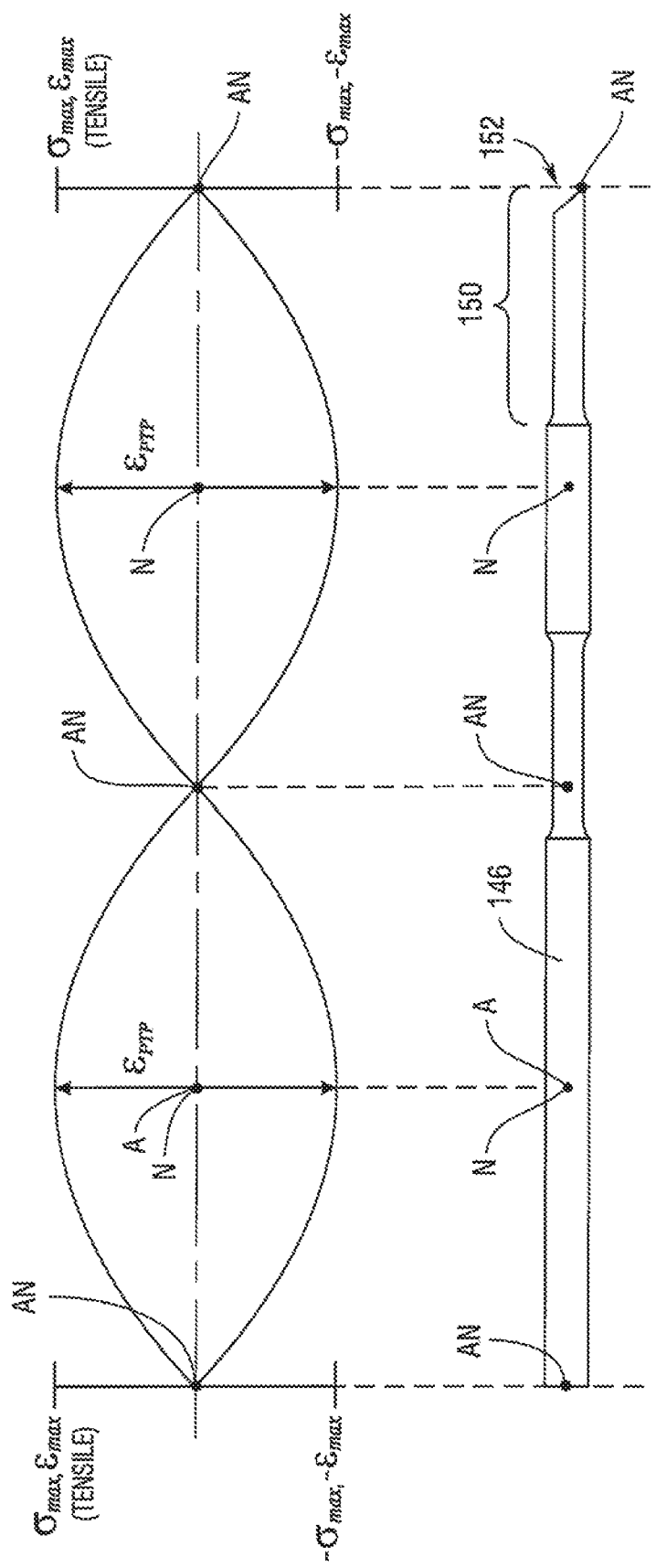
FIG. 3 is a schematic of an end effector and a wave guide of an ultrasonic surgical instrument and a representative longitudinal strain pattern and longitudinal stress pattern developed within the wave guide and end effector.
Figure 4:
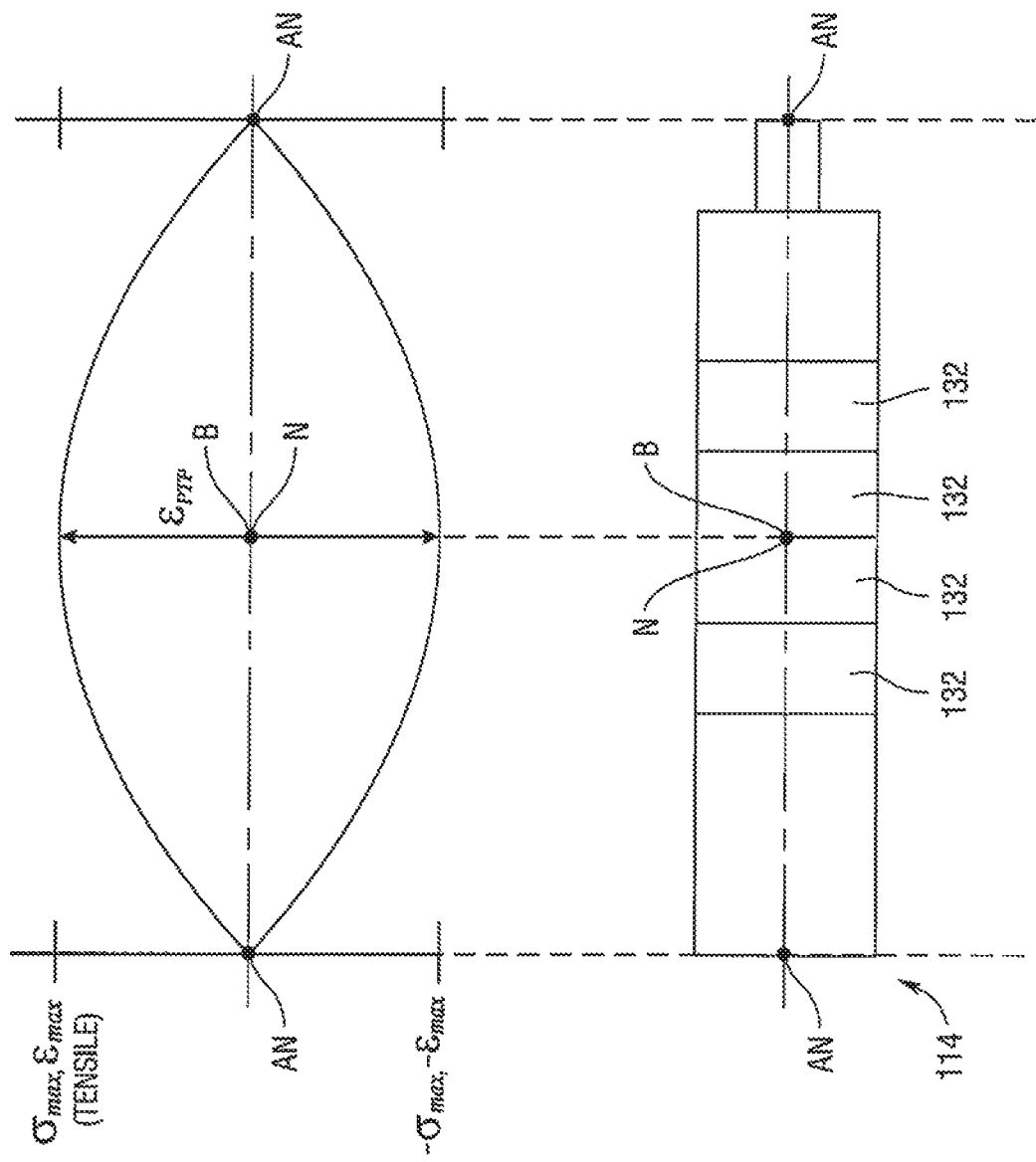
FIG. 4 is a schematic of a transducer of an ultrasonic surgical instrument and a representative longitudinal strain pattern and longitudinal stress pattern developed within the transducer.

In various circumstances, further to the above, the longitudinal strain, or longitudinal stress, at any given location within wave guide 146 and/or end effector 150, for example, can be pulsed between various strain, or stress, states. Referring to FIGS. 3 and 4, for example, the longitudinal strain within wave guide 146 at Point A can be cycled between a tensile, or positive, $\varepsilon_{max}$ and a compressive, or negative, $\varepsilon_{max}$, when a cyclical voltage is supplied to the piezoelectric elements 132 of transducer 114, for example, and especially when the system substantially comprising wave guide 146, end effector 150, and transducer 114 is vibrated at or near its resonant frequency. In various circumstances, the absolute values of the compressive and tensile maximum longitudinal strains can be equal, or at least substantially equal. Correspondingly, the longitudinal stress within wave guide 146 at Point A can be can be cycled between a tensile, or positive, $\sigma_{max}$ and a compressive, or negative, $\sigma_{max}$ wherein the absolute values of the compressive and tensile maximum longitudinal stresses can be equal, or at least substantially equal. Similarly, referring to FIG. 4, the longitudinal strain within transducer 114 at Point B can be cycled between a tensile $\varepsilon_{max}$ and a compressive $\varepsilon_{max}$ and the longitudinal stress can by cycled between a tensile $\sigma_{max}$ and a compressive $\sigma_{max}$.

In various embodiments, as outlined above, the longitudinal strain, or longitudinal stress, within any given point within wave guide 146 and/or end effector 150 can be cycled between two values, the absolute values of which can be substantially the same. In such embodiments, the range of longitudinal strain, or longitudinal stress, incurred at a location can be evaluated as a peak-to-peak value, i.e., $\varepsilon_{ptp}$ or $\sigma_{ptp}$, respectively. In at least one embodiment, although not illustrated, the voltage supplied to piezoelectric elements 132 of transducer 114 can be rectified such that the voltage is cycled between zero and a maximum voltage or, alternatively, between zero and a minimum voltage wherein, as a result, the longitudinal strain profile can be cycled between zero and a maximum compressive strain or, alternatively, between zero and a maximum tensile strain. In any event, referring again to the longitudinal stress and longitudinal strain patterns depicted in FIG. 3, the stress pattern is illustrated as overlapping the strain pattern. In various circumstances, however, the longitudinal stress and longitudinal strain within any given point in wave guide 146 and/or end effector 150 will not have the same magnitude. Rather, the magnitude of the stress, measured in psi, for example, may be larger, and most likely substantially larger, than the magnitude of the strain, measured in an in/in unitless dimension. In various circumstances, the stress ($\sigma$) and strain ($\varepsilon$) values can be linearly proportional and can be related by the relationship:

$$\sigma = E * \varepsilon$$

wherein E comprises the modulus of elasticity of the material of the wave guide 146 and/or end effector 150, for example, at a particular point.

Figure 5:
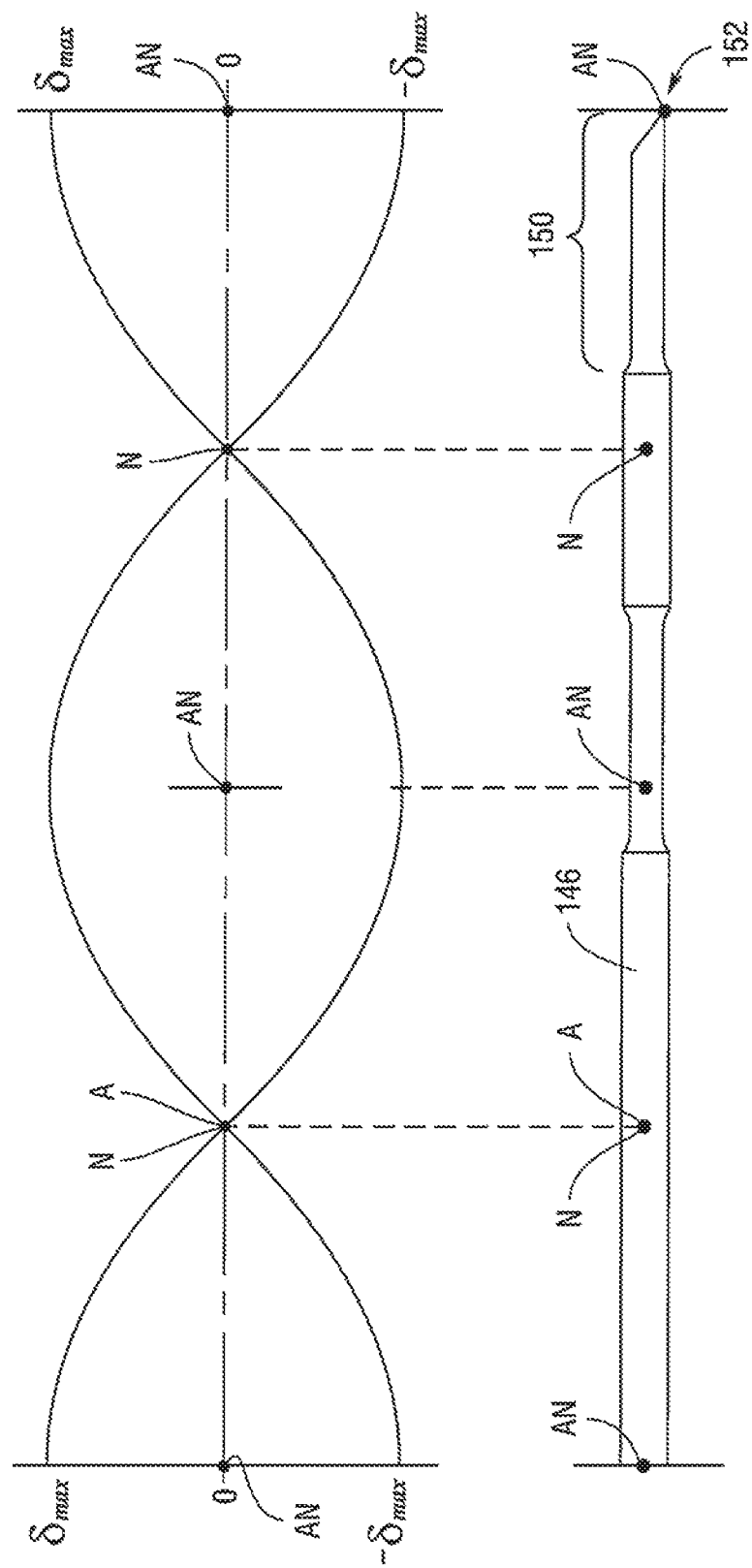
FIG. 5 is a schematic of the end effector and wave guide illustrated in FIG. 3 and a representative longitudinal displacement pattern developed within the wave guide and end effector.
Figure 6:
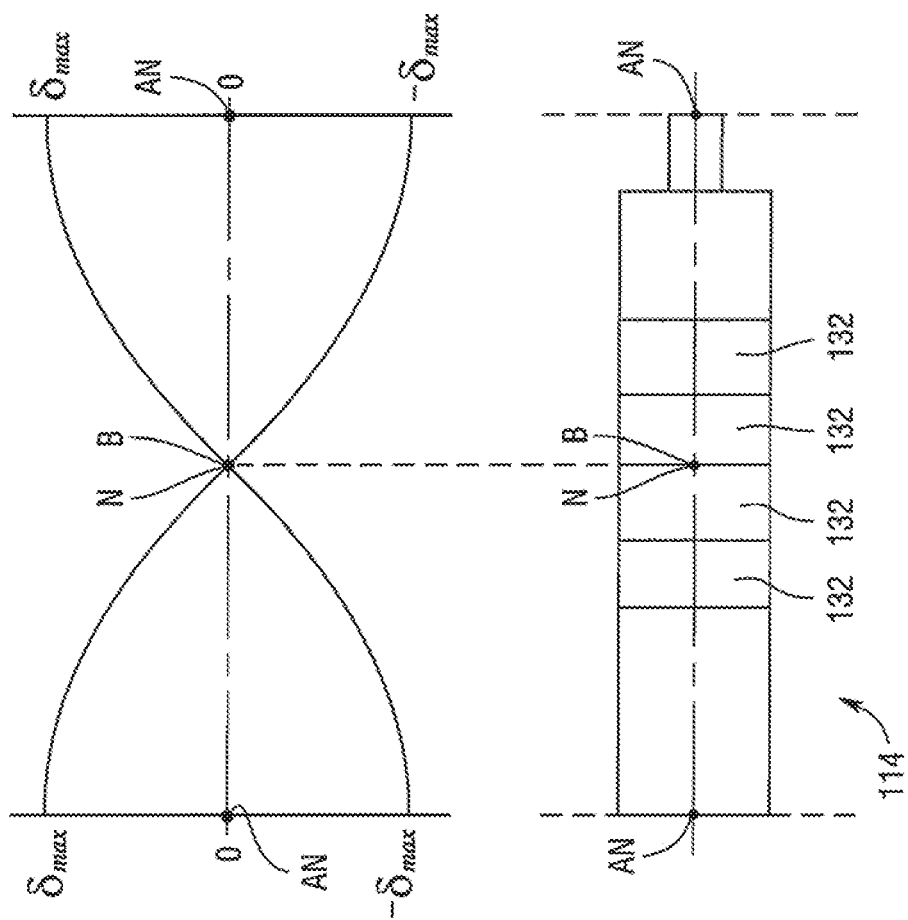
FIG. 6 is a schematic of the transducer illustrated in FIG. 4 and a representative longitudinal displacement pattern developed within the transducer.

In various embodiments, a longitudinal strain pattern, or longitudinal stress pattern, within transducer 116, wave guide 146 and/or end effector 150, as depicted in FIGS. 3 and 4, for example, can comprise one or more zero-strain, or one or more zero-stress, points. In conjunction with FIGS. 5 and 6, the zero-strain and zero-stress points within transducer 116, wave guide 146, and end effector 150 can coincide with the anti-nodes of the standing wave of vibrations within transducer 116, wave guide 146, and end effector 150, wherein the anti-nodes are represented by Points AN. As the reader will recall, referring to FIGS. 5 and 6, the anti-nodes of a standing wave of longitudinal vibrations can correspond with the maximum longitudinal vibrational displacement, i.e., $\delta_{max}$ and/or $-\delta_{max}$, for example, of the standing wave of vibrations. Furthermore, the maximum-strain and maximum-stress points within transducer 116, wave guide 146, and end effector 150 can coincide with the nodes of the standing wave of vibrations which are represented by points N. As the reader will also recall, referring to FIGS. 5 and 6, the nodes of a standing wave of longitudinal vibrations can correspond with the zero longitudinal displacement points of the standing wave of vibrations. As illustrated in FIG. 3, referring to the discussion above, Point A is at or near a node N. As also illustrated in FIG. 3, the distal end 152 of end effector 150 is positioned at or near an antinode AN and, similarly, the proximal end of wave guide 146 is also positioned at an antinode AN. As discussed above, certain advantages can be obtained by assuring that the distal end 152 of end effector 150 is positioned at, or near, an antinode, wherein at least one such advantage can include capitalizing on the maximum longitudinal vibration displacement realized at an antinode, for example. Certain other advantages can be obtained by assuring that the proximal end of wave guide 146 is positioned at, or near, an antinode, wherein at least one such advantage can include capitalizing on the longitudinal zero strain, or longitudinal zero stress, point realized at an antinode. Similar to the above, the proximal end of wave guide 146 can comprise a connection or union joint, such as the connection joint 70 illustrated in FIG. 2, for example, and, by placing this connection joint at or near an antinode, the joint may be exposed to little, if any, longitudinal stress or longitudinal strain induced by the standing wave of vibrations.

As described above, a voltage, or power, source can be operably coupled with one or more of the piezoelectric elements of a transducer, wherein a voltage potential applied to each of the piezoelectric elements can cause the piezoelectric elements to expand and contract, or vibrate, in a longitudinal direction. As also described above, the voltage potential can be cyclical and, in various embodiments, the voltage potential can be cycled at a frequency which is the same as, or nearly the same as, the resonant frequency of the system of components comprising transducer 116, wave guide 146, and end effector 150, for example. In various embodiments, however, certain of the piezoelectric elements within the transducer may contribute more to the standing wave of longitudinal vibrations than other piezoelectric elements within the transducer. More particularly, a longitudinal strain profile may develop within a transducer wherein the strain profile may control, or limit, the longitudinal displacements that some of the piezoelectric elements can contribute to the standing wave of vibrations, especially when the system is being vibrated at or near its resonant frequency.

Figure 7:
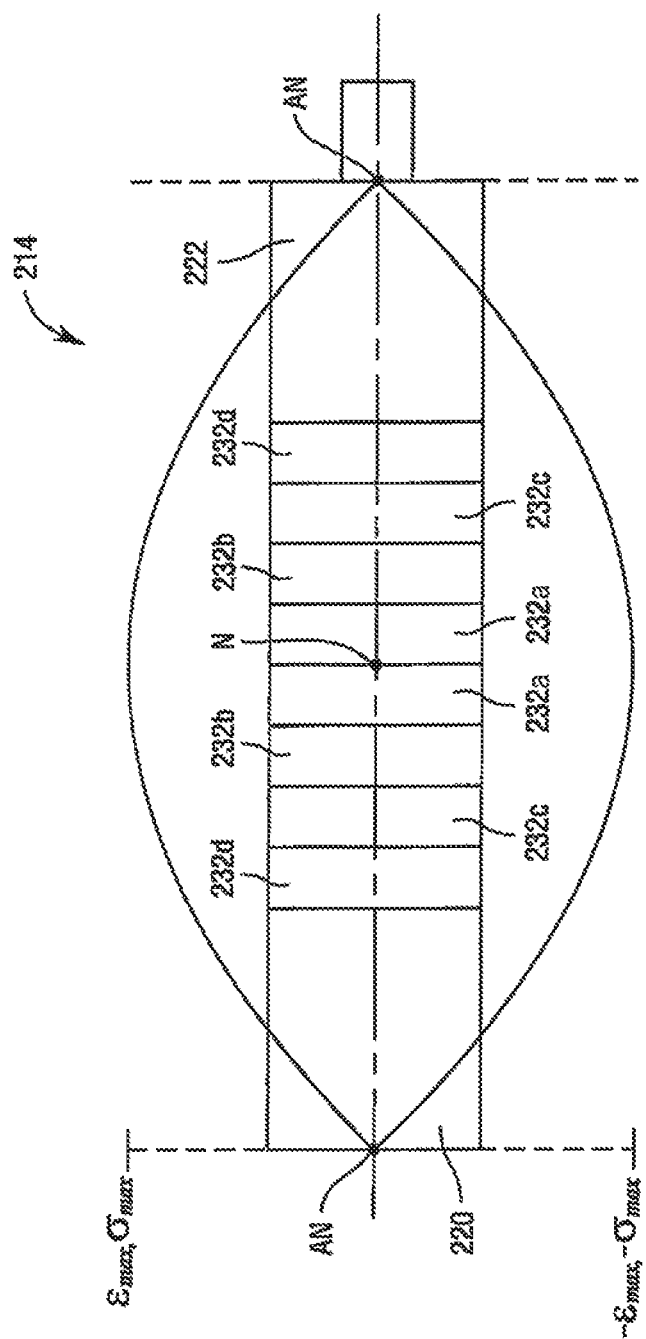
FIG. 7 is a schematic of a transducer of an ultrasonic surgical instrument in accordance with at least one embodiment and a representative longitudinal strain pattern and a representative longitudinal stress pattern developed within the transducer.

Referring now to FIG. 7, piezoelectric elements 232a, which are positioned closer to node N than the other piezoelectric elements of transducer 214, can be subjected to a larger strain, or stress, than the other piezoelectric elements of transducer 214. In various embodiments, the strain within a piezoelectric element can determine the amount of current that can flow, or be drawn through, the piezoelectric element. In certain embodiments, the strain and the current can be linearly proportional while, in other embodiments, the strain and the current can be geometrically proportional. As piezoelectric elements 232a are positioned closest to the node within transducer 214, and thus exposed to the highest strain, piezoelectric elements 232a may be able to draw more current from the power source than the other piezoelectric elements which are positioned further away from the node and exposed to lesser strains. The larger currents flowing through piezoelectric elements 232a, for example, can cause piezoelectric elements 232a to have larger longitudinal vibrations and contribute larger displacements to the standing wave of vibrations within transducer 214, and an end effector attached thereto, than the other piezoelectric elements of transducer 214 which are positioned further away from the node. In certain embodiments, the current drawn by a piezoelectric element and the longitudinal displacement of the piezoelectric element can be linearly proportional while, in other embodiments, the current and the longitudinal displacement can be geometrically proportional.

By way of example, further to the above, piezoelectric elements 232a are closer to node N than piezoelectric elements 232b and, as illustrated in FIG. 7, piezoelectric elements 232b may be subjected to less strain than piezoelectric elements 232a. As a result, in accordance with the above, piezoelectric elements 232b may draw less current than piezoelectric elements 232a. Furthermore, as the power consumed by a piezoelectric element can be defined by the product of the current flowing through the piezoelectric element and the voltage potential applied across the piezoelectric element, piezoelectric elements 232b may consume less power than piezoelectric elements 232a. Such a relationship may be especially true in embodiments in which the voltage potential across piezoelectric elements 232a and 232b is the same, or at least substantially the same. Correspondingly, piezoelectric elements 232c may draw less current and consume less power than piezoelectric elements 232b and, similarly, piezoelectric elements 232d may draw less current and consume less power than piezoelectric elements 232c.

Further to the above, piezoelectric elements which draw larger currents and consume larger quantities of power can perform larger quantities of work. More particularly, such piezoelectric elements can create larger longitudinal displacements and/or generate larger longitudinal forces when they are vibrated and, as the work produced by a piezoelectric element can be proportional to the product of the forces and the displacements that are generated by the piezoelectric element, such piezoelectric elements can output more work. As a result of the above, piezoelectric elements which are positioned closer to a node may produce more work than piezoelectric elements which are positioned further away from the node. This may be especially true in embodiments where the piezoelectric elements of a transducer are comprised of the same material and are substantially the same size. In various embodiments, however, piezoelectric elements which consume larger quantities of power and perform larger quantities of work can generate larger quantities of heat. In at least one embodiment, as a result, the piezoelectric elements positioned closest to the node may produce more heat than piezoelectric elements which are positioned further away from the node. In various circumstances, the flow of heat away from the piezoelectric elements positioned closest to the node may be inhibited as such piezoelectric elements may be positioned intermediate adjacent piezoelectric elements which may reduce the flow of air therearound. In certain circumstances, larger quantities of heat can have a negative impact on the performance of various piezoelectric elements. For example, larger quantities of heat can produce pyroectricity within one or more of the piezoelectric elements which can counteract the voltage potential applied thereto and/or possibly reduce the life of the piezoelectric elements.

In various embodiments, further to the above, a transducer can comprise several different piezoelectric elements, wherein the piezoelectric elements can be selected in order to equalize, or at least better distribute, the work performed by the piezoelectric elements of the transducer. In certain embodiments, piezoelectric elements positioned further away from a node may produce the same work as piezoelectric elements positioned closer to the node. In certain other embodiments, piezoelectric elements positioned further away from a node may not produce the same work as piezoelectric elements positioned closer to the node, but they may produce approximately 90%, approximately 80%, approximately 70%, approximately 60%, approximately 50%, approximately 40%, and/or approximately 30% of the work produced by piezoelectric elements positioned closer to the node. In at least one embodiment, the different piezoelectric elements can be comprised of materials which have different strain constants (d33), wherein the strain constant of a material can be expressed as the ratio of the strain (c) produced within a material divided by the electric field (E) experienced by the piezoelectric element. In at least one such embodiment, referring again to FIG. 7, for example, piezoelectric elements 232a can be comprised of a first material having a first strain constant and piezoelectric elements 232b can be comprised of a second material having a second strain constant, for example. In various embodiments, the first strain constant can be higher than the second strain constant. Generally, the current needed by a piezoelectric element to produce a certain amount of work can be inversely proportional to the strain constant of the piezoelectric element and, thus, selecting a material for a piezoelectric element which has a higher strain constant can reduce the current that the piezoelectric element will draw and, correspondingly, reduce the heat that the piezoelectric element will produce. Correspondingly, selecting a material for a piezoelectric element which has a lower strain constant can increase the current required to produce a certain amount of work, and thus increase the heat that the piezoelectric element will produce.

Further to the above, the work produced by the piezoelectric elements of a transducer can be balanced, or at least more evenly balanced, by utilizing piezoelectric elements comprised of a material having a higher strain constant closer to a node and utilizing piezoelectric elements comprised of a material having a lower strain constant further away from the node. In various embodiments, piezoelectric elements 232a can be comprised of a first material having a first strain constant, piezoelectric elements 232b can be comprised of a second material having a second strain constant, piezoelectric elements 232c can be comprised of a third material having a third strain constant, and piezoelectric elements 232d can be comprised of a fourth material having a fourth strain constant, wherein, in at least one embodiment, the first strain constant can be larger than the second strain constant, the second strain constant can be larger than the third strain constant, and the third strain constant can be larger than the fourth strain constant. In various embodiments, the strain constants of the piezoelectric elements can range between approximately 100 $e^{-12}$ m/V and approximately 600 $e^{-12}$ m/V, and/or between approximately 150 $e^{-12}$ m/V and approximately 500 $e^{-12}$ m/V, and/or between approximately 150 $e^{-12}$ m/V and approximately 350 $e^{-12}$ m/V, for example. In any event, owing to the selection of materials for the piezoelectric elements, referring again to FIG. 7, piezoelectric elements 232b may produce the same quantity of work as, or at least a large fraction of, the work produced by piezoelectric elements 232a, for example, and, similarly, piezoelectric elements 232c may produce the same quantity of work as, or at least a large fraction of, the work produced by piezoelectric elements 232b, for example. Likewise, piezoelectric elements 232d may produce the same quantity of work as, or at least a large fraction of, the work produced by piezoelectric elements 232c.

In various embodiments, as a result of the above, the heat generated by the piezoelectric elements of a transducer can be balanced, or at least more evenly balanced, such that the heat is generated evenly, or at least more evenly, throughout the transducer. Such embodiments can prevent, or at least reduce the possibility of, an undesirable quantity of heat from being generated and/or retained within a single, or centralized, location within the transducer, for example. In certain circumstances, as a result of the above, piezoelectric elements 232b may generate the same quantity of heat as, or at least a large fraction of, the heat generated by piezoelectric elements 232a, for example, and, similarly, piezoelectric elements 232c may generate the same quantity of heat as, or at least a large fraction of, the heat generated by piezoelectric elements 232b, for example. Likewise, piezoelectric elements 232d may generate the same quantity of heat as, or at least a large fraction of, the heat generated by piezoelectric elements 232c. In at least one such embodiment, the heat generated and/or retained by the piezoelectric elements can be evenly distributed, or at least more evenly distributed, within the transducer 214. In various embodiments, the additional heat generated and/or retained within piezoelectric elements 232d, for example, can be more easily drawn into distal end member 222 and/or proximal end member 220, for example, such that the heat can be more easily dissipated from transducer 214. In certain embodiments, end members 220 and 222 can comprise heat sinks which can draw heat away from the piezoelectric elements, wherein, in at least one embodiment, end members 220 and 222 can be comprised of metal, for example. In such embodiments, the possibility of the piezoelectric elements becoming overheated can be reduced.

In various alternative embodiments, it may be desirable to utilize piezoelectric elements comprised of a material having a lower strain constant closer to a node and piezoelectric elements comprised of a material having a higher strain constant further away from the node. In various embodiments, piezoelectric elements 232a can be comprised of a first material having a first strain constant, piezoelectric elements 232b can be comprised of a second material having a second strain constant, piezoelectric elements 232c can be comprised of a third material having a third strain constant, and piezoelectric elements 232d can be comprised of a fourth material having a fourth strain constant, wherein, in at least one embodiment, the first strain constant can be smaller than the second strain constant, the second strain constant can be smaller than the third strain constant, and the third strain constant can be smaller than the fourth strain constant.

In certain embodiments, further to the above, the heat generated by the piezoelectric elements of a transducer can be balanced, or at least more evenly balanced, by utilizing materials having different dielectric dissipation or dampening properties. In various circumstances, the dielectric dissipation of a material can be expressed as the measure of the loss-rate of power of a mode of oscillation in a dissipative system. Stated another way, in certain circumstances, the dielectric dissipation of a material can represent the energy dissipation, or losses, that can occur within a vibrating piezoelectric element, and/or transducer, wherein such dissipation, or losses, can result in heat generation. In any event, in various embodiments, different materials can be utilized which have larger and/or smaller dissipative or dampening qualities, wherein materials having smaller dissipative or dampening qualities may generate less heat, for example. In at least one embodiment, piezoelectric elements comprised of materials having smaller dissipative qualities can be positioned closer to a node whereas piezoelectric elements comprised of materials having larger dissipative qualities can be positioned further away from a node. In various embodiments, the dielectric dissipation factor of the piezoelectric materials of a transducer can range between approximately 0.002 and approximately 0.01, for example.

In certain embodiments, further to the above, the work generated by the piezoelectric elements of a transducer can be balanced, or at least more evenly balanced, by utilizing materials having different dielectric constants. In various embodiments, piezoelectric elements comprised of materials having a lower dielectric constant may be able to produce more work than piezoelectric elements having a higher dielectric constant. In at least one embodiment, as a result, piezoelectric elements 232a can be comprised of a first material having a first dielectric constant, piezoelectric elements 232b can be comprised of a second material having a second dielectric constant, piezoelectric elements 232c can be comprised of a third material having a third dielectric constant, and piezoelectric elements 232d can be comprised of a fourth material having a fourth dielectric constant, wherein, in at least one embodiment, the first dielectric constant can be larger than the second dielectric constant, the second dielectric constant can be larger than the third dielectric constant, and the third dielectric constant can be larger than the fourth dielectric constant. In various embodiments, further to the above, the relative dielectric constants of the piezoelectric materials can range between approximately 900 and approximately 1200, for example, wherein the relative dielectric constant of a material ($\varepsilon_r$) can be defined as the static permittivity of the material ($\varepsilon_s$) divided by the permittivity constant ($\varepsilon_0$). In any event, owing to the selection of materials for the piezoelectric elements, referring again to FIG. 7, piezoelectric elements 232b may produce the same quantity of work as, or at least a large fraction of, the work produced by piezoelectric elements 232a, for example, and, similarly, piezoelectric elements 232c may produce the same quantity of work as, or at least a large fraction of, the work produced by piezoelectric elements 232b, for example. Likewise, piezoelectric elements 232d may produce the same quantity of work as, or at least a large fraction of, the work produced by piezoelectric elements 232c.

In certain embodiments, further to the above, the work generated by the piezoelectric elements of a transducer can be balanced, or at least more evenly balanced, by utilizing materials having different voltage sensitivities. In various embodiments, piezoelectric elements comprised of materials having a higher voltage sensitivity may be able to produce more work than piezoelectric elements having a lower voltage sensitivity. In at least one embodiment, as a result, piezoelectric elements 232a can be comprised of a first material having a first voltage sensitivity, piezoelectric elements 232b can be comprised of a second material having a second voltage sensitivity, piezoelectric elements 232c can be comprised of a third material having a third voltage sensitivity, and piezoelectric elements 232d can be comprised of a fourth material having a fourth voltage sensitivity, wherein, in at least one embodiment, the first voltage sensitivity can be smaller than the second voltage sensitivity, the second voltage sensitivity can be smaller than the third voltage sensitivity, and the third voltage sensitivity can be smaller than the fourth voltage sensitivity. In various embodiments, the voltage sensitivity of a piezoelectric material can be defined as the responsiveness, or change in shape, of the material to a voltage potential, wherein piezoelectric materials having a higher voltage sensitivity may require less voltage to produce larger displacements within the material. In any event, owing to the selection of materials for the piezoelectric elements, referring again to FIG. 7, piezoelectric elements 232b may produce the same quantity of work as, or at least a large fraction of, the work produced by piezoelectric elements 232a, for example, and, similarly, piezoelectric elements 232c may produce the same quantity of work as, or at least a large fraction of, the work produced by piezoelectric elements 232b, for example. Likewise, piezoelectric elements 232d may produce the same quantity of work as, or at least a large fraction of, the work produced by piezoelectric elements 232c.

As discussed above, referring again to FIG. 7, the piezoelectric elements of a transducer which are positioned closer to a node may generate and/or retain more heat than the piezoelectric elements of a transducer which are positioned further away from a node. As also discussed above, the materials of the piezoelectric elements can be selected such that the heat produced and/or retained by the piezoelectric elements can be leveled, or at least better leveled, across the transducer. In various circumstances, however, heat generation and/or retention may be centralized within the piezoelectric elements near the node. In various embodiments, as discussed in greater detail below, the piezoelectric elements of a transducer can be comprised of different materials having different Curie temperatures ($T_c$). The Curie temperature of piezoelectric materials can be described as the temperature above which a piezoelectric material may lose its polarization and piezoelectric characteristics. In various circumstances, as a result, it may be desirable that the temperatures of the piezoelectric materials do not exceed their Curie temperatures.

In various embodiments, especially in embodiments where there is a large thermal gradient in the transducer between the piezoelectric elements 232a at the center, or node, of the transducer stack and the piezoelectric elements 232d at the ends, or antinodes, of the transducer stack, the piezoelectric elements positioned closer to the node can be comprised of a material having a higher Curie temperature than the Curie temperature of the piezoelectric elements positioned further away from the node. In at least one embodiment, piezoelectric elements 232a can be comprised of a first material having a first Curie temperature, piezoelectric elements 232b can be comprised of a second material having a second Curie temperature, piezoelectric elements 232c can be comprised of a third material having a third Curie temperature, and piezoelectric elements 232d can be comprised of a fourth material having a fourth Curie temperature, wherein, in at least one embodiment, the first Curie temperature can be larger than the second Curie temperature, the second Curie temperature can be larger than the third Curie temperature, and the third Curie temperature can be larger than the fourth Curie temperature. In at least one such embodiment, for example, piezoelectric elements 232a and/or 232b, for example, can be comprised of (K, Na)NbO$_3$, which is commonly-referred to as sodium potassium niobate or "KNN" and has a Curie temperature of approximately 410° C. Further to the above, piezoelectric elements 232a and/or 232b can be comprised of Bi4Ti3O12, which is commonly-referred to as "BTO" and has a Curie temperature of approximately 280° C., and/or (Bi, Na)TiO$_3$—(Bi, K)TiO$_3$—(Ba, Sr)TiO$_3$, which is commonly-referred to as "BNBK" and has a Curie temperature of approximately 675° C., and/or any suitable high Tc lead-free piezoelectric material, for example. In addition to the above, piezoelectric elements 232c and/or 232d, for example, can be comprised of BaTiO3, which is commonly-referred to as barium titanate and has a Curie temperature of approximately 110° C., and/or any suitable low Tc lead-free piezoelectric material, for example. In at least one embodiment, piezoelectric elements 232a can be comprised of BNBK ($T_c$=675° C.), piezoelectric elements 232b can be comprised of KNN ($T_c$=410° C.), piezoelectric elements 232c can be comprised of BTO ($T_c$=280° C.), and piezoelectric elements 232d may be comprised of barium titanate ($T_c$=110° C.), for example. Although such arrangements may be useful in various circumstances, each of the piezoelectric elements within a transducer stack can be comprised of one or more of any of the materials mentioned herein.

In various embodiments, further to the above, the first piezoelectric elements 232a having a first Curie temperature can draw a first current, the second piezoelectric elements 232b having a second Curie temperature can draw a second current, wherein the first current can be larger in magnitude than the second current. Owing to a higher first Curie temperature, the first, or higher, current may not detrimentally overheat the first piezoelectric elements 232a and, similarly, the second, or lower, current may not detrimentally overheat the second piezoelectric elements 232b. In at least one such embodiment, the third piezoelectric elements 232c can draw a third current which has a lower magnitude than the second current and, in addition, the fourth piezoelectric elements 232d can draw a fourth current which has a lower magnitude than the third current.

Figure 8:
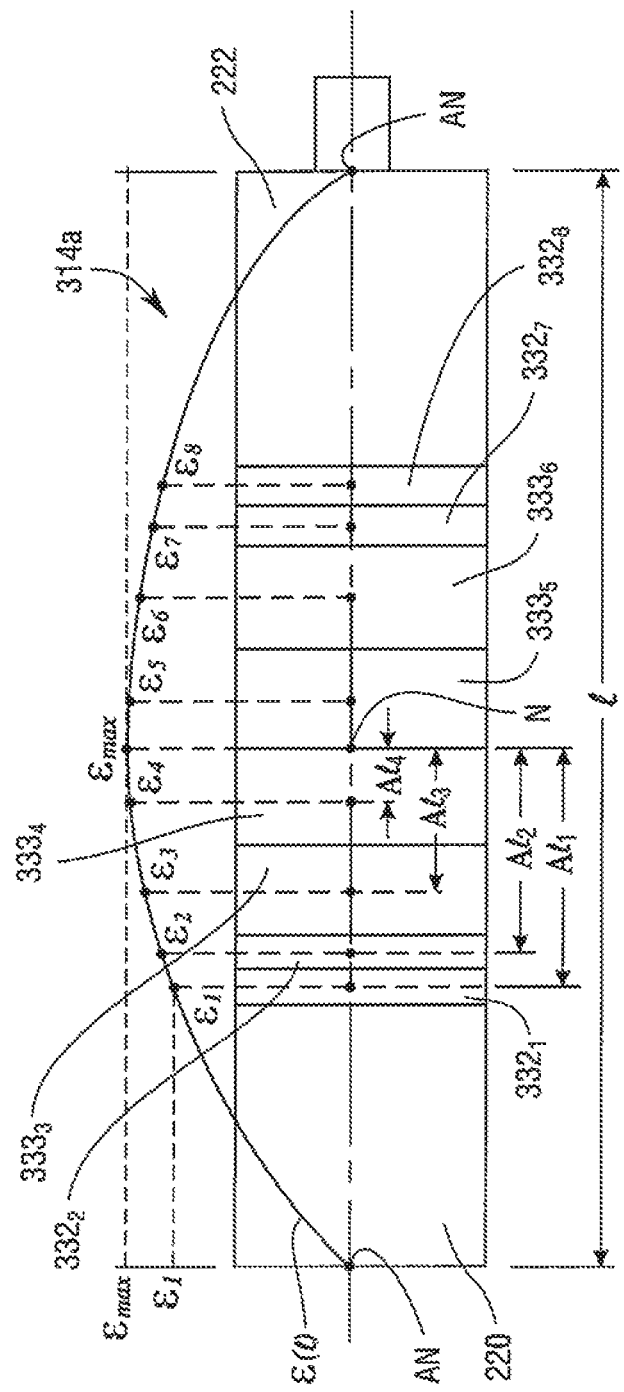
FIG. 8 illustrates an embodiment of a transducer comprising piezoelectric elements having different thicknesses.
Figure 9:
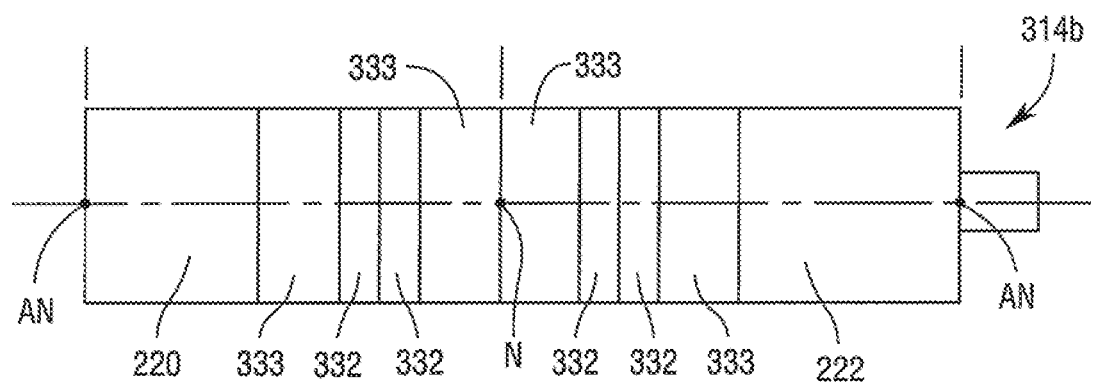
FIG. 9 illustrates a second embodiment of a transducer comprising piezoelectric elements having different thicknesses.
Figure 10:
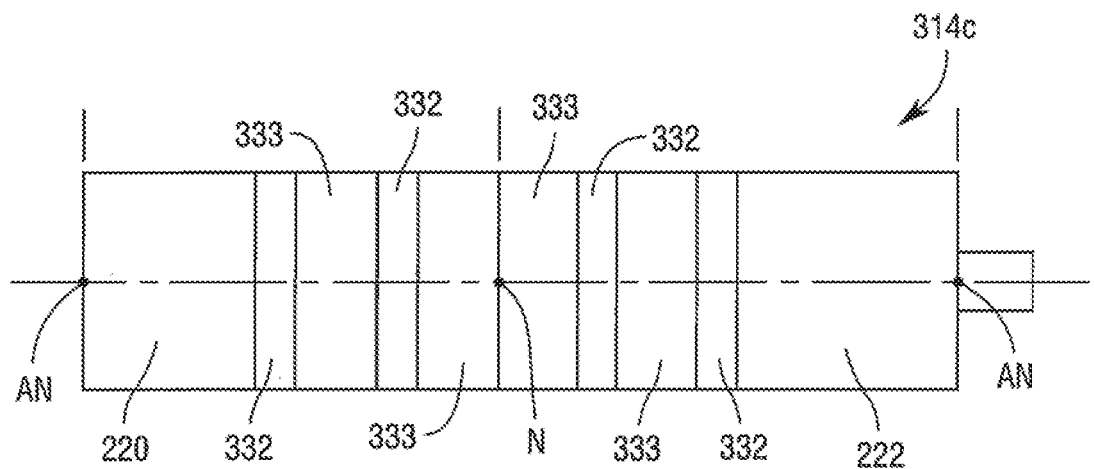
FIG. 10 illustrates a third embodiment of a transducer comprising piezoelectric elements having different thicknesses.
Figure 14:
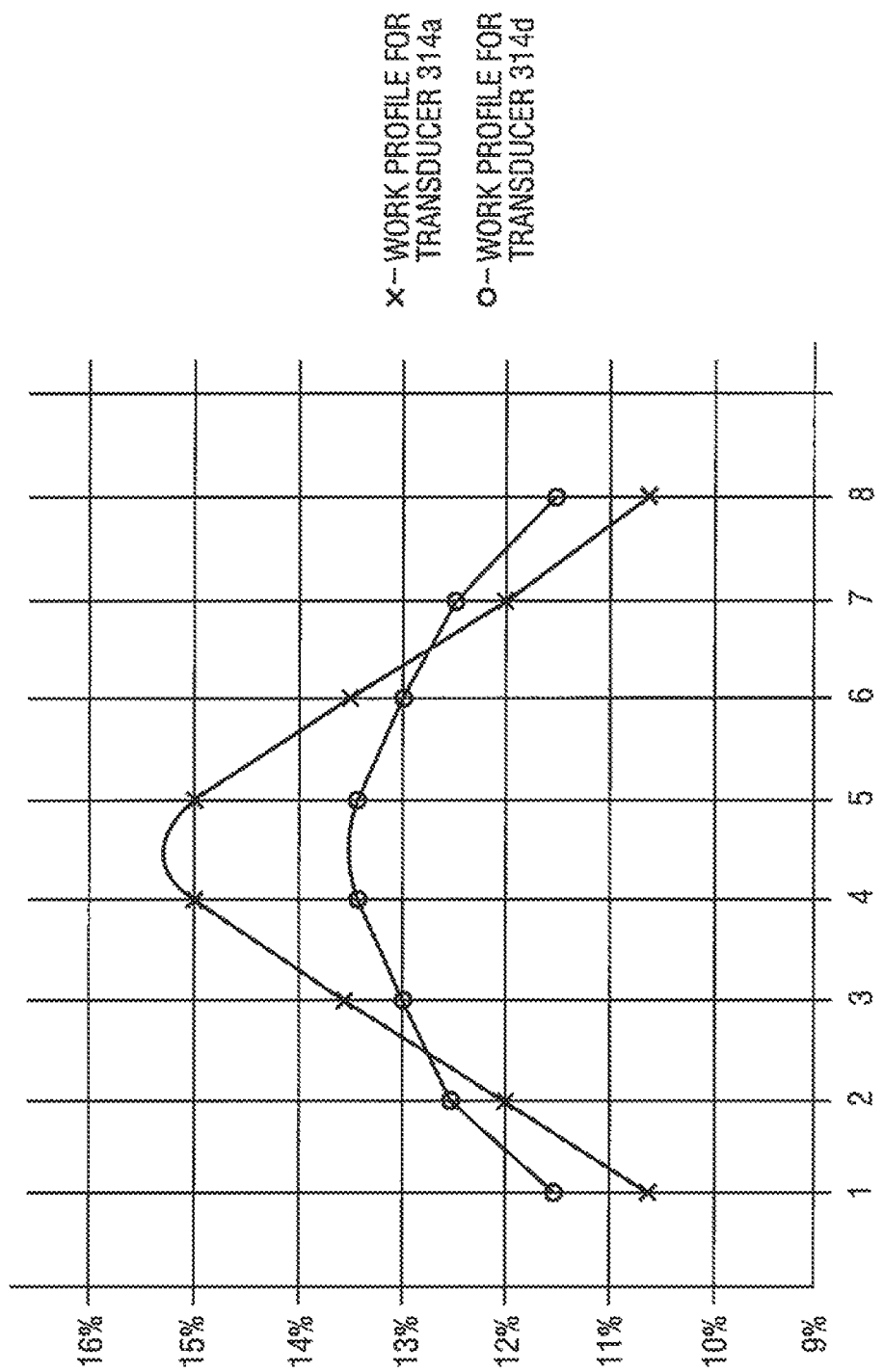
FIG. 14 is a schematic of the work profiles that can be produced by the transducer of FIG. 8 and the transducer of FIG. 11.

In various embodiments, referring now to FIGS. 8-13, piezoelectric elements having different thicknesses can be utilized to distribute the work produced by, and the current drawn by, the piezoelectric elements of a transducer. Referring to FIG. 8, transducer 314a, for example, can comprise four piezoelectric elements 332 having a first thickness and four piezoelectric elements 333 having a second thickness, for example, wherein the second thickness is larger than the first thickness. In such embodiments, piezoelectric elements 332 and 333 can be arranged such that the work produced the piezoelectric elements can generate a work profile as illustrated in FIG. 14. Referring to FIGS. 8 and 14, the thicker piezoelectric elements 333 are positioned closer to node N than the thinner piezoelectric elements 332 wherein, owing to the arrangement of piezoelectric elements 332 and 333 and the longitudinal stress profile 41) generated within the transducer, the work produced by the piezoelectric elements may not be distributed evenly across the piezoelectric elements. In fact, referring to FIG. 14, the work produced by the transducer may be heavily concentrated in the large piezoelectric elements 333 positioned proximate to the node N. Correspondingly, the thinner piezoelectric elements 332 of transducer 314 may produce far less work than piezoelectric elements 333 as they are positioned further away from node N and closer to antinodes AN and, as a result, are subjected to less longitudinal strain.

In various embodiments, referring now to transducers 314b, 314c, 314e, and 314f illustrated in FIGS. 9, 10, 12, and 13, respectively, piezoelectric elements 332 and 333 can be stacked in different arrangements, wherein the different arrangements can produce different work profiles. In various embodiments, further to the above, the piezoelectric elements of a transducer can be arranged such that the work profile produced by the piezoelectric elements is level across the transducer, or at least more closely approximating a level work profile than the work profile produced by transducer 314a, for example. In at least one embodiment, referring now to FIG. 11, transducer 314d, similar to the above, can comprise four piezoelectric elements 332 and four piezoelectric elements 333, for example. In such embodiments, piezoelectric elements 332 and 333 of transducer 314d can be arranged such that the work produced the piezoelectric elements may generate a work profile as illustrated in FIG. 14. More particularly, referring to FIGS. 11 and 14, the thinner piezoelectric elements 332 of transducer 314d are positioned closer to node N than the thicker piezoelectric elements 333 wherein, owing to the arrangement of piezoelectric elements 332 and 333, the work produced by the piezoelectric elements of transducer 314d may be more evenly distributed across the piezoelectric elements. By way of comparison, the large concentration, or peak, of work centralized around node N that may be produced by transducer 314a may be noticeably larger than the less-pronounced concentration of work centralized around node N that may be produced by transducer 314d. Furthermore, by way of comparison, the thicker piezoelectric elements 333 positioned at the ends of the transducer stack of transducer 314d may produce more work than the thinner piezoelectric elements 332 positioned at the ends of the transducer stack of transducer 314a, thereby further leveling the work profile of transducer 314d.

While it is possible that the work profiles illustrated in FIG. 14 may represent the actual work profiles of various transducers, such work profiles have been provided for the purposes of demonstration and discussion. Various other work profiles may be possible. Referring to FIG. 14, the reader will note that the horizontal axis is marked with the numbers 1-8 which represent the eight piezoelectric elements of the exemplary embodiments of transducers 314a and 314d, for example. More particularly, the number 1 may represent the first, or most proximal, piezoelectric element, the number 2 may represent the second, or second-most proximal, piezoelectric element, and so forth. The reader will also note that the vertical axis is marked with percentage values. Such percentage values represent the current that a particular piezoelectric element may draw as compared to the total current drawn by the transducer. For example, the first piezoelectric element of transducer 314a may draw approximately 10.5% of the total current drawn by transducer 314a while the first piezoelectric element of transducer 314d may draw approximately 11.5% of the total current drawn by transducer 314d. In various embodiments, in view of the above, if the percentages of current drawn by each piezoelectric element of transducer 314a were summed, the result should total 100%. Similarly, the percentages of the current drawn by each piezoelectric element of transducer 314d, when summed, should also total 100%.

In various embodiments, as outlined above, the longitudinal strain profile produced by the standing wave of vibrations within a transducer can be sinusoidal, wherein the longitudinal strain can vary in a non-linear or geometric manner between first and second values. In certain embodiments, referring once again to FIG. 8, the strain profile ε(l) within transducer 314a can be represented by a half-sine wave extending between two antinodes AN of the standing wave of vibrations, for example, although other embodiments are envisioned in which any suitable number of antinodes can be located within a transducer. Alternatively, embodiments are envisioned in which no antinodes are located within a transducer. In any event, as also outlined above, the maximum longitudinal strain of the strain profile ε(l) can occur at the node N of the standing wave of vibrations, wherein the piezoelectric elements positioned closest to node N, such as piezoelectric elements $333_3$ and $333_4$ of transducer 314a, for example, can be subjected to the most longitudinal strain. For example, referring to FIG. 8, piezoelectric elements $333_3$ and $333_4$ are positioned just to the left of, or proximal with respect to, node N, wherein the element $333_4$ is subjected to a longitudinal strain $\varepsilon_4$ and the element $333_3$ is subjected to a longitudinal strain $\varepsilon_3$, wherein strain $\varepsilon_4$ is less than $\varepsilon_{max}$, and wherein strain $\varepsilon_3$ is less than strain $\varepsilon_4$. For the purposes of this example, longitudinal strain $\varepsilon_4$ can represent the average strain across piezoelectric element $333_4$ and longitudinal strain $\varepsilon_3$ can represent the average strain across piezoelectric element $333_3$. Correspondingly, referring again to FIG. 8, longitudinal strain $\varepsilon_3$ and longitudinal strain $\varepsilon_4$ are illustrated as occurring in the center of the piezoelectric elements $333_3$ and $333_4$, respectively. In any event, further to the above, strain $\varepsilon_3$ and strain $\varepsilon_4$ may allow piezoelectric elements $333_3$ and $333_4$ to contribute larger quantities of work than the piezoelectric elements $332_2$ and $332_1$ positioned proximally with respect to piezoelectric elements $333_3$ and $333_4$, wherein piezoelectric elements $332_2$ and $332_1$ are subjected to longitudinal strain ε2 and longitudinal strain ε1, respectively. Similar to the above, strains $\varepsilon_2$ and $\varepsilon_1$ can represent the average longitudinal strains experienced across piezoelectric elements $332_2$ and $332_1$, for example.

Further to the above, referring again to FIG. 8, longitudinal strain $\varepsilon_2$ is less than longitudinal strain $\varepsilon_3$ and, in addition, longitudinal strain $\varepsilon_1$ is less than strain $\varepsilon_2$ and significantly less than strain $\varepsilon_4$. Such a relationship is due to the sinusoidal nature, or shape, of the strain profile ε(l). Owing to such a shape, more particularly, the longitudinal strain induced within the transducer can decrease in a geometric, or non-linear, manner with respect to node N and, as a result, the strain profile within the transducer can experience larger changes in longitudinal strain at locations further away from node N, and/or locations closer to an antinode AN. As a result, piezoelectric elements positioned further away from the node N may be subjected to significantly less longitudinal strain and may be less capable of producing larger quantities of work. In order to better balance the work distribution of the piezoelectric elements of a transducer, referring once again to FIG. 11, the piezoelectric elements can be arranged such that the differences in average longitudinal strain experienced across the piezoelectric elements can be reduced. In at least one comparative example, referring to FIGS. 8 and 11, the piezoelectric elements of transducer 314d can be arranged such that the distance B/1 between the node N and the center of piezoelectric element $333_1$ of transducer 314d is less than the distance A/1 between the node N and the center of piezoelectric element $332_1$ of transducer 314a. Owing to the fact that distance B/1 is shorter than distance A/1, the average longitudinal strain experienced within, and the work produced by, piezoelectric element $333_1$ of transducer 314d may be greater than the average strain experienced within, and the work produced by, piezoelectric element $332_1$ of transducer 314a. Owing to the increase in work that piezoelectric element $333_1$ of transducer 314d can provide, the difference in work produced by piezoelectric element $333_1$ and piezoelectric element 3324 of transducer 314d can be less than the difference in work produced by piezoelectric elements $332_1$ and piezoelectric element $333_4$ of transducer 314a, for example.

Figure 11:
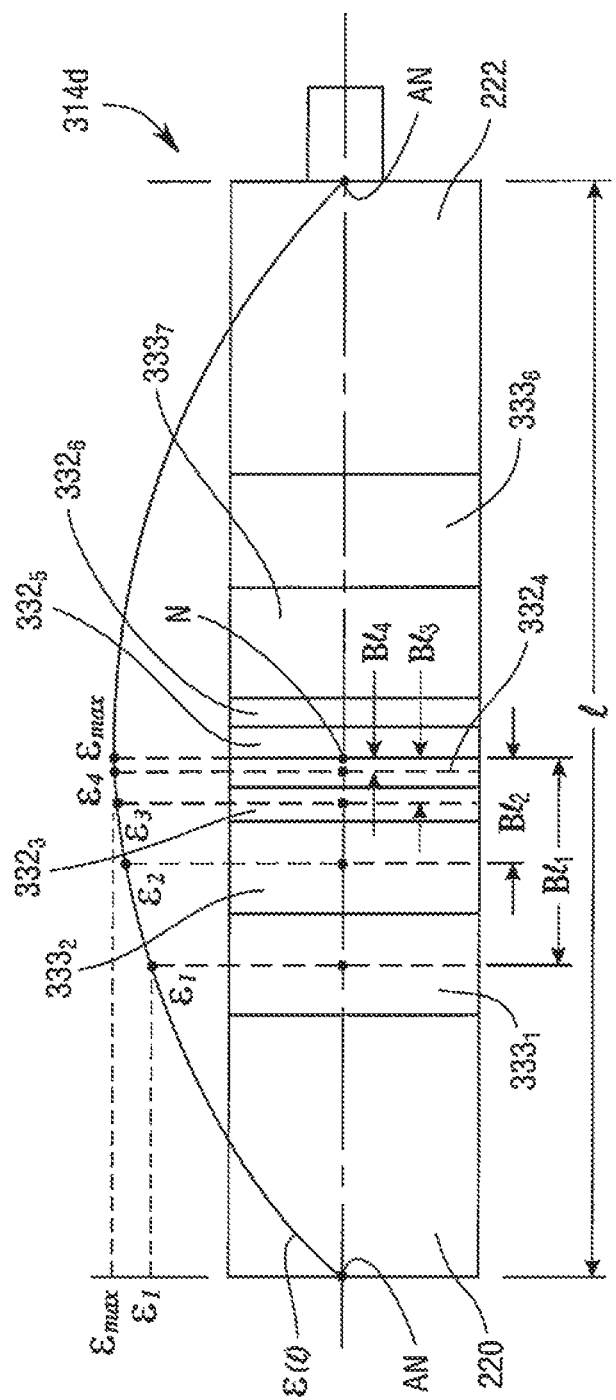
FIG. 11 illustrates a fourth embodiment of a transducer comprising piezoelectric elements having different thicknesses.
Figure 12:
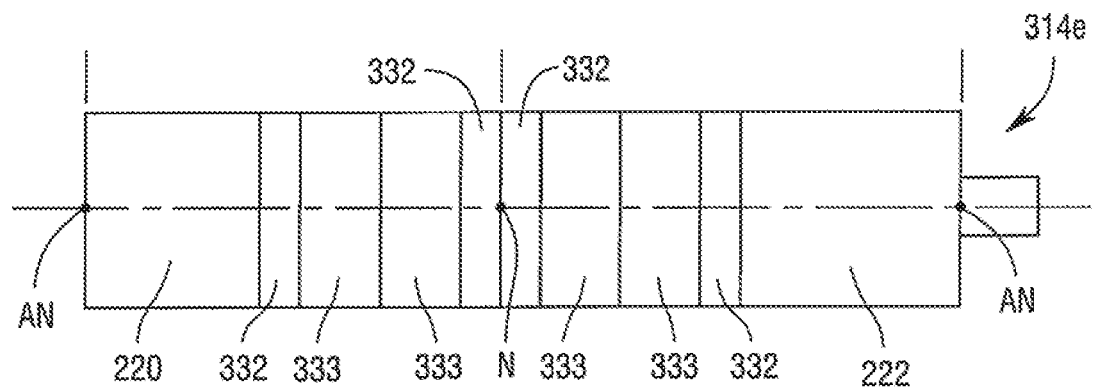
FIG. 12 illustrates a fifth embodiment of a transducer comprising piezoelectric elements having different thicknesses.
Figure 13:
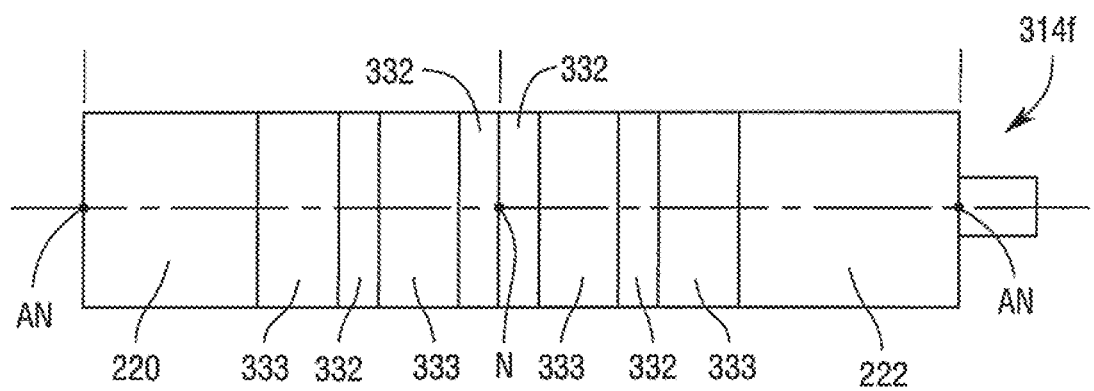
FIG. 13 illustrates a sixth embodiment of a transducer comprising piezoelectric elements having different thicknesses.

Further to the above, referring again to FIGS. 8 and 11, the distance B/2 between the node N and the center of piezoelectric element 3332 of transducer 314d is less than the distance A/2 between the node N and the center of piezoelectric element $332_2$ of transducer 314a. Owing to the fact that distance B/2 is shorter than distance A/2, similar to the above, the average strain experienced within, and work produced by, piezoelectric element 3332 of transducer 314d may be greater than the average strain experienced within, and the work produced by, piezoelectric element $332_2$ of transducer 314a. Owing to the increase in work that piezoelectric element 3332 of transducer 314d can provide, similar to the above, the difference in work produced by piezoelectric element 3332 and piezoelectric element 3324 of transducer 314d can be less than the difference in work produced by piezoelectric elements $332_2$ and piezoelectric element $333_4$ of transducer 314a, for example. Similarly, distance B/3 can be shorter than distance A/3 with regard to the third piezoelectric element and, in addition, distance B/4 can be shorter than distance A/4 with regard to the fourth piezoelectric element, i.e., the element positioned closest to node N. As illustrated in FIGS. 8 and 11, the other piezoelectric elements of transducers 314a and 314d, i.e., elements 3335, 3336, 3327, and 3328 of transducer 314a and elements 3325, 3326, 3337, and 3338 of transducer 314d, can be arranged in a corresponding, or mirror-image, manner, wherein the above-provided discussion is adaptable with respect to these elements with regard to node N and the second, or opposite, antinode AN. In any event, referring once again to FIG. 14, the work produced by the piezoelectric elements across the transducer can be leveled, or at least more closely leveled, by arranging the piezoelectric elements such that the average strain that each element is subjected to is the same, or closer to being same.

In various embodiments, further to the above, piezoelectric elements which are subjected to larger average longitudinal strains can produce larger amplitudes of longitudinal vibrations, especially in thicker piezoelectric elements, i.e., piezoelectric elements which are thicker in the longitudinal direction. In various circumstances, the longitudinal strain of a piezoelectric element can be defined as the change in thickness (Δt) of the piezoelectric element divided by its original, or unenergized, thickness (to) and, when the longitudinal strain within the piezoelectric element is dictated by the generated strain field within a resonating transducer, the utilization of thicker piezoelectric elements may demand that larger longitudinal displacements occur within the piezoelectric elements in order for the relative ratio of (Δt/$t_o$) to be maintained. Stated another way, for a given longitudinal strain value, a larger ($t_o$) may dictate a larger Δt and, correspondingly, a smaller ($t_o$) may dictate a smaller Δt. As outlined above, referring again to FIG. 11, the thicker piezoelectric elements 333 of transducer 314d are positioned further away from node N than piezoelectric elements 332 and, although the thicker elements 333 may be subjected to a smaller average strains than the thinner elements 332, the thickness of piezoelectric elements 333 may compensate for the smaller average strains and may still provide sufficient longitudinal displacements, or vibrations, and produce sufficient quantities of work such that the work profile produced by transducer 314d is level, or at least closer to being level. Although not illustrated, various piezoelectric elements can be used within a transducer wherein the piezoelectric elements can have a variety of different thicknesses, and wherein, in certain embodiments, a transducer can comprise piezoelectric elements having three or more different thicknesses. In certain embodiments, also not illustrated, a transducer can comprise piezoelectric elements wherein the thickest piezoelectric elements are positioned on the ends of the transducer stack, the thinnest piezoelectric elements are positioned in the middle of the stack, and piezoelectric elements having an intermediate thickness are positioned therebetween such that the thicknesses of these piezoelectric elements are arranged in a descending order towards the middle of the stack, for example.

Figure 15:
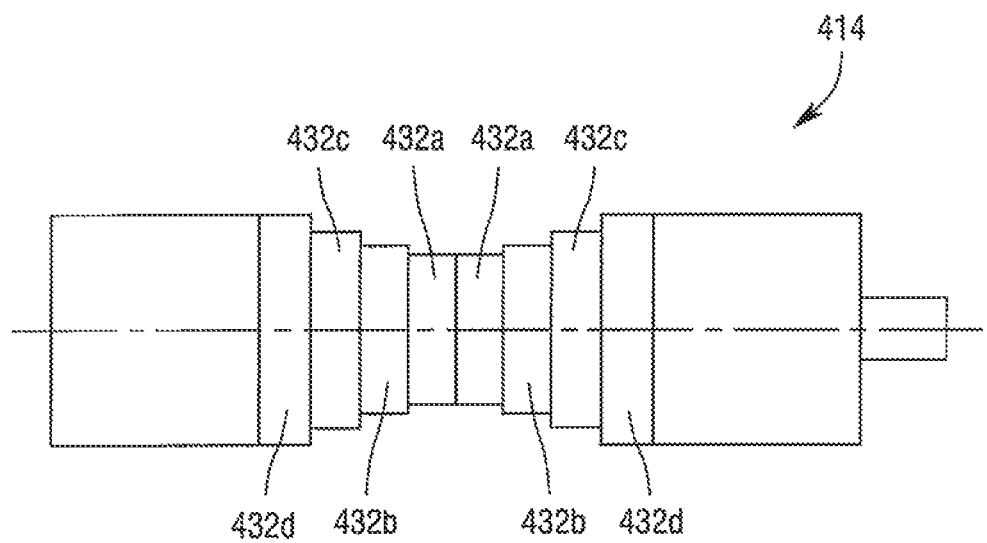
FIG. 15 illustrates an embodiment of a transducer comprising piezoelectric elements having different diameters.

Further to the above, referring again to FIGS. 8-13, the piezoelectric elements of a transducer can have the same, or at least substantially the same, width, height, and/or diameter. In certain other embodiments, referring now to FIG. 15, a transducer, such as transducer 414, for example, can comprise piezoelectric elements having different widths, heights, and/or diameters. More particularly, in at least one embodiment, transducer 414 can comprise first piezoelectric elements 432a having a first diameter, second piezoelectric elements 432b having a second diameter, third piezoelectric elements 432c having a third diameter, and fourth piezoelectric elements 432d having a fourth diameter. In such embodiments, the first, second, third, and/or fourth piezoelectric elements can have different capacitances owing to their different diameters. More particularly, as discussed above, each piezoelectric element can comprise electrodes placed on the opposite sides of the piezoelectric element in order to generate a voltage, or electric, potential across the element, wherein, owing to the directly proportional relationship between the surface area of the electrodes and the potential capacitance of a piezoelectric element, piezoelectric elements having larger diameters can comprise electrodes having larger surface areas and, thus, can generate larger capacitances within the larger piezoelectric elements. In various circumstances, the directly proportional relationship between the surface area of the electrodes and the capacitance of the piezoelectric element can be linear, or at least substantially linear, although embodiments having a geometric relationship are contemplated. Furthermore, owing to the directly proportional relationship between the capacitance of a piezoelectric element and the current flowing through the piezoelectric element, the larger piezoelectric elements having larger capacitances can draw larger currents and, thus, perform larger quantities of work. In various circumstances, the directly proportional relationship between the capacitance and the current flowing through the piezoelectric element can be linear, or at least substantially linear, although embodiments having a geometric relationship are contemplated. In certain circumstances, the capacitance of a piezoelectric element can be represented by the relationship provided below:

$$C = (K^* \varepsilon_0 * A)/t$$

wherein K represents the dielectric constant of the piezoelectric element material, wherein $\varepsilon_0$ represents the permittivity of air, wherein A represents the surface area of the electrodes, and wherein t represents the thickness of the piezoelectric element between the electrodes.

Figure 16:
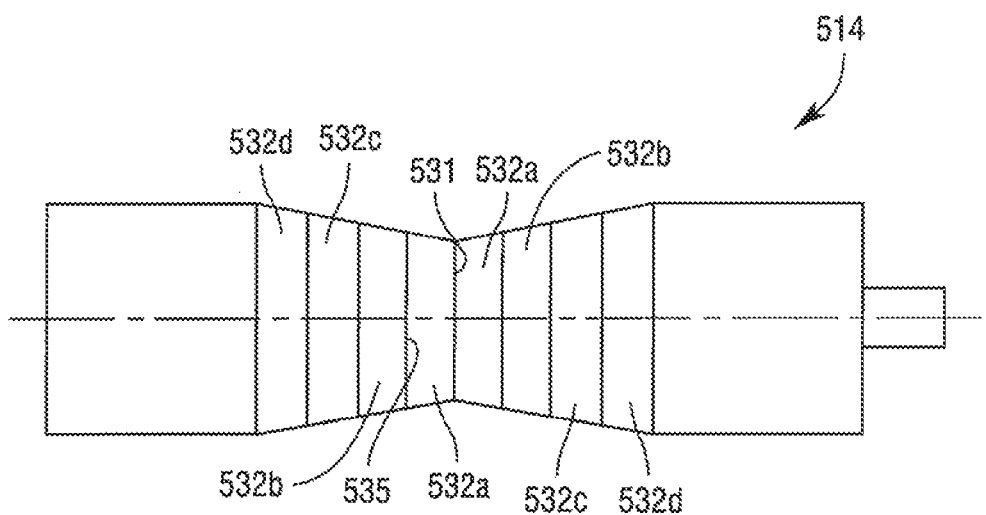
FIG. 16 illustrates a second embodiment of a transducer comprising piezoelectric elements having different diameters.

Referring once again to FIG. 15, the diameter of piezoelectric elements 432a of transducer 414 can be constant, or at least substantially constant, across the thickness thereof. Similarly, the diameters of piezoelectric elements 432b, 432c, and/or 432d can be constant, or at least substantially constant, across the thicknesses thereof. In at least one embodiment, such piezoelectric elements can comprise first and second electrodes which are positioned on opposite sides thereof which have the same, or at least substantially the same, diameter. In various alternative embodiments, the diameter of one or more piezoelectric elements of a transducer may not be constant across the thickness thereof. In at least one such embodiment, referring now to FIG. 16, transducer 514 can comprise a piezoelectric element 532a, for example, which can comprise a first diameter 531 and a second diameter 535, wherein the second diameter 535 can be larger than the first diameter 531. As illustrated in FIG. 16, the diameter of piezoelectric element 532a can decrease between the larger second diameter 535 and the smaller first diameter 531. In various embodiments, the diameter of piezoelectric element 532a can decrease in a linear, or an at least substantially linear, manner, although other changes in diameter are contemplated, such as non-linear or geometric decreases, for example.

Figure 16A:
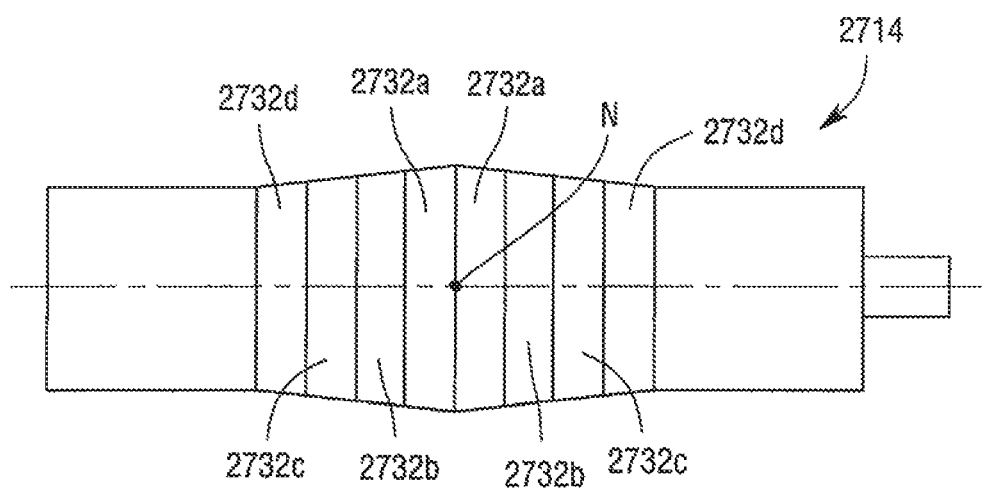
FIG. 16A illustrates a third embodiment of a transducer comprising piezoelectric elements having different diameters.

Further to the above, first and second electrodes can be attached to the sides of piezoelectric elements 532a, wherein the first electrode can have the same diameter, or at least substantially the same diameter, as first diameter 531, and wherein the second electrode can have the same diameter, or at least substantially the same diameter, as second diameter 535. Owing to the different diameters and/or areas, A, of the first and second electrodes, in various embodiments, the capacitance, C, of piezoelectric element 532a can be such that the work produced by piezoelectric element 532a is consistent with a desired work profile. In certain embodiments, transducer 514 can further comprise piezoelectric elements 532b, 532c, and/or 532d, wherein the diameters of these piezoelectric elements can also decrease between first and second diameters. In at least one embodiment, referring again to FIG. 16, the diameters of the piezoelectric elements of transducer 514 can decrease at a constant, or at least substantially constant, rate between the largest diameters of piezoelectric elements 532d and the smallest diameters of piezoelectric elements 532a. In various embodiments, referring now to FIG. 16A, the diameters of the piezoelectric elements of transducer 2714 can increase at a constant, or at least substantially constant, rate between the smallest diameters of piezoelectric elements 2732d and the largest diameters of piezoelectric elements 2732a. Although not illustrated, other embodiments are envisioned in which the diameters of the piezoelectric elements increase and/or decrease in a non-linear manner and/or have any other suitable profile. In any event, similar to the above, the larger and smaller diameters of piezoelectric elements 532a, 532b, 532c, and/or 532d can be arranged such the capacitances, C, of the piezoelectric elements result in a desired work profile. More particularly, as outlined above, larger electrodes can be associated with the larger diameters of the piezoelectric elements as compared to the smaller electrodes associated with the smaller diameters, wherein the larger electrodes can be positioned closer to an antinode AN and, as a result, can provide for a more even distribution of work across the work profile. In various other embodiments, referring again to FIG. 16A, the largest diameters of piezoelectric elements 2732a, 2732b, 2732c, and 2732d can be positioned closer to a node so as to capitalize on larger strain values within the strain profile.

Figure 17:
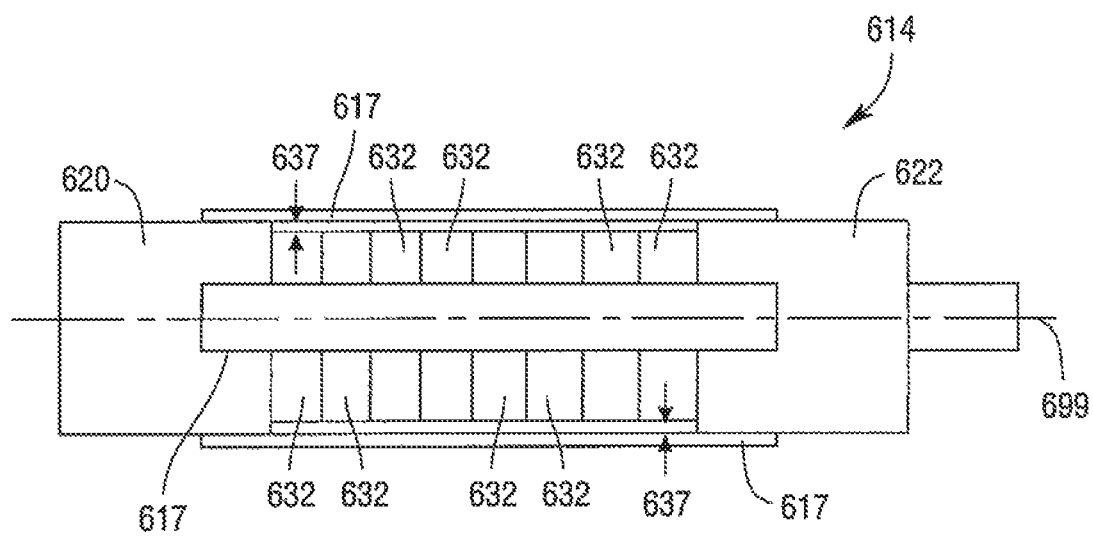
FIG. 17 illustrates an embodiment of a transducer comprising piezoelectric elements and deflectable straps configured to cool the piezoelectric elements.
Figure 18:
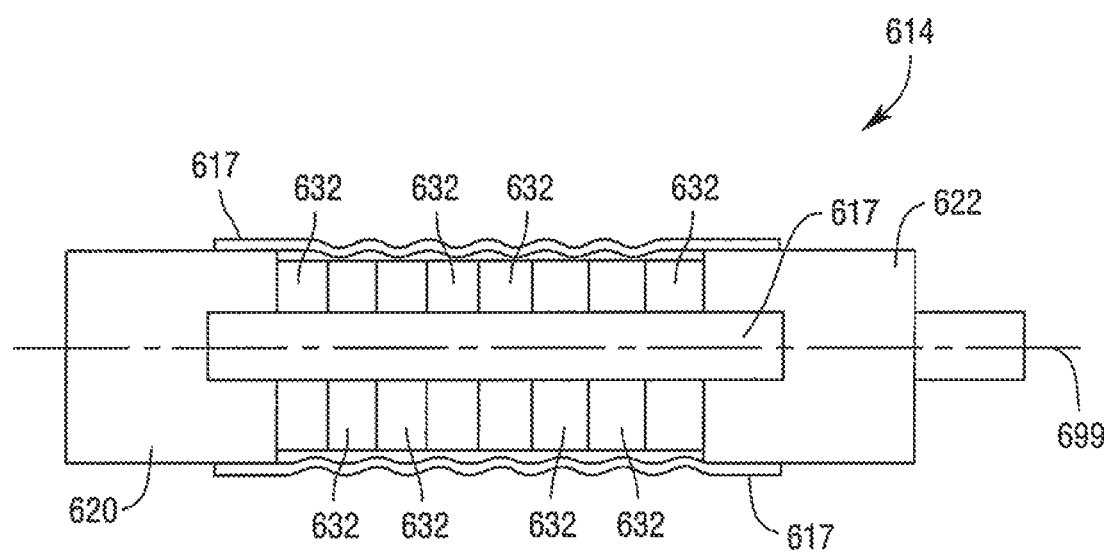
FIG. 18 illustrates the deflectable straps of FIG. 17 being deflected by vibrations produced by the piezoelectric elements.

In various embodiments, as outlined above, the piezoelectric elements of a transducer can generate heat, wherein, in some circumstances, excessive heat may affect the performance of the piezoelectric elements. In certain embodiments, a transducer can comprise a pump. Referring to FIGS. 17 and 18, transducer 614 can comprise one or more straps, or ribbons, 617 which can be configured to pump air around one or more piezoelectric elements 632 of transducer 614 when transducer 614 is actuated as also outlined above. In at least one such embodiment, piezoelectric elements 632 can be positioned intermediate end-bell 620 and fore-bell 622, wherein, although not illustrated in FIG. 17, end-bell 620 and fore-bell 622 can be fastened together so as to capture and/or compress piezoelectric elements 632 therebetween. In certain circumstances, one or more straps 617 can be mounted to end-bell 620 and fore-bell 622 wherein, in at least one embodiment, straps 617 can be mounted to end-bell 620 and fore-bell 622 after end-bell 620 and fore-bell 622 have been bolted together. In at least one embodiment, transducer 614 can comprise four straps 617 which can be welded, and/or otherwise suitably fastened, to end-bell 620 and fore-bell 622, wherein the straps 617 can be positioned equidistantly, or at least substantially equidistantly, around the perimeter of the transducer. Although straps 617 are illustrated as being rectangular and having a constant thickness, straps 617 can have any suitable shape and/or a non-constant thickness. In various embodiments, referring to FIG. 17, gaps 637 can be defined between straps 617 and piezoelectric elements 632 such that, when straps 617 deflect, as described in greater detail below, straps 617 do not contact piezoelectric elements 632.

In various circumstances, referring to FIG. 18, the vibrations produced by piezoelectric elements 632 can cause straps 617 to vibrate and deflect. The deflections of straps 617 can displace the air surrounding straps 617, such as the air located intermediate straps 617 and piezoelectric elements 632, for example, and cause the air to flow over the piezoelectric elements. In various circumstances, the air flowing over the piezoelectric elements 632 can be, at least initially, cooler than the piezoelectric elements 632 such that the air can absorb heat from the piezoelectric elements 632. In certain embodiments, the transducer 614 can be positioned within a handle of a surgical instrument, wherein the handle can include one or more air vents which can allow the warmed air to be exhausted from the handle and allow cooler air to enter the handle and further cool the piezoelectric elements 632. In certain embodiments, a fan having one or more fan blades can be positioned within the handle in order to assist in moving the cooler air around the piezoelectric elements and/or move the heated air out of the handle. In various embodiments, referring again to FIG. 18, straps 617 can be configured to vibrate or deflect in one or more directions. In at least one embodiment, straps 617 can be configured to deflect in a direction which is transverse to longitudinal axis 699 such that straps 617 pump air in a radial, or at least substantially radial, direction over the piezoelectric elements. In certain embodiments, straps 617 can be configured to deflect in directions which are perpendicular, parallel, and/or skew with respect to longitudinal axis 699. In certain embodiments, straps 617 can be configured to produce a laminar flow of air over piezoelectric elements 632, and/or a turbulent flow of air, depending on the geometry and the surface conditions of the piezoelectric elements. In various embodiments, straps 617 can be comprised of metal, such as copper or brass, for example, wherein straps 617 can be configured to conduct heat between end-bell 620 and fore-bell 622. In at least one such embodiment, heat can flow from one end of transducer 614 to the other end such that the heat stored within transducer 614 can be spread evenly, or at least substantially evenly, throughout transducer 614.

Figure 19:
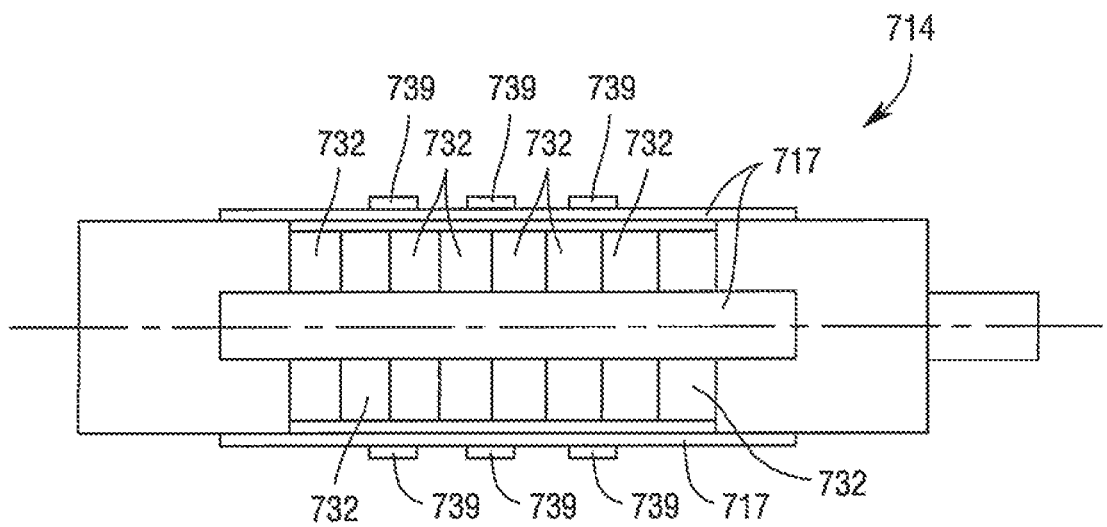
FIG. 19 illustrates an embodiment of a transducer comprising piezoelectric elements, deflectable straps configured to cool the piezoelectric elements, and a plurality of masses mounted to the deflectable straps.

In various embodiments, as outlined above, the piezoelectric elements 626 of transducer 614 can generate longitudinal vibrations which can cause straps, or ribbons, 617 to vibrate and deflect. In certain circumstances, piezoelectric elements 626, for example, can generate vibrations which are transverse or perpendicular to longitudinal axis 699, for example, which can cause straps 617 to vibrate and deflect. In such circumstances, fairly large deflections of straps 617 can occur. In certain embodiments, however, straps 617 may not deflect a sufficient amount to produce a desired air flow. In at least one embodiment, referring now to FIG. 19, one or more weights, or masses, 739 can be mounted to one or more straps 717 which can be configured to cause an eccentricity, or imbalance, within straps 717. Owing to such an imbalance, the vibrations produced by the piezoelectric elements 732 of transducer 714 can be amplified, at least initially, to create larger deflections within straps 717. Stated another way, masses 739 can "kick-off" the deflections of straps 717. In various circumstances, the additional weight of the masses can cause larger deflections of straps 717 throughout the duration in which transducer 714 is operated. In at least one embodiment, masses 739 can comprise, or at least approximate, point masses which do not stiffen, or at least substantially stiffen, straps 717. In any event, each strap 717 can include one or more masses mounted thereto or, in certain other embodiments, some straps 717 can include one or more masses mounted thereto while some straps 717 may not have any straps mounted thereto at all. In certain embodiments, masses 739 can be welded to straps 717 and, in various embodiments, masses 739 can be adhered to and/or fastened to straps 717.

In various embodiments, as outlined above, an ultrasonic surgical instrument can comprise a cable configured to supply current to the transducer of the surgical instrument. In certain embodiments, the cable can be configured to conduct heat away from the transducer and/or a handpiece of the surgical instrument in which the transducer is positioned. In at least one embodiment, the cable can comprise several layers. For example, in at least one such embodiment, a cable can comprise an inner core, an outer core, a first insulative layer positioned intermediate the inner core and the outer core, a second insulative layer surrounding the outer core, a thermally conductive material surrounding the second insulative layer, and an outer insulative layer. The inner core and the outer core can be configured to conduct current to and from the transducer, wherein the first and second insulative layers can be configured to prevent current from leaking therefrom. The thermally conductive material can be configured to draw heat out of the transducer, and/or handpiece, and conduct the heat out of the surgical instrument. In certain circumstances, the conductive material can act as a heat sink and, in at least one embodiment, the conductive material can be comprised of aluminum. In any event, the outer insulative layer can be configured to protect a surgeon, for example, from touching the hot conductive material during use.

Figure 20:
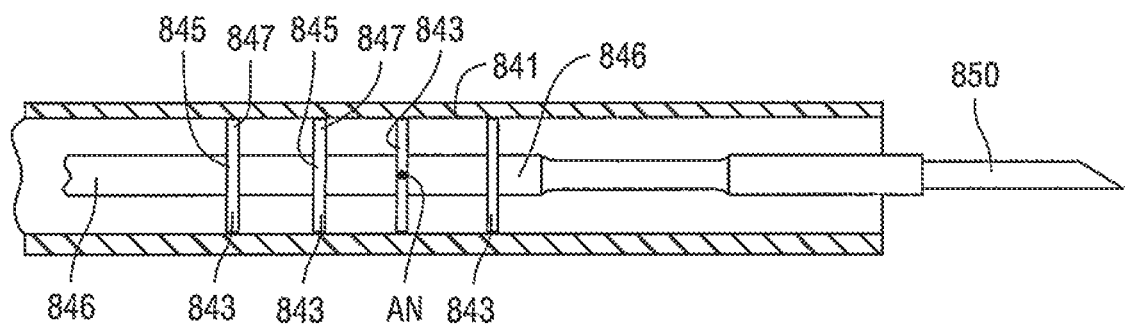
FIG. 20 illustrates an embodiment of a wave guide, an end effector, a sheath, and flexible membranes mounted to the wave guide and the sheath configured to displace air surrounding the wave guide and end effector when the wave guide and end effector are vibrated.
Figure 21:
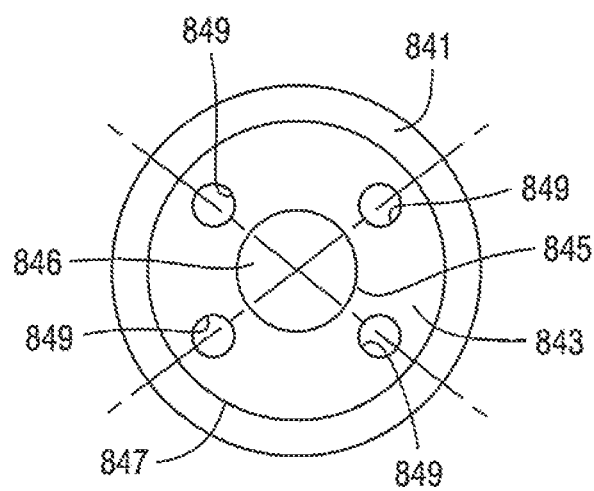
FIG. 21 is an end view of the arrangement of FIG. 20.

In various embodiments, as discussed above, the vibrations produced by a transducer of an ultrasonic instrument can be transmitted to a wave guide, such as wave guide 46, for example, and an end effector, such as end effector 50, for example. Owing to such vibrations, especially when the wave guide and end effector are driven at resonance, the wave guide and end effector may generate and store heat, especially at the nodes of the standing wave of vibrations. In some circumstances, such localized heat generation may be useful. In various circumstances, however, it may be desirable to distribute the heat generated within the wave guide and/or end effector such that the heat is not localized, or at least less localized, in one or more locations. In various embodiments, referring to FIGS. 20 and 21, a surgical instrument can comprise a wave guide 846, an end effector 850, and a sheath, such as 841, for example, which can be configured to surround, or at least partially surround, a portion of wave guide 846 and end effector 850. In certain embodiments, a surgical instrument can comprise a pump configured to move air along a wave guide and/or end effector. In at least one embodiment, the surgical instrument can further include one or more membranes, or diaphragms, extending between sheath 841 and wave guide 846, and/or between sheath 841 and end effector 850. In at least one such embodiment, the surgical instrument can comprise membranes 843 mounted to sheath 841 and wave guide 846, wherein, when wave guide 846 is subjected to vibrations, as outlined above, membranes 843 can move, or pump, air along wave guide 846 and/or end effector 850. More particularly, in at least one embodiment, the center portions 845 of membranes 843 can be affixed to wave guide 846, for example, such that, when wave guide 846 is subjected to longitudinal vibrations, the central portions 845 of membranes 843 can undergo longitudinal excursions while the outer portions 847 of membranes can remain stationary, or at least substantially stationary, as they can be affixed to sheath 841.

Owing to the longitudinal excursions of central portions 845, air positioned intermediate sheath 841 and wave guide 846, for example, can be moved longitudinally along wave guide 846 such that the air can absorb heat generated by and stored within wave guide 846, for example. In certain embodiments, the membranes can produce a laminar and/or turbulent flow of air across the surface of wave guide 846 and end effector 850. In various embodiments, one or more membranes 843 can be positioned at the antinodes of the standing wave of vibrations such that the larger longitudinal displacements of wave guide 846, which occur at the antinodes, can be utilized to produce larger displacements of membranes 843 and larger flows of air. In at least one such embodiment, a membrane can be positioned at each antinode that occurs within a wave guide and an end effector. In various embodiments, the membranes may only be placed at the antinodes while, in other embodiments, several membranes may be positioned in a region surrounding an antinode, for example. In any event, the membranes can further comprise one or more apertures, slots, perforations, and/or openings 849 which can be configured to allow air to flow through the membranes 843, for example. In various embodiments, the membranes can comprise any suitable quantity of apertures, for example, such as one or more apertures, four or more apertures, and/or ten or more apertures, for example. In at least one embodiment, the apertures of one membrane 843, for example, can be aligned with the apertures of adjacent membranes 843. In various embodiments, the outer portions 847 of membranes 843 can be adhered to, and/or otherwise suitably attached to, sheath 841 while the inner portions 845 of membranes 843 can be adhered to, and/or otherwise suitably attached to, wave guide 846. In certain embodiments, the inner portions 845 can comprise a hole which can allow membranes 843 to be slid onto and positioned on wave guide 846. In various embodiments, membranes 843 can be comprised of a polymer material, for example, wherein the material can be thin enough to permit at least a portion of the membrane to move longitudinally while thick enough to withstand repeated movements thereof.

Figure 22A:
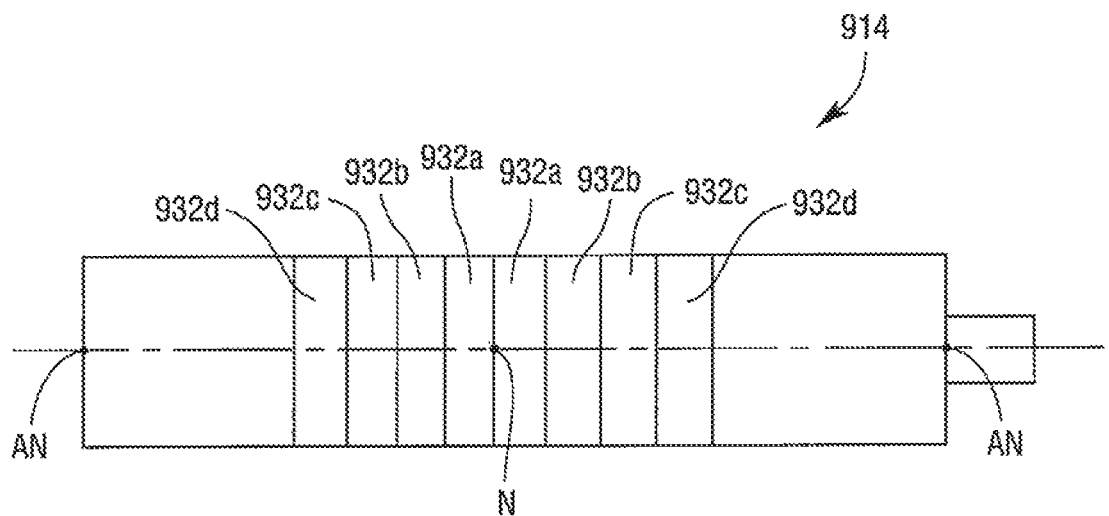
FIG. 22A illustrates an embodiment of a transducer having a first arrangement of piezoelectric elements.
Figure 22B:
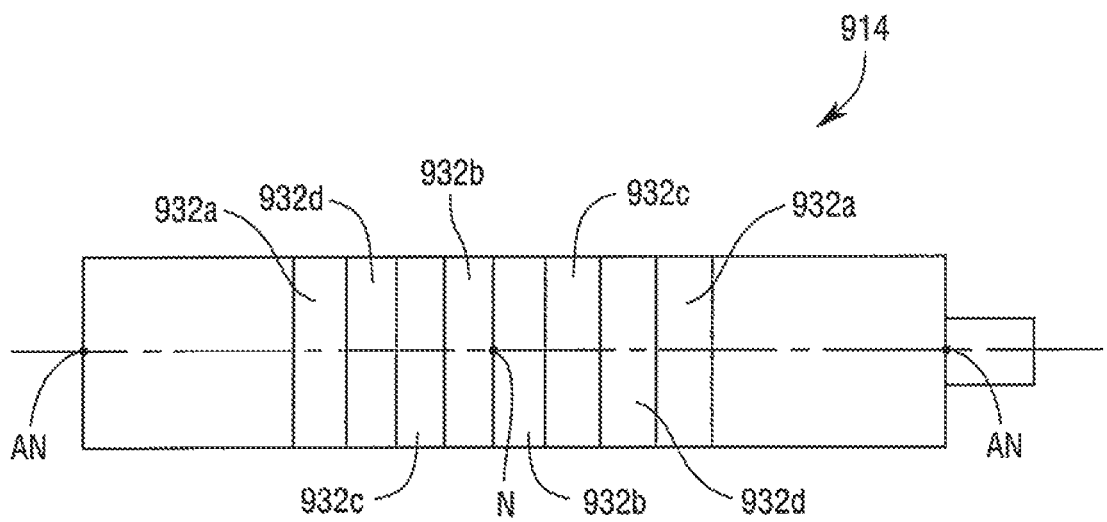
FIG. 22B illustrates the transducer of FIG. 22A having a second arrangement of piezoelectric elements.

In various circumstances, as outlined above, the piezoelectric elements of a transducer positioned closer to a node may be required to perform larger quantities of work and may be subjected to higher temperatures than piezoelectric elements positioned further away from the node. In such circumstances, the piezoelectric elements closest to the node may degrade, and lose their ability to perform a certain amount of work, at a faster rate than the piezoelectric elements positioned further away from the node. When such degradation has occurred in the past, the transducer was discarded. In various embodiments described herein, the transducer can be disassembled after it has been used such that the piezoelectric elements of the transducer can be rearranged. In at least one embodiment, referring to FIG. 22A, a transducer 914 can comprise piezoelectric elements 932a, 932b, 932c, and 932d wherein, in at least the arrangement illustrated in FIG. 22A, piezoelectric elements 932a are positioned closest to the node N and piezoelectric elements 932d are positioned closest to the antinodes AN. After transducer 914 has been used, it may be likely that piezoelectric elements 932a will have degraded more than piezoelectric elements 932b, 932c, and 932d. In certain embodiments, as a result, piezoelectric elements 932a can be shuffled to the ends of the transducer stack and piezoelectric elements 932b, 932c, and 932d can be moved inwardly as illustrated in FIG. 22B. Thereafter, in such embodiments, piezoelectric elements 932b may perform larger quantities of work than piezoelectric elements 932a would have. After transducer 914 has been used once again, transducer 914 can be disassembled such that piezoelectric elements 932b can be shuffled to the ends of the stack, or furthest away from the node, and piezoelectric elements 932c, and 932d can be moved inwardly, or closer to the node. While this particular sequence of reshuffling the piezoelectric elements may be useful, any other suitable sequence may be used.

Figure 23A:
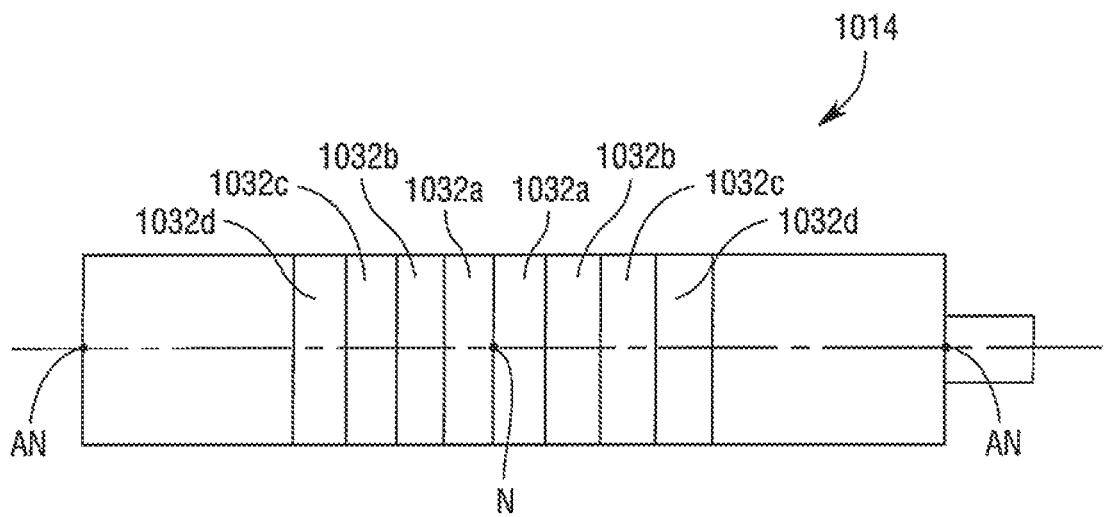
FIG. 23A illustrates an embodiment of a transducer having a first arrangement of piezoelectric elements.

In various embodiments, further to the above, a transducer can be assembled utilizing several piezoelectric elements which have been used more than once or have undergone different duty cycles. In at least one embodiment, referring to FIG. 23A, transducer 1014, for example, can be assembled using first piezoelectric elements 1032a which have undergone a first amount of duty cycles, if any, second piezoelectric elements 1032b which have undergone a second amount of duty cycles, third piezoelectric elements 1032c which have undergone a third amount of duty cycles, and fourth piezoelectric elements 1032d which have undergone a fourth amount of duty cycles. In at least one such embodiment, the first amount of duty cycles can be zero, or at less than the second amount of duty cycles, the second amount of duty cycles can be less than the third amount of duty cycles, and the third amount of duty cycles can be less than the fourth amount of duty cycles. In certain circumstances, as a result, the fourth piezoelectric elements 1032d may be more degraded, or less capable of producing work, than the third piezoelectric elements 1032c, the third piezoelectric elements 1032c can be more degraded than the second piezoelectric elements 1032b, and the second piezoelectric elements 1032b can be more degraded than the first piezoelectric elements 1032a. In such embodiments, the piezoelectric elements having less duty cycles can be positioned closer to a node such that the less-degraded piezoelectric elements can more efficiently contribute to the standing wave of longitudinal vibrations and generate greater quantities of work. Stated another way, further to the above, the largest longitudinal displacements, or vibrations, produced by a transducer are generated by piezoelectric elements positioned at or near a node of the standing wave, wherein the less-degraded piezoelectric elements positioned at or near the node can better capitalize on their position.

Figure 23B:
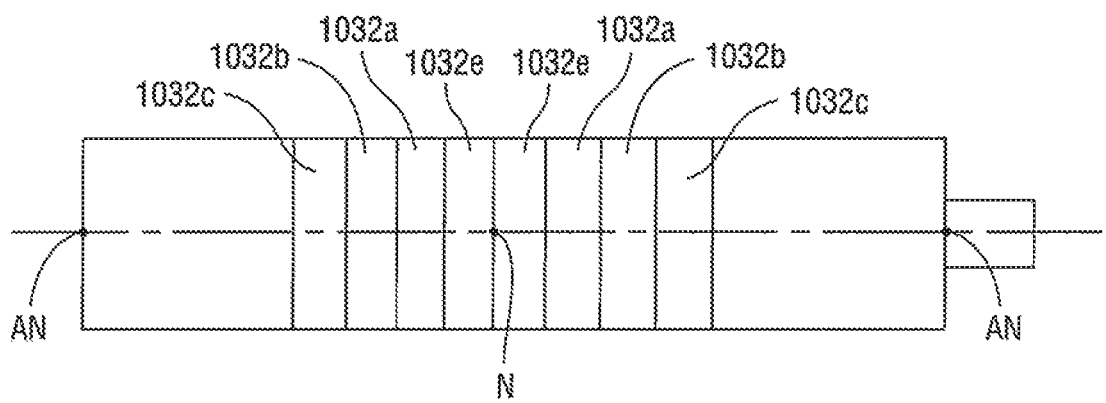
FIG. 23B illustrates the transducer of FIG. 23A having a second arrangement of piezoelectric elements.

After a transducer assembled in accordance with above, such as transducer 1014, for example, has been used, each of the piezoelectric elements, i.e., elements 1032a, 1032b, 1032c, and 1032d, of the transducer will have undergone additional duty cycles and may have become further degraded. In at least one embodiment, as a result, the piezoelectric elements 1032d, which have undergone the most duty cycles at this point, can be removed from the transducer stack. The other remaining piezoelectric elements, i.e., elements 1032a, 1023b, and 1032c can be shifted outwardly within the transducer stack, or repositioned within the transducer stack such that they are positioned further away from the node. In at least one such embodiment, referring now to FIG. 23B, new piezoelectric elements, such as elements 1032e, for example, can be positioned at or nearest to the node. In various embodiments, piezoelectric elements 1032e may have undergone no duty cycles, or may have undergone less duty cycles than piezoelectric elements 1032a, for example. In any event, the transducer can be reassembled and used once again. Thereafter, the transducer can be disassembled once again and new, or at least less-used, piezoelectric elements can be inserted into the stack. Although the insertion of new, or at least less-used, elements into the transducer stack may typically correspond with the removal of a corresponding quantity of piezoelectric elements from the transducer stack, embodiments are envisioned in which new elements can be added to the transducer stack, thereby increasing the total quantity of piezoelectric elements within the stack. Furthermore, although pairs of new, or at least less-used, piezoelectric elements can be replaced within the transducer at a given time, embodiments are envisioned where only one piezoelectric element, or more than two piezoelectric elements, are replaced at a given time.

In various alternative embodiments, further to the above, the piezoelectric elements having more duty cycles within a transducer can be positioned at or nearest to a node while the piezoelectric elements having fewer duty cycles can be positioned further away from the node. In certain embodiments, as the piezoelectric elements having fewer duty cycles may be positioned closer to the antinodes, such piezoelectric elements may be capable of leveling, or at least better leveling, the work produced by the piezoelectric elements. More particularly, as discussed in great detail above, the piezoelectric elements positioned closer to the antinodes of a standing wave of vibrations may undergo less stress and strain and, thus, have less capacity to draw current and produce work and, by having the new, or less-degraded, piezoelectric elements positioned near the antinodes, such piezoelectric elements may be able to compensate for the lesser stress and strain and provide a greater quantity of work than older, or more-degraded, piezoelectric elements would have provided. Similarly, by using the older, or more-degraded, piezoelectric elements closer to the node, such elements may produce a flatter work profile than new, or less-degraded, piezoelectric elements would have provided. In various embodiments, a flatter work profile can be produced which can be beneficial in various circumstances as outlined herein.

As discussed in great detail above, an ultrasonic instrument can comprise a transducer, a wave guide, and an end effector, wherein the transducer can be configured to produce vibrations which causes a system, or assembly, comprising the transducer, the wave guide, and the end effector to vibrate at a resonant frequency. As also discussed above, the resonant frequency of such an assembly may be affected by various mounting or connecting members, for example. In any event, the assembly may be designed to have a particular resonant frequency, such as approximately 55,000 kHz, for example. Owing to various manufacturing differences, however, each assembly may have a slightly different resonant frequency and, as a result, each assembly may be tested in order to find its resonant frequency. If it is determined that the natural frequency of the assembly needs to be adjusted, the end of the wave guide and/or end effector may be ground in order to adjust their length and, as a result, adjust the resonant frequency of the assembly. Although such an assembly process may be useful for its intended purpose, the process may be time consuming and/or may not provide adequate adjustability of the assembly. For example, in the event that too much length is ground off of a wave guide, for example, the wave guide must typically be thrown out and the adjustment process must be repeated with a new wave guide.

Figure 24:
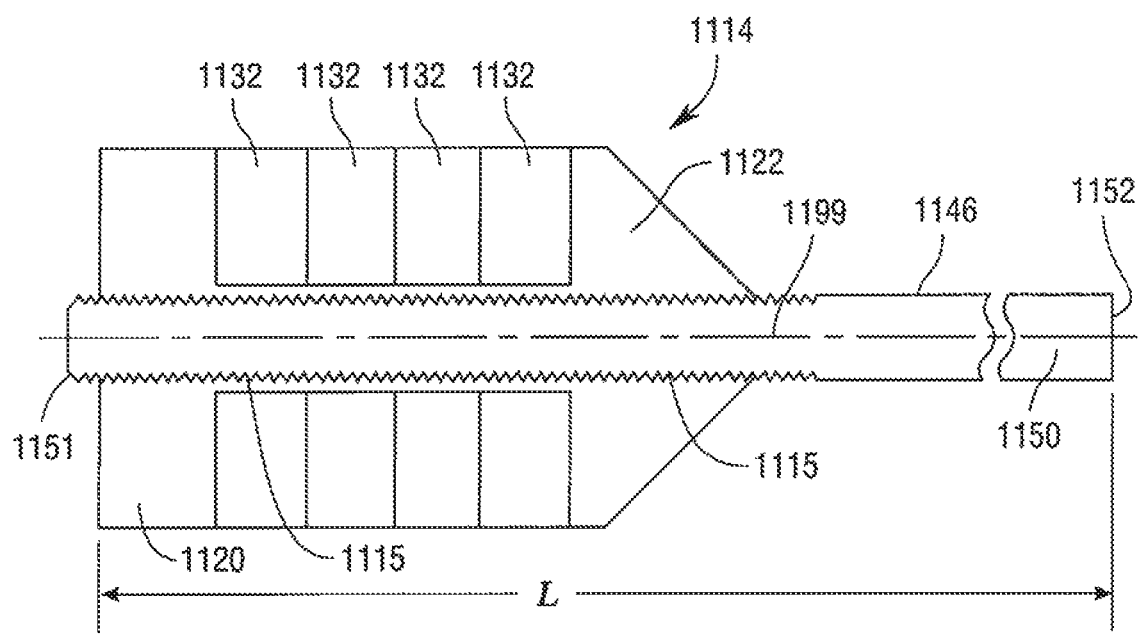
FIG. 24 illustrates an embodiment of a transducer movably adjustable relative to a wave guide.

In various embodiments, referring now to FIG. 24, an ultrasonic instrument can comprise a transducer 1114, a wave guide 1146, and an end effector 1150 which can collectively comprise an assembly having a resonant frequency, wherein wave guide 1146 can be mounted to transducer 1114 such that transducer 1114 can be adjusted relative to wave guide 1146. More particularly, in at least one embodiment, transducer 1114 can comprise a threaded aperture 1115 which can be configured to threadably receive a threaded end 1151 of wave guide 1146 such that wave guide 1146 can be rotated relative to transducer 1114 in order to move wave guide 1146 and end effector 1150 along axis 1199. For example, wave guide 1146 can be rotated in a clockwise direction in order to move the distal end 1152 of end effector 1150 distally with respect to, or away from, transducer 1114. Correspondingly, wave guide 1146 can be rotated in a counter-clockwise direction in order to move distal end 1152 of end effector 1150 proximally, or toward, transducer 1114. In certain embodiments, threaded aperture 1115 can extend between the proximal end of end-bell 1120 and the distal end of fore-bell 1122. In various circumstances, as a result of the above, the length "L" between transducer 1114 and the distal tip 1152 of end effector 1150 can be adjusted in order to tune the resonant frequency of the assembly such that it matches a desired resonant frequency. In at least one embodiment, length "L" can be adjusted such that the distal tip 1152 of end effector 1150 is positioned at, or near, an antinode of the standing wave of longitudinal vibrations and/or such that the center of the transducer stack of piezoelectric elements 1132 is positioned at, or near, a node of the standing wave of longitudinal vibrations.

In any event, once wave guide 1146, end effector 1150, and transducer 1114 have been suitably positioned relative to one another, wave guide 1146 can be immovably affixed to transducer 1114, for example. In at least one embodiment, wave guide 1146 can be welded to end-bell 1120 and/or fore-bell 1122. In certain embodiments, although not illustrated, the assembly can further comprise a connector which can be configured to operably and releasably couple wave guide 1146 to transducer 1114. In at least one such embodiment, the assembly can further comprise one or more compression collars which can be threadably engaged onto end-bell 1120 and/or fore-bell 1122 so as to compress end-bell 1120 and/or fore-bell 1122 against wave guide 1146 and create a friction fit therebetween. In such embodiments, the compression collars can be uncoupled from end-bell 1120 and/or fore-bell 1122 such that the relative position of wave guide 1146 and transducer 1114 can be adjusted once again. In various embodiments, although not illustrated, an ultrasonic assembly can comprise a transducer and a wave guide, and/or end effector, wherein at least a portion of the wave guide can be press-fit into a hole within the transducer. In at least one such embodiment, the position of the wave guide within the transducer hole can be adjusted with sufficient axial force applied thereto even though the wave guide may be immovable relative to the transducer during the course of the ordinary operation of the surgical instrument.

In various embodiments, also not illustrated, an ultrasonic instrument can comprise a transducer having an aperture and, in addition, a wave guide, or end effector, configured to be inserted into the aperture, wherein a thermal interference fit can be created between the wave guide and the sidewalls of the transducer aperture, for example. More particularly, in at least one such embodiment, the transducer aperture and the wave guide can be configured such that the wave guide cannot be inserted into the transducer aperture when the transducer and the wave guide are at the same temperature, or at least substantially the same temperature, although the transducer can be heated such that the aperture expands, and/or the wave guide can be cooled such that it contracts, so that the wave guide can be inserted into the transducer aperture. Owing to such temperature differences, sufficient clearance can exist between the wave guide and the side walls of the transducer aperture such that the position of the wave guide relative to the transducer can be adjusted. After the transducer has been sufficiently cooled, and/or after the wave guide has been sufficiently warmed, an interference fit may exist between the wave guide and the sidewalls of the transducer aperture. Such an interference fit can be referred to as a thermal interference fit. In any event, if it is determined that the position of the wave guide needs to be readjusted, the transducer can be heated and/or the wave guide can be cooled once again in order to permit the wave guide to be moved relative to the transducer once again.

Figure 25:
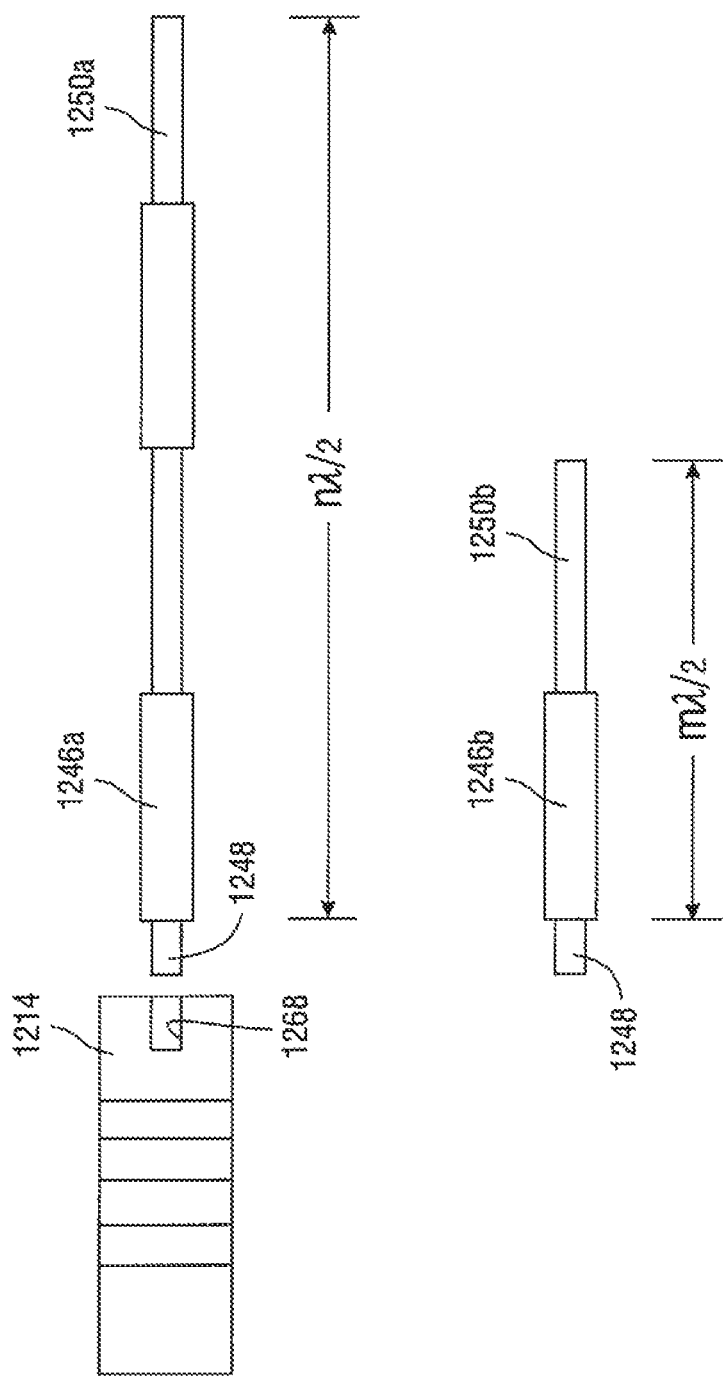
FIG. 25 illustrates a kit for an ultrasonic surgical instrument comprising a plurality of wave guides and end effectors.

In various embodiments, the length and mass of an assembly comprising a transducer, wave guide, and/or end effector can dictate the resonant frequency of the assembly. In various circumstances, the length of the assembly can be selected such that the resonant frequency of the assembly is within a range of frequencies that a voltage or current source can supply to the transducer. In certain embodiments, a given transducer, wave guide, and/or end effector may be required to be used together and, in the event that a different length wave guide or different end effector is needed, a different surgical instrument altogether may be required. In various alternative embodiments, referring now to FIG. 25, a surgical instrument kit can comprise a handpiece comprising a transducer and two or more wave guides and/or two or more end effectors which can be assembled to the transducer in order to allow a surgical instrument to be adapted to have various lengths and/or have various uses. More particularly, in at least one embodiment, a kit can comprise a transducer 1214, an integral first wave guide 1246*a* and first end effector 1250*a*, and an integral second wave guide 1246*b* and second end effector 1250*b*, wherein, in at least one such embodiment, a surgeon can selectively assemble the integral first wave guide 1246*a* and first end effector 1250*a*, and/or the integral second wave guide 1246*b* and second end effector 1250*b*, to transducer 1214 such that the surgical instrument can have different lengths, for example. In various embodiments, the length and mass of the integral first wave guide 1246*a* and end effector 1250*a* can be such that, when they are attached to transducer 1214, the voltage and/or current source can supply power to the transducer 1214 at a first resonant frequency and, similarly, the length and mass of the integral second wave guide 1246*b* and end effector 1250*b* can be such that, when they are attached to transducer 1214, the voltage and/or current source can supply power to the transducer 1214 at a second, or different, resonant frequency. In certain embodiments, the first and second resonant frequencies can be the same, or at least substantially the same. In various embodiments, the transducer 1214 can comprise a threaded aperture 1268 and the wave guides 1246*a* and 1246*b* can each comprise a threaded stud 1248 which can be threadably inserted into the threaded aperture 1268. In certain embodiments, integral wave guide 1246*a* and end effector 1250*a* can comprise a first length which is an integer multiple of one-half of the wavelength of the standing wave of vibrations, i.e., $(n*\lambda)/2$, at the resonant frequency of the assembly. Similarly, in at least one embodiment, the integral wave guide 1246*b* and end effector 1250*b* can comprise a second length which is an integer multiple of one-half of the wavelength of the standing wave of vibrations at the resonant frequency of the assembly, i.e., $(m*\lambda)/2$, wherein m can be less than n, for example. In various embodiments, the lengths of the wave guides and end effectors can be configured such that the tips 1252*a* and 1252*b* of the assemblies, and/or the threaded studs 1248, are positioned at or near an antinode of the standing wave of vibrations.

Figure 26:
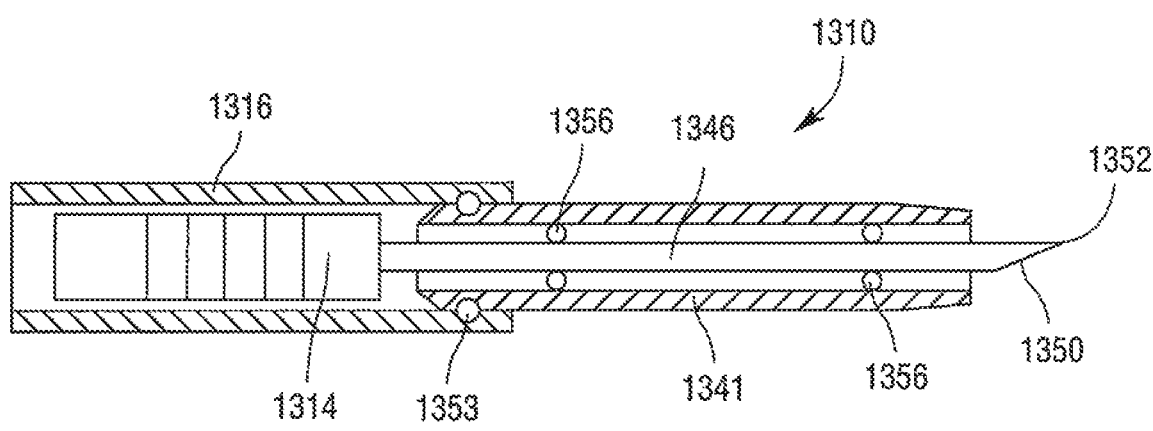
FIG. 26 illustrates an embodiment of an ultrasonic surgical instrument.
Figure 27:
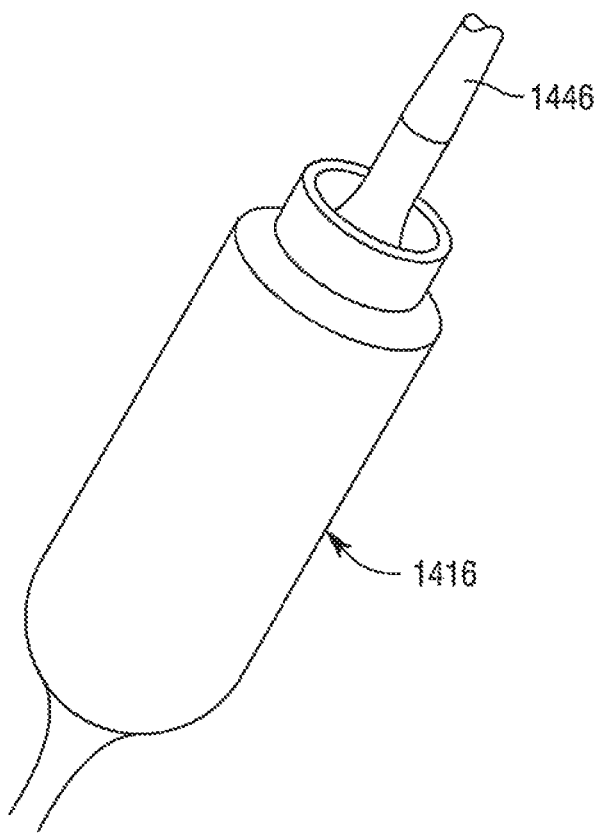
FIG. 27 illustrates a handle of an ultrasonic surgical instrument and a proximal portion of a wave guide, wherein the handle comprises a flexible housing.

In various embodiments, further to the above, an ultrasonic instrument may comprise a transducer, a wave guide, and an end effector, wherein the ultrasonic instrument may further comprise a housing at least partially surrounding the transducer and a sheath at least partially surrounding the wave guide and/or end effector. In at least one embodiment, referring to FIG. 26, ultrasonic surgical instrument 1310 can comprise a transducer 1314, a housing 1316 encompassing transducer 1314, a wave guide 1346, a sheath 1341 encompassing wave guide 1346, and an end effector 1350. In certain embodiments, surgical instrument 1310 can further comprise one or more stabilizing supports 1356 which can be configured to support wave guide 1346 and/or end effector 1350 within sheath 1341. In at least one such embodiment, sheath 1341 can comprise a handle portion and/or can be configured to be grasped, or gripped, by a surgeon such that the surgeon can accurately manipulate surgical instrument 1310 and, in particular, accurately manipulate distal end 1352 of end effector 1350. In at least one embodiment, at least a portion of the outer surface of sheath 1341 can comprise a roughened and/or textured surface. In certain embodiments, the outer surface of sheath 1341 can comprise a round, or at least substantially round, cross-section having a diameter of approximately 5 millimeters, approximately 10 millimeters, approximately 15 millimeters, and/or a diameter between approximately 4 millimeters and approximately 16 millimeters.

In any event, supports 1356 can be sufficiently rigid to transfer forces between sheath 1341 and wave guide 1346 and yet can be sufficiently compliant to permit relative movement between wave guide 1346 and sheath 1341. In certain embodiments, supports 1356 can also dampen vibrations transmitted between wave guide 1346 and sheath 1341, for example. In various embodiments, supports 1356 can be positioned at or near the nodes of the standing wave of longitudinal vibrations, although supports 1356 can be positioned at any suitable location. Supports 1356 positioned at or near the nodes of the longitudinal standing wave of vibrations may undergo smaller displacements and, thus, smaller vibrations may be transmitted to sheath 1341, for example. In any event, transducer housing 1316 can be mounted to sheath 1341 wherein, in various embodiments, housing 1316 can be adhered to, fastened to, and/or otherwise suitably affixed to sheath 1341. In various embodiments, housing 1316 can be mounted to sheath 1341 such that housing 1316 is not in direct contact with transducer 1314. In at least one such embodiment, transducer 1314 and housing 1316 can move, or float, relative to one another. In at least one embodiment, referring again to FIG. 26, surgical instrument 1310 can further comprise one or more compliant supports, such as support 1353, for example, positioned intermediate housing 1316 and sheath 1341, wherein support 1353 can be configured to dampen vibrations transmitted between sheath 1341 and housing 1316. In certain embodiments, support 1353 can comprise an o-ring compressed between sheath 1341 and housing 1316. Owing to such an arrangement, in at least one embodiment, the connection between transducer housing 1316 and sheath 1341 can occur at any suitable location along the length of surgical instrument 1310 with little or no regard to whether such a location is at a node and/or antinode of the standing wave of longitudinal vibrations.

Figure 28:
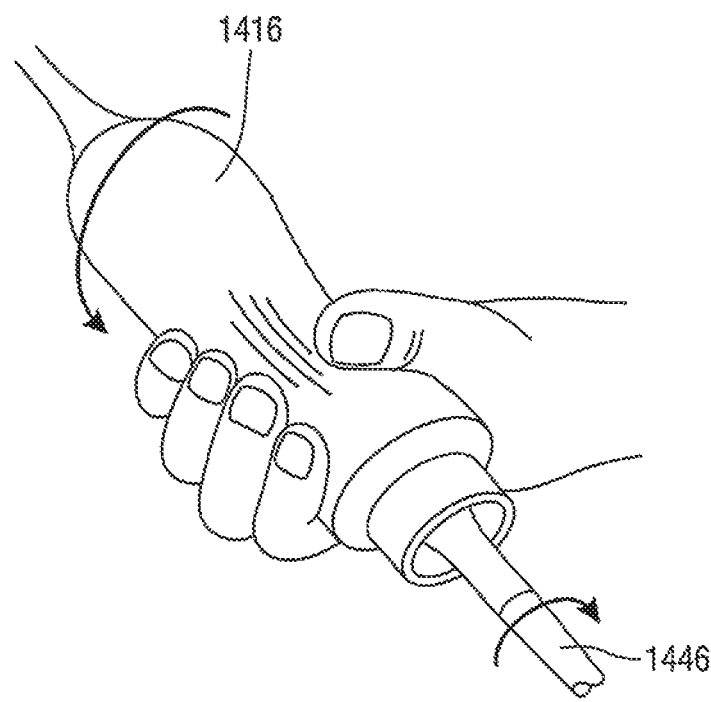
FIG. 28 illustrates the handle of FIG. 27 in a flexed condition.
Figure 29:
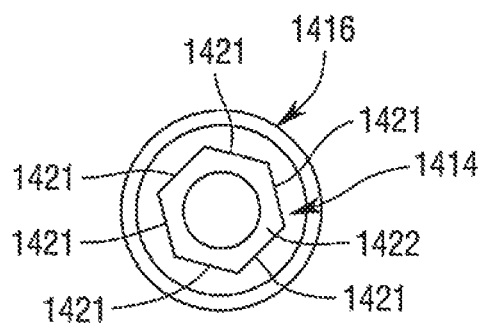
FIG. 29 illustrates an end view of the handle of FIG. 27 in an unflexed condition.
Figure 30:
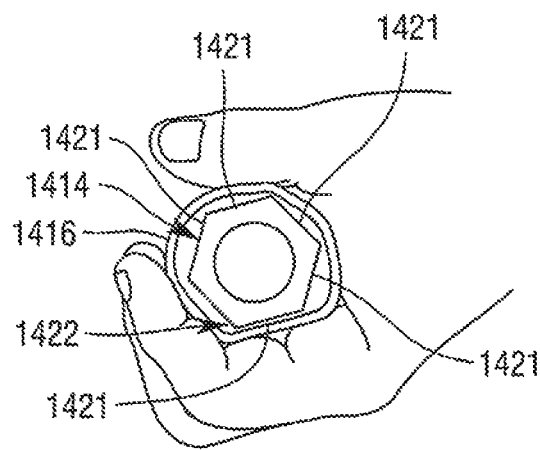
FIG. 30 illustrates an end view of the handle of FIG. 27 in a flexed condition.

In various embodiments, further to the above, a transducer housing, such as transducer housing 1316, for example, can be comprised of a rigid, or at least substantially rigid material, such as plastic, for example. In certain embodiments, a transducer housing can be sufficiently flexible such that it can be deflected, or elastically deformed, between a first configuration, in which the transducer housing does not contact, or at least substantially contact, a transducer positioned therein, and a second position in which the transducer housing contacts the transducer. In at least one embodiment, referring now to FIGS. 27-30, an ultrasonic surgical instrument can comprise a transducer 1414, a transducer housing 1416 at least partially surrounding transducer 1414, and a wave guide 1446 which can be operably coupled with transducer 1414. Similar to the above, although not illustrated in FIGS. 27-30, the surgical instrument can further comprise a sheath at least partially surrounding wave guide 1446, wherein at least a portion of housing 1416 can be mounted to the sheath, for example. In certain embodiments, referring to FIG. 28, a surgeon, or other clinician, can grasp housing 1416 in order to apply a gripping force thereto and deflect it inwardly toward transducer 1414 such that housing 1416 can engage at least a portion of transducer 1414, such as a gripping portion. In such circumstances, the surgeon or clinician can hold transducer 1414 in position via housing 1416 while they mount wave guide 1446 to transducer 1414. More particularly, in at least one embodiment, transducer 1414 can comprise a distal end, or gripping portion, 1422, for example, having one or more flat surfaces, or at least substantially flat surfaces, 1421 which can be easily gripped by the surgeon or clinician while a proximal end of wave guide 1446 is threadably inserted into the transducer, as outlined above. In such circumstances, referring again to FIG. 28, the surgeon or clinician may be able to rotate, or torque, transducer 1414 in a first direction and/or rotate, or torque, wave guide 1446 in a second, or opposite direction, until wave guide 1446 and transducer 1414 are suitably secured together. In other various embodiments, a transducer may comprise grippable features which can allow the surgeon to insert a wave guide into the transducer in an axial, or longitudinal, direction, for example. In any event, in at least one embodiment, the gripping portion 1422, for example, can be located at an anti-node of the standing wave of longitudinal vibrations.

In various embodiments, once the wave guide has been mounted to the transducer, the surgeon or clinician can release housing 1416 such that housing 1416 sufficiently expands and is no longer in contact with transducer 1414. In various embodiments, the housing 1416 can be sufficiently resilient such that it returns to its original shape. Owing to the above, in certain embodiments, the transducer housing may not contact the transducer and, as a result, may not impede or affect the standing wave of vibrations created by the transducer during use. In the event that the surgeon or clinician seeks to detach wave guide 1446 from transducer 1414, they may grip housing 1416 once again and rotate, or torque, the wave guide and transducer in opposite directions. In various embodiments, although not illustrated, a portion of a handle can comprise one or more inwardly extending interlocking features which, when the handle is compressed inwardly towards a transducer, can be configured to engage corresponding interlocking features on the transducer. Such embodiments can provide a keyed arrangement which can facilitate holding the transducer in position when a wave guide or end effector is mounted thereto, for example. Although not illustrated, various alternative embodiments are envisioned in which a flexible housing is mounted to the transducer at least one location, but is flexible inwardly to connect a wave guide or end effector to the transducer as outlined herein.

Figure 31:
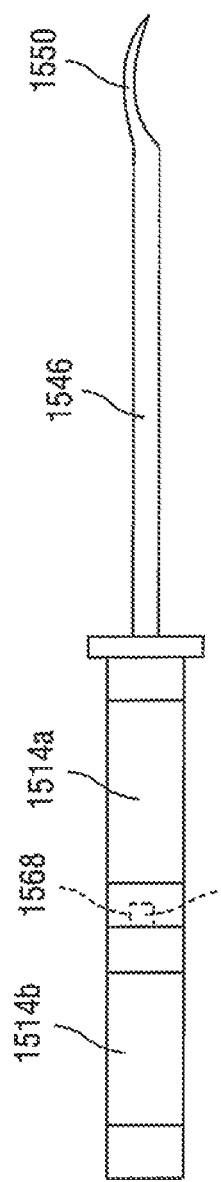
FIG. 31 illustrates an embodiment of a surgical instrument comprising a plurality of transducers.

In various embodiments, as outlined above, the power produced by a transducer of an ultrasonic surgical instrument, and/or the magnitude of the vibrations produced by the transducer, can be proportional the voltage potential applied across the piezoelectric elements of the transducer, for example. While increasing the voltage applied to the piezoelectric elements can increase the power output of the transducer, such a power increase can be met with an undesirable increase in temperatures as outlined above. In certain embodiments, referring now to FIG. 31, a surgical instrument can comprise a wave guide 1546, an end effector 1550, a first transducer 1514a, and a second transducer 1514b, wherein wave guide 1546 can be mounted to first transducer 1514a, and wherein first transducer 1514a can be mounted to second transducer 1514b. In at least one embodiment, similar to the above, one of transducer 1514a and transducer 1514b can comprise a threaded aperture, such as aperture 1568, for example, and the other of transducer 1514a and transducer 1514b can comprise a threaded post, such as post 1548, for example, wherein threaded post 1548 and threaded aperture 1568 can be configured to securely fasten first transducer 1514a and second transducer 1514b together.

In various embodiments, further to the above, the power of an ultrasonic instrument can be increased by the selective attachment of second transducer 1514b to first transducer 1514a, for example. In at least one embodiment, a kit can be provided to a surgeon including a handle, a first transducer, a second transducer, and a wave guide and/or end effector, wherein, if the surgeon desires the surgical instrument to have a first, or lower, power, the surgeon, or other clinician, can insert the first transducer 1514a into the handle and assemble the first transducer 1514a to the wave guide and/or end effector without assembling the second transducer 1514b to the instrument. In certain embodiments, the first transducer 1514a may already be inserted into the handle and may already be operably engaged with the wave guide and/or end effector when the surgeon or other clinician receives the kit. In either event, if the surgeon desires that the surgical instrument should have a second, or larger, power, the surgeon can selectively attach the second transducer 1514*b* to the first transducer 1514*a*, wave guide, and/or end effector. Similar to the above, in certain embodiments, the second transducer 1514*b* may already be preassembled to the first transducer 1514*a* when the surgeon or other clinician receives the kit.

In various embodiments, further to the above, a kit for a surgical instrument can comprise more than two transducers. In at least one embodiment, for example, the kit may comprise a first transducer configured to supply a first quantity of power, a second transducer configured to supply a second quantity of power, and a third transducer configured to supply a third quantity of power, for example. In certain embodiments, a kit may have more than three transducers and, in some embodiments, some of the transducers within the kit can be configured to supply the same, or at least substantially the same, quantity of power. In any event, the surgeon or other clinician can select from the provided transducers in order to arrive at a desired quantity of power that will be supplied to the surgical instrument. In at least one such embodiment, more than two transducers can be assembled together in order to deliver power to the wave guide. In various embodiments, referring again to FIG. 31, the transducers can be affixed to one another in a series arrangement wherein the total deliverable power of the surgical instrument can be determined by summing the deliverable power of each transducer.

In various embodiments, further to the above, an ultrasonic surgical instrument comprising two or more transducers operably coupled to a wave guide and/or end effector of the surgical instrument can be configured such that the transducers produce standing waves of vibrations which overlap, or at least substantially overlap, with one another. In at least one embodiment, a surgical instrument can comprise a first transducer which produces a first standing wave of vibrations within a wave guide and, in addition, a second transducer which produces a second standing wave of vibrations within the wave guide, wherein the nodes and antinodes of the first and second standing waves of vibrations can be coincident, or at least nearly coincident with one another. In at least one such embodiment, the first and second standing waves of vibrations can supplement each other such that the displacements produced by the standing waves are superimposed onto one another and have an additive effect.

Figure 32:
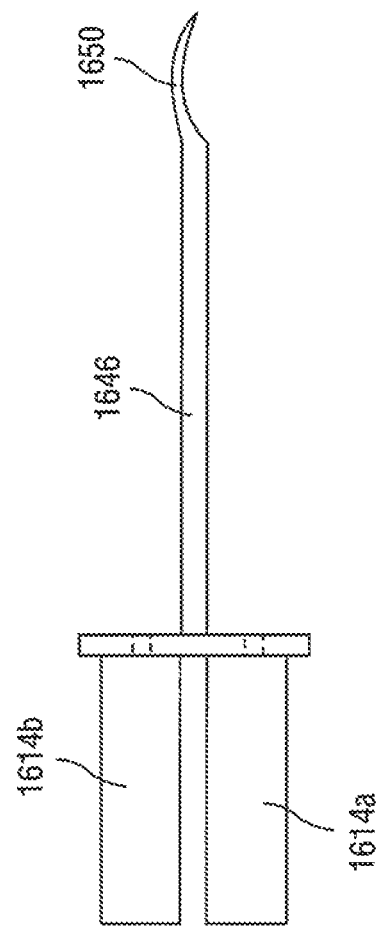
FIG. 32 illustrates a second embodiment of a surgical instrument comprising a plurality of transducers.

In certain embodiments, referring now to FIG. 32, two or more transducers can be mounted to a wave guide and/or end effector of an ultrasonic surgical instrument in a parallel arrangement. More particularly, in at least one embodiment, an ultrasonic surgical instrument can comprise a wave guide 1646, an end effector 1650, a first transducer 1614*a*, and a second transducer 1614*b*, wherein transducers 1614*a* and 1614*b* can both be mounted to a common mounting portion of wave guide 1646. In certain embodiments, similar to the above, the transducers and the wave guide can comprise co-operating threaded apertures and posts which can be utilized to secure the transducers to the wave guide. Also similar to the above, the standing waves of longitudinal vibrations produced by transducers 1614*a* and 1614*b* can supplement each other such that the displacements produced by the standing waves are superimposed onto one another and have an additive effect. In various embodiments, although not illustrated, an ultrasonic surgical instrument can comprise transducers which can be operably engaged with a wave guide and/or end effector in both parallel and series arrangements. For example, first and second transducers can be directly mounted to a wave guide in parallel with one another, wherein a third transducer can be mounted to the first transducer such that it is in series with the first transducer, and wherein a fourth transducer can be mounted to the second transducer such that it is in series with the second transducer, for example.

In various embodiments, further to the above, the first and second transducers of a surgical instrument can be configured such that the center of each of the piezoelectric stacks of the first and second transducers are positioned at, or near, a node of the standing wave of vibrations. In other various embodiments, the first and second transducers of a surgical instrument can be configured such that the center of the piezoelectric stack of the first transducer is positioned at, or near, a node and such that the center of the piezoelectric stack of the second transducer is positioned closer to an antinode. In such embodiments, further to the above, the first piezoelectric stack may be able to contribute more work, and may generate more heat, than the second piezoelectric stack. In at least one such embodiment, as a result, the piezoelectric elements within the first transducer can be different than the piezoelectric elements within the second transducer. More particularly, the piezoelectric elements of the first transducer, i.e., the transducer positioned closer to a node, can be comprised of a material, or materials, which have a higher strain constant, for example, than the materials of the piezoelectric elements of the second transducer. In various embodiments, the piezoelectric elements of the first transducer can be comprised of a material having a higher Curie temperature, for example, than the material of the piezoelectric elements of the second transducer. In certain embodiments, the piezoelectric elements of the first transducer can comprise piezoelectric elements which have undergone a higher, or lower, quantity of duty cycles than the piezoelectric elements of the second transducer.

Figure 1A:
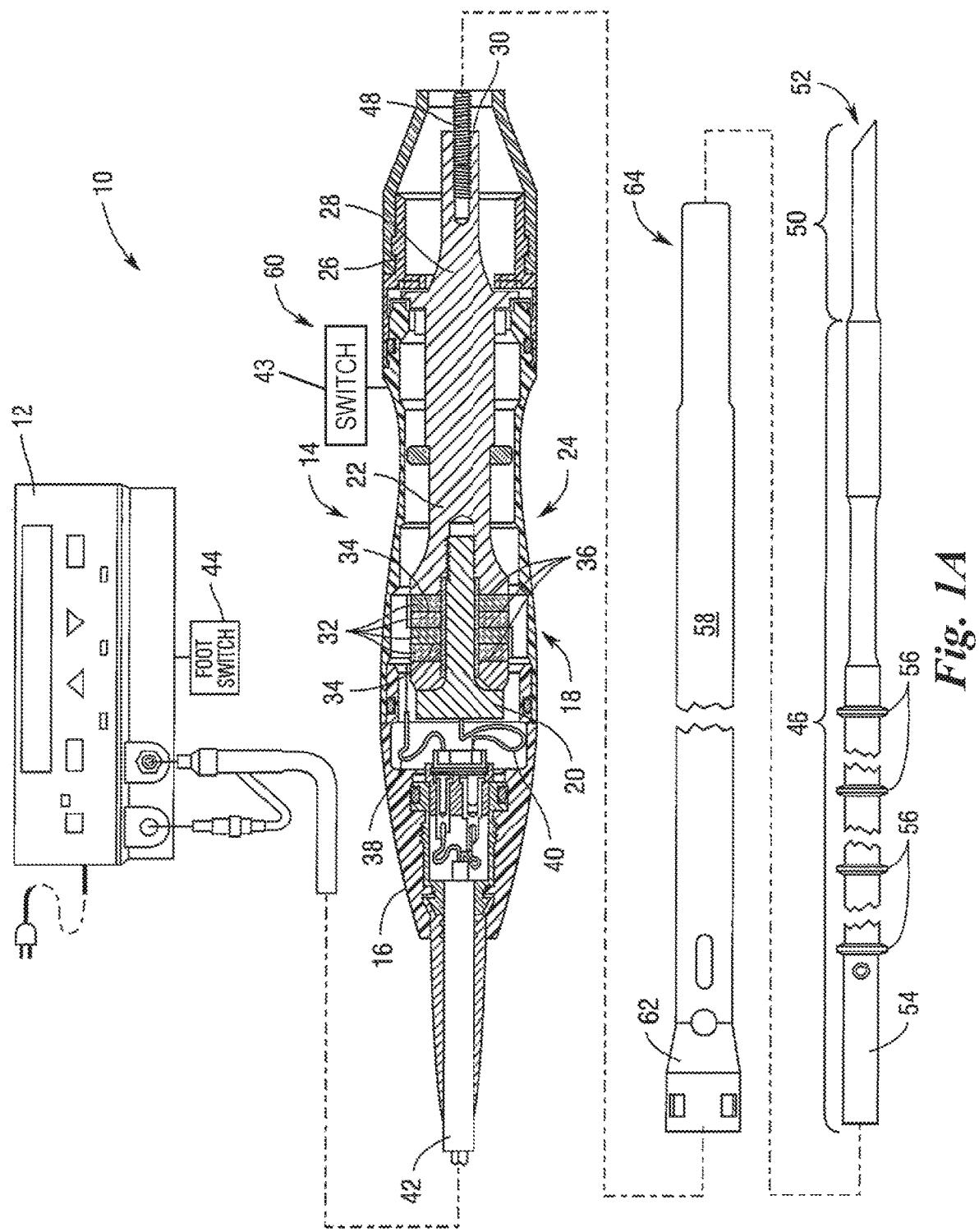
FIG. 1A illustrates an embodiment of an ultrasonic surgical instrument system depicting a handle comprising a switch.

In various embodiments, an ultrasonic surgical instrument can comprise a wave guide and/or end effector, a first transducer, and a second transducer, wherein the first and second transducers can be operably engaged with the wave guide and/or end effector as outlined above. In at least one embodiment, the first transducer and the second transducer can each be selectively actuatable. In at least one such embodiment, the surgical instrument can comprise a handle which can comprise one or more switches which can be configured to selectively actuate the first and second transducers positioned therein. Referring to FIG. 1A, a switch 43 is positioned on the hand piece assembly 60. For example, a switch can be moved from an off position to a first position in order to actuate the first transducer, to a second position to actuate the second transducer, and/or to a third position to actuate the first transducer and the second transducer. In certain other embodiments, a handle can comprise a first switch configured to selectively actuate the first transducer and, in addition, a second switch configured to selectively actuate the second transducer. In such embodiments, the surgeon can select the power to be supplied to the wave guide and/or end effector. In various alternative embodiments, a surgical instrument can comprise three or more transducers which can be selectively actuated.

In various embodiments, as outlined above, a transducer can comprise a fore-bell, an end-bell, and one or more piezoelectric elements compressed, or clamped, between the fore-bell and end-bell. Often, the fore-bell and/or end-bell can include a shaft configured to be positioned within apertures in the piezoelectric elements in order to align the piezoelectric elements with each other. Once the transducer has been assembled, in various embodiments, the wave guide and/or end effector can be operably mounted to the transducer. In various other embodiments described herein, an ultrasonic surgical instrument can comprise a wave guide, an end effector, and one or more piezoelectric elements which can be mounted directly to the wave guide and/or end effector. In at least one embodiment, referring to FIG. 33, a surgical instrument can comprise an end effector 1750 and an integral alignment post, or shaft, 1722, wherein piezoelectric elements having apertures therein can be aligned with post 1722 such that the piezoelectric elements can be slid along post 1722 until they abut shoulder 1746. In various embodiments, referring now to FIG. 34, an ultrasonic surgical instrument can comprise an end effector 1850, a wave guide 1846, and piezoelectric elements 1832, wherein elements 1832 can be slid along shaft 1822 until they are stacked against wave guide 1846. Thereafter, an end member, such as end member 1820, for example, can be engaged with alignment shaft 1822 and utilized to secure piezoelectric elements 1832 between end member 1820 and wave guide 1846. In at least one such embodiment, alignment shaft 1822 can comprise a threaded end and, in addition, end member 1820 can comprise a threaded aperture, wherein the threaded aperture can be configured to threadably receive the threaded end of alignment shaft 1822.

In various embodiments, as outlined above, a voltage potential may be applied to the piezoelectric elements of a transducer to contract and expand the piezoelectric elements and generate vibrations. As also outlined above, such a voltage potential may be cycled between two values, such as between minimum and maximum values, for example. In various embodiments, the piezoelectric elements can be poled such that the voltage potential can affect the piezoelectric elements. More particularly, the piezoelectric elements can undergo a poling process such that a net electric, or magnetic, dipole is stored within each piezoelectric element, wherein the voltage potential can interact with the magnetic dipole and cause the piezoelectric element to vibrate. During a poling process, electrodes can be applied to the opposite sides of a piezoelectric element such that a large electric field can be applied across the piezoelectric element in order to arrange the domains within the piezoelectric material and create a net magnetic dipole within the piezoelectric element. In at least one embodiment, the electrodes may be screen-printed onto the electrodes, wherein one or more stencils can be aligned with the sides of the piezoelectric element, and wherein a roller having conductive ink thereon can be rolled across the stencil such that the conductive ink is selectively applied to the piezoelectric element. In certain embodiments, a mesh material can be applied to the surface of the piezoelectric element, wherein the conductive ink can be pressed through the mesh, or woven, material which is not covered by a masking portion of the stencil.

In various embodiments, the electrodes utilized to pole the piezoelectric elements, as outlined above, may be ground off of, and/or otherwise removed from, the piezoelectric elements such that a second set of electrodes can be positioned intermediate the various piezoelectric elements of a transducer stack, wherein the second set of electrodes can generate the voltage potential used during the operation of the surgical instrument. In other various embodiments, a second set of electrodes can be applied to the piezoelectric elements utilizing a physical vapor deposition process (PVD), wherein certain conductive materials, such as metals, for example, can be evaporated in a low pressure environment such that the conductive materials can be deposited onto the piezoelectric elements. In certain embodiments, a stencil, or mask, can be placed over the surfaces of the piezoelectric elements such that the conductive materials can be selectively deposited on the piezoelectric elements.

In various embodiments, the electrodes utilized to pole the piezoelectric elements can also be utilized to apply voltage potentials to the piezoelectric elements during use. In at least one embodiment, the electrodes can be pad-printed onto the piezoelectric elements. In at least one such embodiment, a conductive ink can be placed, or poured, onto a printing plate, wherein the surface of the ink can become tacky after being exposed to air, for example. Thereafter, a transfer pad can be pressed onto the ink such that the tacky portion of the ink adheres to transfer pad, the transfer pad can be positioned over a piezoelectric element, and the transfer pad can be pressed onto the piezoelectric element such that the ink adheres to the piezoelectric element. In such embodiments, the printing plate can have various reliefs or contours which can define the areas of the printing plate which can store the conductive ink and, correspondingly, can define the respective areas on the piezoelectric element in which the conductive ink will be applied. In various embodiments, the conductive ink can comprise a fluid, silver, and/or carbon, for example.

Figure 35:
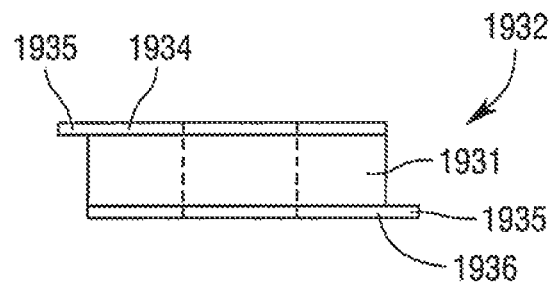
FIG. 35 illustrates an embodiment of a piezoelectric element and electrodes mounted thereto, wherein the electrodes comprise tabs extending therefrom.
Figure 36:
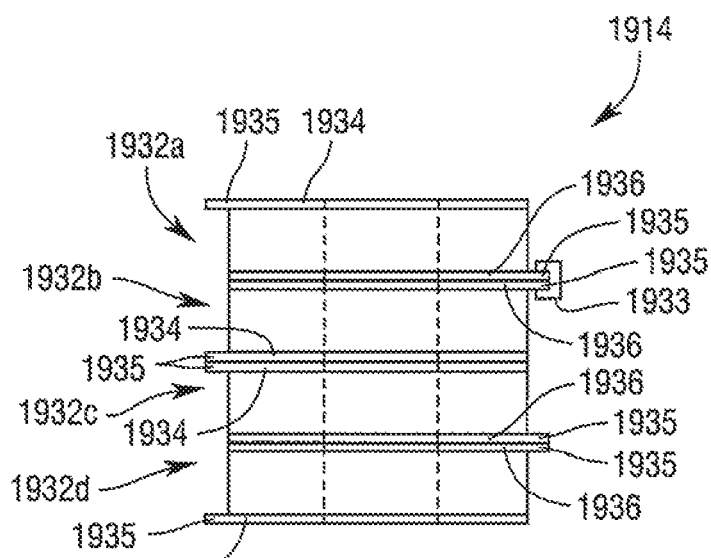
FIG. 36 illustrates a transducer stack comprising a plurality of the piezoelectric elements of FIG. 35.

In various embodiments, further to the above, one or more electrodes can be adhered to a piezoelectric element. In at least one embodiment, referring now to FIG. 35, a transducer can comprise one or more piezoelectric elements 1932, wherein each piezoelectric element 1932 can comprise a core, or disc, 1931, a positive electrode 1934, and a negative electrode 1936, for example. In at least one such embodiment, the positive electrode 1934 and/or the negative electrode 1936 can be adhered to the core 1931 utilizing a conductive adhesive. In use, as a result, a voltage source can be operably coupled to the positive electrode 1934 and negative electrode 1936 such that a voltage potential can be created between the positive and negative electrodes, as outlined above. When the piezoelectric elements 1932 are assembled into a transducer stack, such as transducer stack 1914 (FIG. 36), for example, the piezoelectric elements 1932 can be arranged such that their positive and/or negative electrodes are aligned with one another. For example, the negative electrode 1936 of piezoelectric element 1932a can be positioned against the negative electrode 1936 of piezoelectric element 1932b and, similarly, the positive electrode 1934 of piezoelectric element 1932b can be positioned against the positive electrode 1934 of piezoelectric element 1932c, for example. Owing to contact between adjacent negative electrodes 1936, and/or owing to contact between adjacent positive electrodes 1934, the polarization of one of the negative electrodes 1934, or positive electrodes 1936, may polarize an adjacent electrode.

In various embodiments, further to the above, each electrode can comprise a body, which is adhered to piezoelectric element core 1931, and a tab, or portion, 1935 which can be configured to extend outwardly from the electrode body and/or core 1931. In at least one such embodiment, the piezoelectric element core 1931 of a piezoelectric element can comprise an outer profile, wherein tabs, or portions, 1935 can extend outwardly with respect to the outer profile of core 1931. In certain embodiments, the tabs 1935 of adjacent piezoelectric elements 1932 can be connected to one another. In at least one such embodiment, conductive clips, connectors, and/or connecting electrodes, for example, can be utilized to couple the tabs 1935 of adjacent piezoelectric elements 1932 such that the adjacent negative electrodes 1936, or adjacent positive electrodes 1934, can be in electrical communication with one another and have the same, or an at least substantially similar, voltage potential. In at least one embodiment, a clip 1933 can connect adjacent tabs 1935, wherein, in at least one embodiment, clip 1933 can comprise a spring which can bias the clip from an open configuration into a closed configuration, for example. In certain embodiments, as described in greater detail further below, the cores 1931, for example, of various piezoelectric elements can comprise alignment features which can be configured to assure that adjacent piezoelectric elements can be assembled to each other in only one way, or a limited number of ways. In at least one such embodiment, the alignment features can be configured such that the tabs 1935 of the electrodes are aligned, or at least substantially aligned, with one another when the alignment features of piezoelectric elements are aligned, or at least substantially aligned, with one another.

Figure 37:
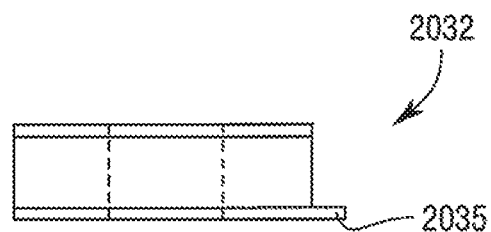
FIG. 37 illustrates an embodiment of a piezoelectric element and electrodes mounted thereto.
Figure 38:
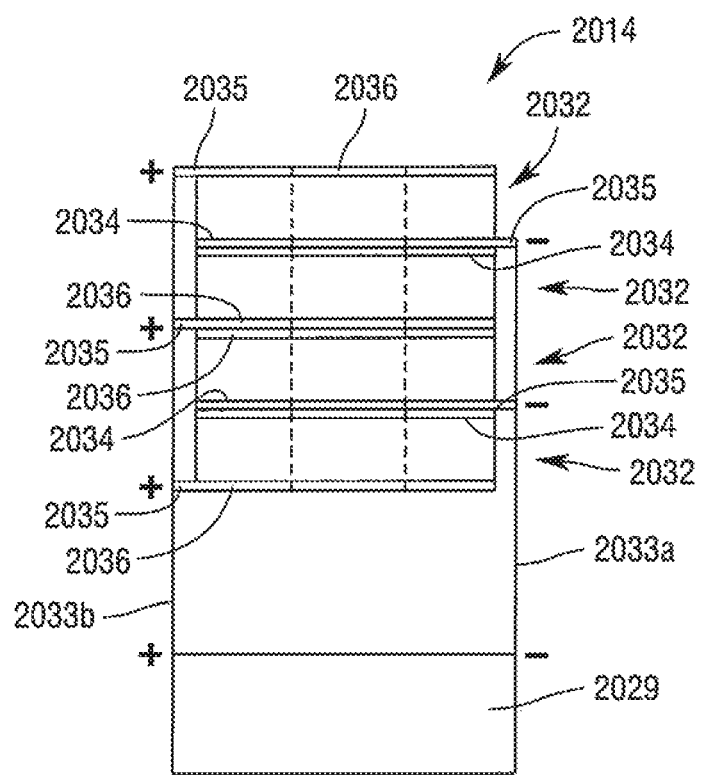
FIG. 38 illustrates a transducer stack comprising a plurality of the piezoelectric elements of FIG. 37.

In various embodiments, referring now to FIGS. 37 and 38, a transducer stack 2014 can comprise a plurality of piezoelectric elements, such as elements 2032, for example, wherein each element 2032 can comprise a negative electrode 2034 and a positive electrode 2036. In certain embodiments, the transducer stack 2014 can further comprise one or more first connecting electrodes 2033a which can operably connect a plurality of negative electrodes 2034 and, in addition, one or more second connecting electrodes 2033b which can operably connect a plurality of positive electrodes 2036. More particularly, in at least one embodiment, first connecting electrode 2033a can be connected to the tabs 2035 associated with negative electrodes 2034 in order to polarize each of the negative electrodes 2034 with the same, or at least substantially the same, voltage potential and, in addition, second connecting electrode 2033b can be connected to the tabs 2035 associated with the positive electrodes 2036 in order to polarize each of the positive electrodes 2036 with the same, or at least substantially the same, voltage potential. In various embodiments, the connecting electrodes can comprise a brass or copper strip or material, for example, wherein first connecting electrode 2033a can be welded or soldered to negative electrodes 2034 and, similarly, second connecting electrode 2033b can be welded or soldered to positive electrodes 2036. In some embodiments, the connecting electrodes can comprise insulated wires, and/or any other suitable conductor. In certain embodiments, although not illustrated, the connecting electrodes can comprise one or more clips or clamp elements which can be operably engaged with the tabs 2035, for example. In any event, further to the above, the first connecting electrode 2033a can be operably coupled with the negative terminal of a battery 2029, and/or any other suitable power source, and the second connecting electrode 2033b can be operably coupled with the positive terminal of the battery 2029, for example.

Figure 39:
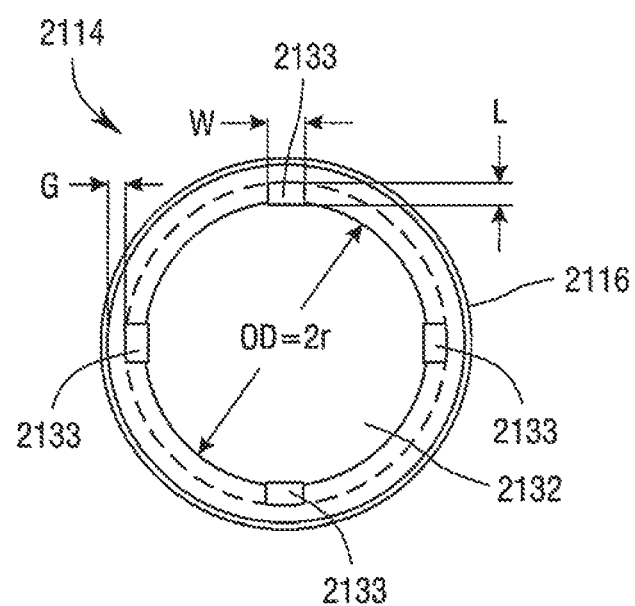
FIG. 39 illustrates an end view of a transducer stack comprising piezoelectric elements, electrodes positioned intermediate the piezoelectric elements, and connecting electrodes operably connecting the intermediate electrodes.

In various embodiments, referring to FIG. 39, the connecting electrodes 2133 of a transducer stack 2114 can be positioned radially outwardly with respect to the outside diameter (OD), or outer profile, of the piezoelectric elements 2132. In various circumstances, various radial gaps can exist between the outside diameter (OD), or outer profile, of the piezoelectric elements 2132 and the transducer housing 2116 in order to accommodate the connecting electrodes 2133. Such gaps, however, can represent lost power capacity of the piezoelectric elements. More particularly, as discussed above, piezoelectric elements having larger diameters, for example, have the capacity for producing larger quantities of work and, as the above-described gaps can represent a loss in the diameter, or size, of the piezoelectric elements, the gaps can reduce the power capacity of the piezoelectric elements. In certain circumstances, however, some amount of gap, G, between the piezoelectric elements 2132 and the transducer housing 2116 may be desired in order to accommodate the radial expansion, or Poisson's expansion, of the piezoelectric elements 2132, especially when the piezoelectric elements are subjected to longitudinal contraction.

Figure 40:
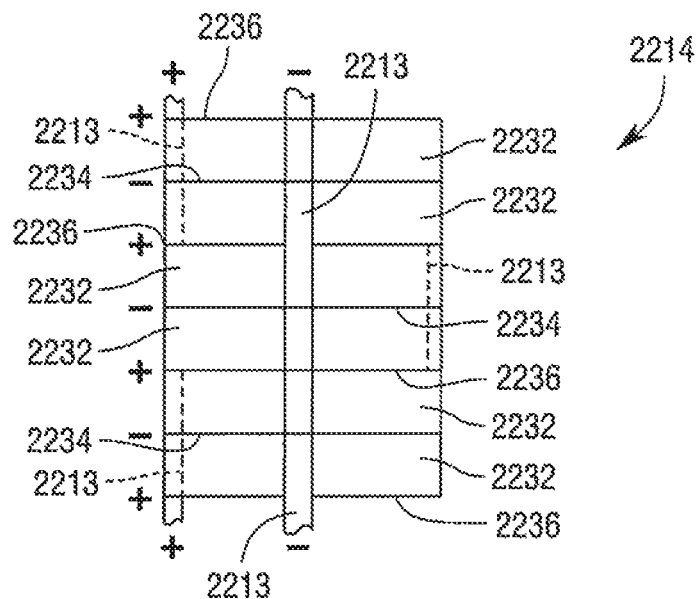
FIG. 40 illustrates a transducer stack comprising a plurality of piezoelectric elements having a plurality of notches therein and connecting electrodes extending through the notches.
Figure 41:
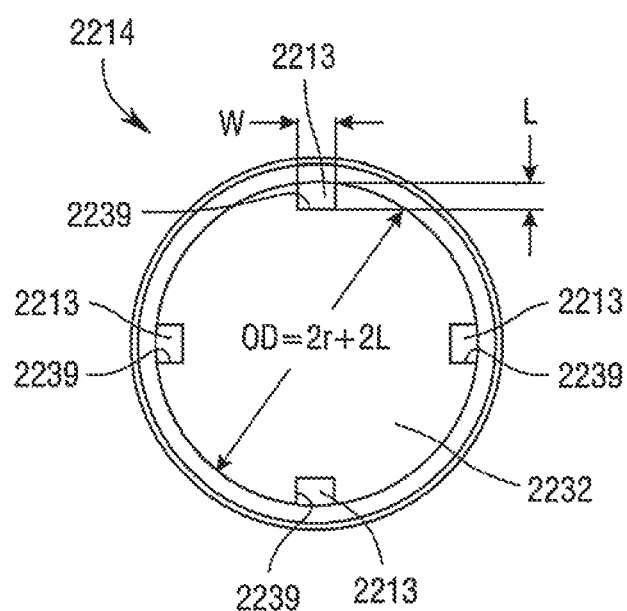
FIG. 41 illustrates an end view of the transducer stack of FIG. 40.

In various embodiments, now referring to FIGS. 40 and 41, a transducer stack 2214 can comprise a plurality of piezoelectric elements 2232, positive polarizing electrodes 2236 and/or negative polarizing electrodes 2234 positioned intermediate the piezoelectric elements 2232, and one or more connecting electrodes 2213 operably connecting the negative electrodes 2234 and/or operably connecting the positive electrodes 2236. In at least one embodiment, referring to FIG. 41, each piezoelectric element 2232 can comprise an outside diameter, or outer profile, and one or more grooves, notches, or slots, 2239 therein, wherein notches 2239 can be configured to have a connecting electrode 2213 positioned therein. More particularly, in at least one embodiment, each notch 2239 can be sized and configured to receive a connecting electrode 2213 such that there is a clearance fit between the connecting electrode 2213 and the sidewalls of the notches 2239, for example. In at least one such embodiment, each notch 2239 can have a width which is wider than the width "W" of a connecting electrode 2213 and a depth which is deeper than the height "L" of a connecting electrode 2213, for example. In at least one embodiment, the width W can be approximately 2 mm and the height L can be approximately 0.6 mm. In various embodiments, connecting electrodes 2213 and notches 2239 can be configured such that the connecting electrodes 2213 do not extend above, or outwardly with respect to, the outer profile of the piezoelectric elements 2232. In any event, owing to notches 2239, referring to FIG. 41, the largest outer diameter (OD=2r+2L), or outer profile, of the piezoelectric elements 2232 can be larger than the largest outer diameter (OD=2r), or outer profile, of the piezoelectric elements 2132 and, as a result, piezoelectric elements 2232 may be capable of generating more power than piezoelectric elements 2132, for example. In certain embodiments, the diameter of piezoelectric elements 2232 (OD=2r+2L) can have a diameter of approximately 8 mm, approximately 10 mm, approximately 12 mm, approximately 14 mm, and/or approximately 16 mm, for example, wherein, in certain embodiments, such piezoelectric elements can provide a power increase between approximately 13% and approximately 53%, for example, as compared to piezoelectric elements 2132.

In various embodiments, further to the above, the connecting electrodes 2213 of transducer stack 2214, for example, can operably connect one or more negative polarizing electrodes 2234 and/or one or more positive polarizing electrodes 2236 with a power source. For example, referring again to FIG. 40, a connecting electrode 2213 can connect a first positive electrode 2236 and a second positive electrode 2236 with the positive terminal of a battery, for example, wherein the connecting electrode 2213 can comprise a bridge which spans, and is not operably engaged with, a negative electrode 2234 positioned intermediate the first and second positive electrodes 2236. On the other side of the transducer stack, for example, another connecting electrode 2213 can operably connect the second positive electrode 2236 with a third positive electrode 2236, wherein, similar to the above, the connecting electrode 2213 can comprise a bridge which spans, and is not operably engaged with, another negative electrode 2234 positioned intermediate the second and third positive electrodes 2236. In various embodiments, such a pattern can be repeated in order to operably connect all of the positive electrodes 2236 within transducer stack 2214 with one another and the positive terminal of a power source. As can be seen in FIG. 41, the piezoelectric elements 2232 can comprise notches 2239 on the opposite sides thereof in order to accommodate the arrangement of connecting electrodes described above, although other arrangements are possible. Similar to the above, a connecting electrode can be configured to connect a first negative electrode 2234 and a second negative electrode 2234 with the negative terminal of a battery, for example, wherein the connecting electrode 2213 can comprise a bridge which spans, and is not operably engaged with, a positive electrode 2236 positioned intermediate the first and second negative electrodes 2234. On the other side of the transducer stack, for example, another connecting electrode 2213 can operably connect the second negative electrode 2234 with a third negative electrode 2234, wherein, similar to the above, the connecting electrode 2213 can comprise a bridge which spans, and is not operably engaged with, another positive electrode 2236 positioned intermediate the second and third negative electrodes 2234.

Figure 42:
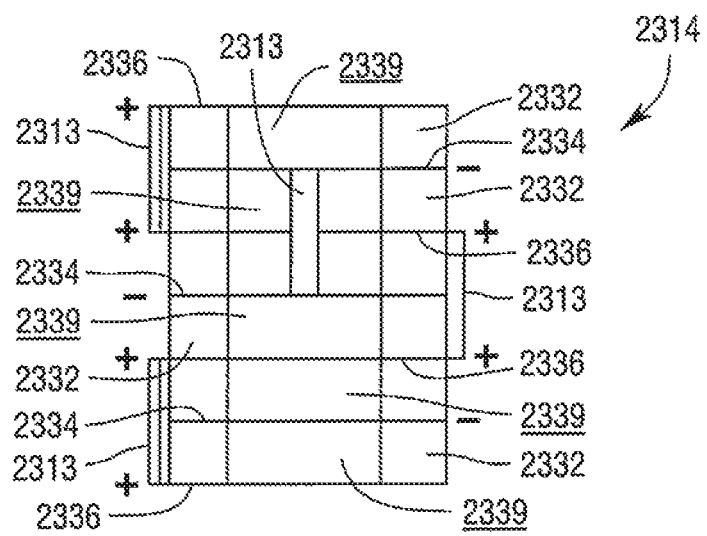
FIG. 42 illustrates a transducer stack comprising a plurality of piezoelectric elements having a plurality of flat surfaces and a plurality of connecting electrodes.
Figure 43:
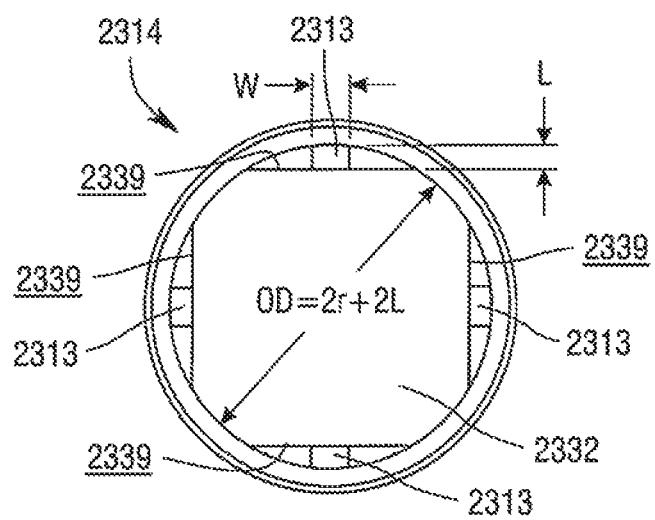
FIG. 43 illustrates an end view of the transducer stack of FIG. 42.

In various embodiments, referring now to FIGS. 42 and 43, a transducer stack 2314 can comprise a plurality of piezoelectric elements 2332, positive electrodes 2336 and/or negative electrodes 2334 positioned intermediate the piezoelectric elements 2332, and one or more connecting electrodes 2313 operably connecting the negative electrodes 2334 and/or operably connecting the positive electrodes 2336. In at least one embodiment, piezoelectric elements 2332 can comprise one or more flat surfaces 2339 which can be configured to accommodate connecting electrodes 2313 yet permit the average diameter of the piezoelectric elements 2332 to be increased as compared to the average diameters of piezoelectric elements 2132. More particularly, referring to FIG. 43, the diameters of various circular portions of each piezoelectric element 2332, i.e., the portions intermediate flats 2339, can be increased such that the outer diameter of the piezoelectric element (OD=2r+2L) is the same distance, or at least substantially the same distance, as a diameter defined by connecting electrodes 2313. In at least one such embodiment, such intermediate portions can add to the overall size, or area, of each piezoelectric element 2332 and, thus, add to the quantity of work that the piezoelectric elements can produce. In certain embodiments, similar to the above, various portions of piezoelectric elements 2332 can have a diameter of approximately 8 mm, approximately 10 mm, approximately 12 mm, approximately 14 mm, and/or approximately 16 mm, for example, wherein, in certain embodiments, such piezoelectric elements can provide a power increase between approximately 11% and approximately 42%, for example, as compared to piezoelectric elements 2132. In various embodiments, flats 2339 can be machined into the piezoelectric element, for example.

Figure 44:
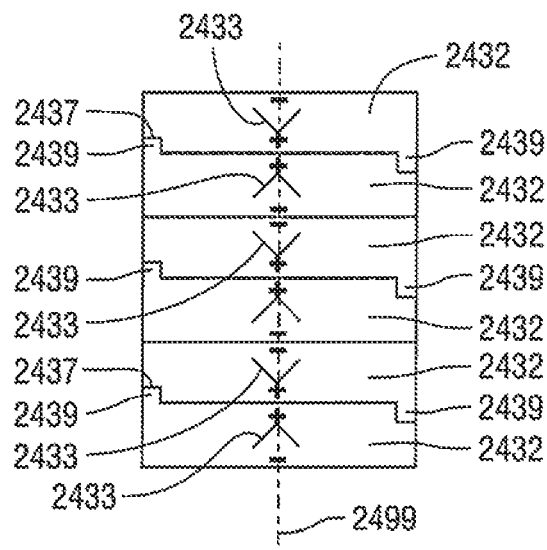
FIG. 44 illustrates a transducer stack comprising a plurality of piezoelectric elements having a plurality of indexing features configured to assure the proper alignment of the piezoelectric elements.
Figure 45:
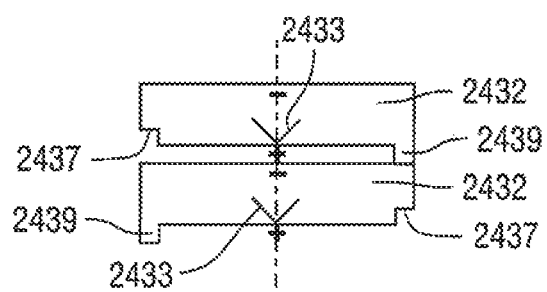
FIG. 45 is a schematic illustrating how the indexing features of the piezoelectric elements of FIG. 44 can prevent misalignment between the piezoelectric elements.

In various embodiments, as outlined above, the piezoelectric elements of a transducer can undergo a poling process such that a net dipole can be established within the piezoelectric element. In at least one embodiment, such a net dipole can comprise a positive charge (+), a negative charge (−), and a net dipole moment vector defined between the negative charge and the positive charge. In certain embodiments, referring now to FIGS. 44 and 45, the positive charge (+) of a piezoelectric element, such as piezoelectric elements 2432, for example, can be positioned on one side of the piezoelectric element while the negative charge (−) can be positioned on the opposite side of the piezoelectric element. In at least one such embodiment, each piezoelectric element 2432 can comprise one or more indicia which can indicate the direction of the net dipole moment vector. For example, piezoelectric elements 2432 can comprise an arrow 2433 formed on the side thereof, wherein the arrow 2433 can point in a direction toward the positive charge and away from the negative charge. In at least one embodiment, arrow 2433 can be ground, pressed, and/or etched, for example, into the side of the piezoelectric element while, in other embodiments, arrow 2433 can be integrally formed with the piezoelectric element when the piezoelectric element is manufactured, for example. In various embodiments, the arrow 2433 can extend from and/or be recessed within the side of the piezoelectric element. In certain embodiments, the arrows 2433 can be painted and/or otherwise suitably applied to the piezoelectric elements. In any event, piezoelectric elements having at least one indicium can allow a person assembling a transducer to readily recognize the polarity of the piezoelectric elements and, as a result, quickly and reliably, arrange the piezoelectric elements such that their poles are properly aligned with one another. In various embodiments, the indicia of a first piezoelectric element can be aligned with the indicia of a second piezoelectric element in order to align the dipole moment vector of the first element with the dipole moment vector of the second element.

Figure 46:
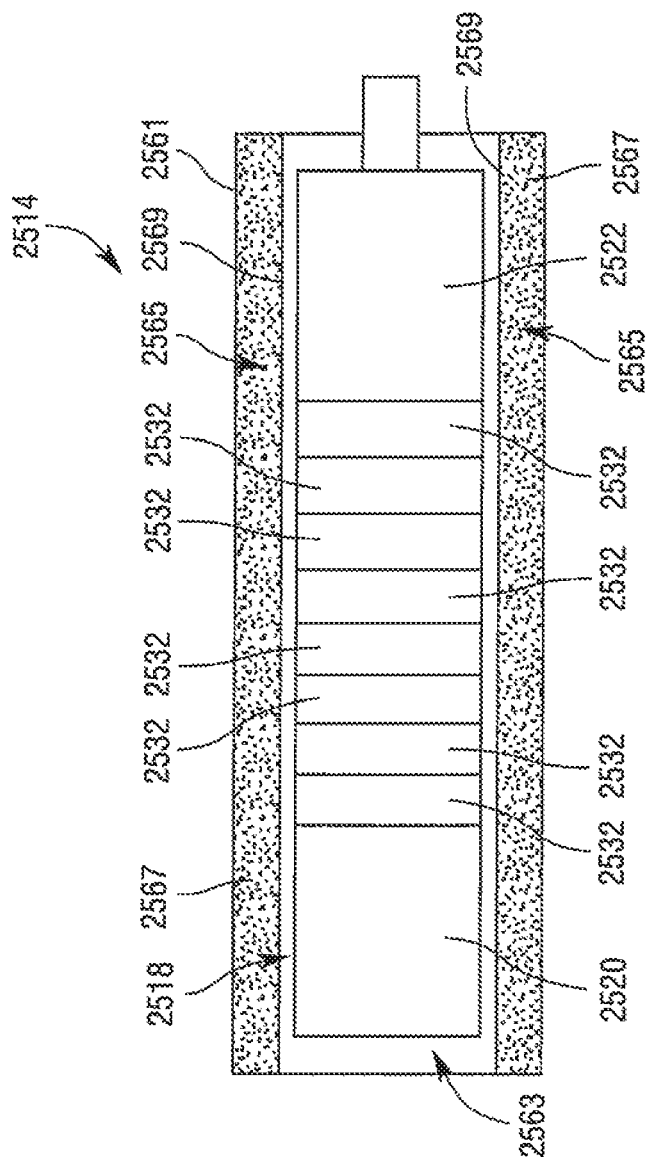
FIG. 46 illustrates an embodiment of a transducer stack and an enclosure surrounding the transducer stack.

In addition to or in lieu of the above, piezoelectric elements can comprise one or more indexing features which can be configured to assure that adjacent piezoelectric elements are properly aligned with one another. For example, referring again to FIGS. 44 and 45, piezoelectric elements 2432 can comprise one or more recesses, or grooves, 2437 and one or more projections 2439, wherein projections 2439 can be configured to be seated within recesses 2437 when piezoelectric elements 2432 are properly aligned with one another. More particularly, in at least one embodiment, projections 2439 can be seated within recesses 2437 only when piezoelectric elements are aligned along a common axis 2499 and the polarity of the piezoelectric elements 2432 are aligned such the positive charge (+) on one side of an element is aligned with the positive charge of an adjacent element and/or the negative charge (−) on the other side of the element is aligned with the negative charge of adjacent element. Absent a suitable alignment between the indexing features, referring to FIG. 45, the piezoelectric elements 2432 may not be properly seated with one another and a person, or machine, assembling a transducer may be able to quickly detect the misalignment. In various embodiments, various piezoelectric elements, such as elements 2432, for example, can be configured such they can be assembled in pairs and such that the outwardly-facing surfaces of the piezoelectric elements are flat and parallel with one another, or at least substantially flat and substantially parallel with one another, wherein, referring again to FIG. 44, the negative charges of the elements can be adjacent to the flat surfaces, and wherein various mated pairs of the piezoelectric elements can be stacked on top of one another with the flat surfaces and negative charges aligned with each other. In at least one such embodiment, the net dipole moment vectors of the piezoelectric elements can be perpendicular, or at least substantially perpendicular, with respect to the outwardly-facing flat surfaces of the piezoelectric elements In various circumstances, as outlined above, the piezoelectric elements of a transducer may, for whatever reason, lose their ability, or at least a portion of their ability, to generate sufficient vibrations to vibrate the end effector of an ultrasonic surgical instrument. Once a transducer has exceeded its useful life, the transducer is often disposed of. In various circumstances, the piezoelectric elements of such transducers, for example, may be at least partially comprised of lead and/or other certain materials. In various embodiments described herein, a transducer, and/or surgical instrument, may comprise means in which to encapsulate or contain the piezoelectric elements of the transducer when it is desired to dispose of the transducer. In various embodiments, referring now to FIG. 46, a transducer assembly, such as transducer assembly 2514, for example, can comprise a transducer stack 2518 comprising an end-bell 2520, a fore-bell 2522, one or more piezoelectric elements 2532 positioned intermediate end-bell 2520 and fore-bell 2522, for example, and an enclosure which is configured to at least partially enclose the transducer stack 2518. In at least one embodiment, the enclosure may surround the entire piezoelectric element stack 2518 such that only a portion of the fore-bell 2522 extends through the enclosure in order to allow a wave guide and/or end effector to be operably engaged with the transducer stack 2518.

Figure 47:
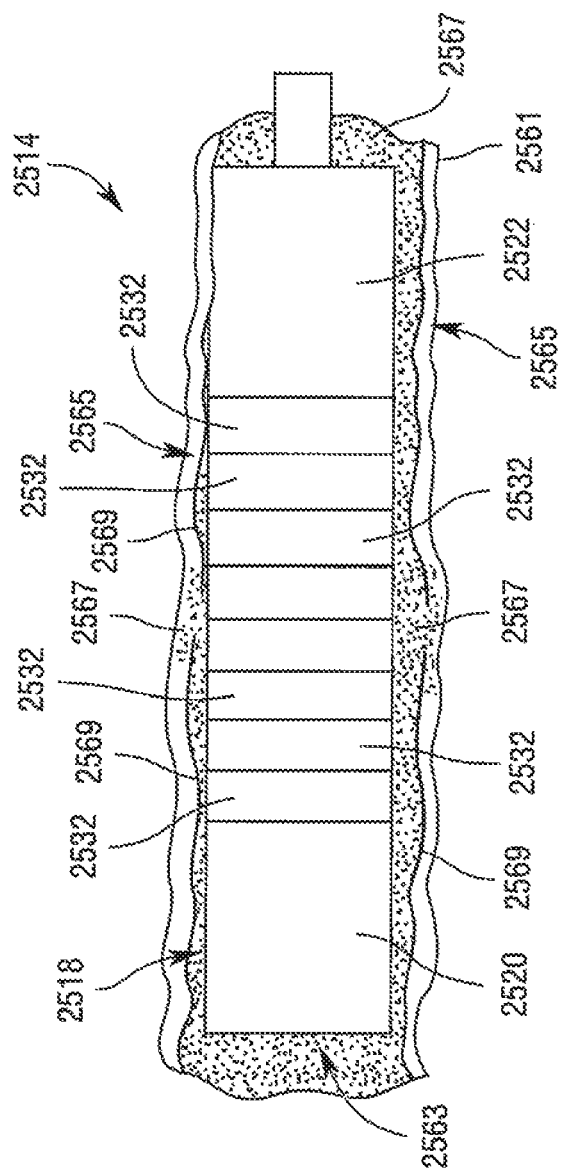
FIG. 47 illustrates the enclosure of FIG. 46 in a ruptured condition and a material at least partially surrounding the transducer stack.

In various embodiments, further to the above, transducer assembly 2514 can comprise an enclosure 2561 which can have a first compartment 2563 and a second compartment 2565, wherein the transducer stack 2518 can be positioned within the first compartment 2563 and a material 2567 can be positioned within the second compartment 2565. Before disposing of the transducer assembly 2514, in at least one embodiment, the second compartment 2565 can be ruptured such that the material 2567 can flow from the first compartment 2563 into the second compartment 2565 and at least partially surround transducer stack 2518, as illustrated in FIG. 47. In at least one such embodiment, referring to FIG. 46, a sidewall 2569 can be configured to separate the first compartment 2563 and the second compartment 2565, wherein the sidewall 2569 can be configured to rupture in at least one location. In various embodiments, sidewall 2569, for example, can comprise one or more score marks, or weak points, for example, which can determine the locations in which the sidewall 2569 may be most likely to rupture. In certain embodiments, the enclosure 2561 can be configured such that a person can use their hand to squeeze the enclosure 2561 and burst the sidewall 2569 separating first compartment 2563 and second compartment 1265. In various embodiments, the enclosure 2561 can be configured such the material 2567 cannot thereafter escape, or at least substantially escape, from enclosure 2561. In at least one such embodiment, the enclosure 2561 can be sealed, or at least substantially sealed, to fore-bell 2522, for example, such that the material 2567 cannot flow, or at least substantially flow, between enclosure 2561 and the portion of fore-bell 2522 which extends out of enclosure 2561.

Figure 48:
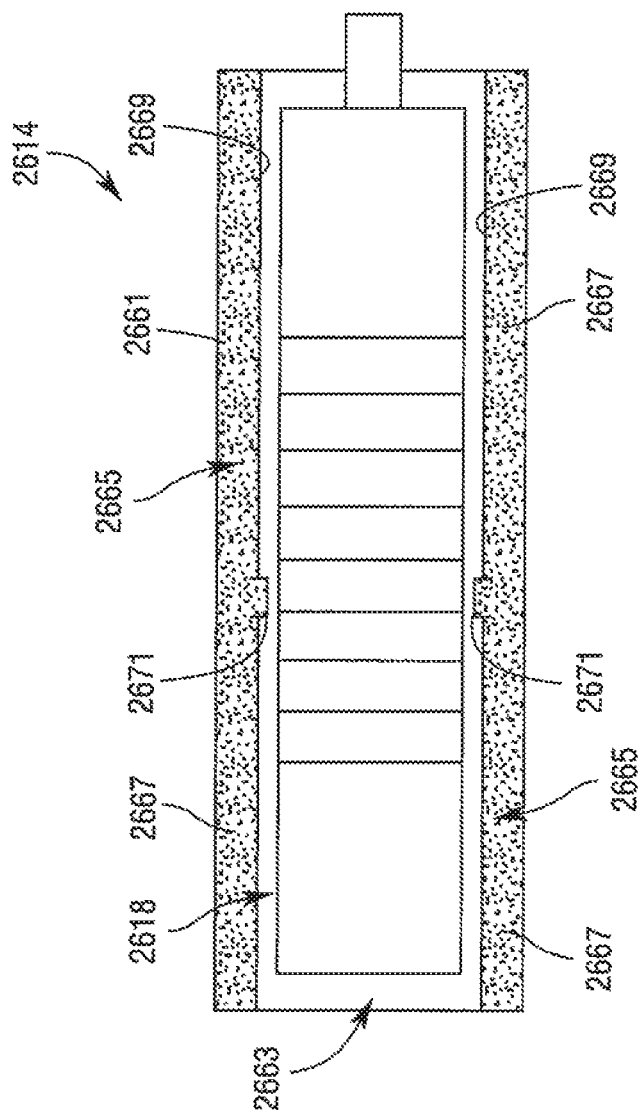
FIG. 48 illustrates a second embodiment of a transducer stack and an enclosure surrounding the transducer stack.

In various embodiments, referring now to FIG. 48, a transducer assembly 2614 can comprise an enclosure 2661 comprising at least one valve which can be opened to place a first compartment 2665 in fluid communication with a second compartment 2663. More particularly, in at least one embodiment, the enclosure 2661 can comprise a sidewall 2669 and one or more valves 2671, for example, which can be selectively opened to permit material 2667 to flow from first compartment 2665 into second compartment 2663. In at least one such embodiment, especially in embodiments where material 2667 is a fluid, valves 2671 can be configured to pop open when subjected to sufficient fluid pressure generated within material 2667 when the enclosure 2661 is compressed. In various embodiments, material 2667 can be fluidic when it is positioned within the first compartment 2665 and when it initially surrounds transducer stack 2618. In certain embodiments, however, the material 2667 can be configured to harden after it has entered into first compartment 2665. In at least one such embodiment, first compartment 2665 can be air-tight and, when the material 2667 enters into the second compartment 2663, the material 2667 can be exposed to air, for example, which can cause it harden. In any event, whether or not the material remains fluidic or hardens, the material can encapsulate, or at least partially encapsulate, certain materials within the transducer stack to further reduce the possibility of such materials from escaping from the enclosure.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Sterilization can also be done by any number of ways known to those skilled in the art including beta or gamma radiation, ethylene oxide, and/or steam.

In various embodiments, an ultrasonic surgical instrument can be supplied to a surgeon with a wave guide and/or end effector already operably coupled with a transducer of the surgical instrument. In at least one such embodiment, the surgeon, or other clinician, can remove the ultrasonic surgical instrument from a sterilized package, plug the ultrasonic instrument into a generator, as outlined above, and use the ultrasonic instrument during a surgical procedure. Such a system can obviate the need for a surgeon, or other clinician, to assemble a wave guide and/or end effector to the ultrasonic surgical instrument. After the ultrasonic surgical instrument has been used, the surgeon, or other clinician, can place the ultrasonic instrument into a sealable package, wherein the package can be transported to a sterilization facility. At the sterilization facility, the ultrasonic instrument can be disinfected, wherein any expended parts can be discarded and replaced while any reusable parts can be sterilized and used once again. Thereafter, the ultrasonic instrument can be reassembled, tested, placed into a sterile package, and/or sterilized after being placed into a package. Once sterilized, the reprocessed ultrasonic surgical instrument can be used once again.

Although various embodiments have been described herein, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An ultrasonic surgical instrument, comprising:
   a housing;
   an end effector comprising an ultrasonic blade;
   a waveguide extending to the ultrasonic blade; and
   a vibration generating system, comprising:
     a transducer attachable to the housing, wherein the transducer comprises piezoelectric elements, and wherein the piezoelectric elements vibrate at a magnitude proportional to at least one electrical input; and
     a switch positioned on the housing, wherein the vibration generating system is selectively operable from the switch in a plurality of energizing operating states and a non-energizing operating state, wherein the plurality of energizing operating states comprises:
       a first operating state in which the transducer vibrates at a first vibration magnitude; and
       a second operating state in which the transducer vibrates at a second vibration magnitude, wherein the first vibration magnitude is different than the second vibration magnitude, and wherein the switch is configured to select the first operating state, the second operating state, or the non-energizing operating state.

2. The ultrasonic surgical instrument of claim 1, wherein the housing defines a handle, and wherein the handle is configured to receive a battery therein.

3. The ultrasonic surgical instrument of claim 1, wherein the at least one electrical input comprises a voltage.

4. The ultrasonic surgical instrument of claim 1, wherein the at least one electrical input comprises a current.

5. The ultrasonic surgical instrument of claim 1, wherein the ultrasonic blade comprises a curved body.

6. The ultrasonic surgical instrument of claim 1, wherein the first vibration magnitude is less than the second vibration magnitude.

7. The ultrasonic surgical instrument of claim 1, wherein the switch is movable between an off position, a first position, and a second position.

8. The ultrasonic surgical instrument of claim 7, wherein the first position corresponds to the first operating state, and wherein the second position corresponds to the second operating state.

9. The ultrasonic surgical instrument of claim 1, wherein the transducer is removably attachable to the housing.

10. An ultrasonic surgical instrument, comprising:
    a housing comprising a switch;
    an end effector comprising a curved ultrasonic blade;
    a transducer attachable to the housing, wherein the transducer comprises piezoelectric elements, and wherein the piezoelectric elements vibrate at a magnitude proportional to at least one electrical input;
    a waveguide extending from the transducer to the curved ultrasonic blade; and
    a vibration generating system selectively operable by the switch in a plurality of energizing operating states and a non-energizing operating state, wherein the plurality of energizing operating states comprises:
      a first operating state, wherein the transducer vibrates at a first vibration magnitude in the first operating state; and
      a second operating state, wherein the transducer vibrates at a second vibration magnitude in the second operating state, wherein the first vibration magnitude is different than the second vibration magnitude, and wherein the switch is configured to select the first operating state, the second operating state, or the non-energizing operating state.

11. The ultrasonic surgical instrument of claim 10, wherein the at least one electrical input comprises a voltage.

12. The ultrasonic surgical instrument of claim 10, wherein the at least one electrical input comprises a current.

13. The ultrasonic surgical instrument of claim 10, wherein the first vibration magnitude is less than the second vibration magnitude.

14. The ultrasonic surgical instrument of claim 10, wherein the switch is movable between an off position, a first position, and a second position.

15. The ultrasonic surgical instrument of claim 14, wherein the first position corresponds to the first operating state, wherein the second position corresponds to the second operating state, and wherein the off position corresponds to the non-energizing operating state.

16. An ultrasonic surgical instrument, comprising:
    a housing;
    an end effector comprising an ultrasonic blade;
    a waveguide extending to the ultrasonic blade; and
    an ultrasonic energy delivery system, comprising:
      a transducer attachable to the housing, wherein the transducer comprises piezoelectric elements, and wherein the piezoelectric elements vibrate at a magnitude proportional to at least one electrical input; and
      a switch, wherein the switch is configured to selectively operate the ultrasonic energy delivery system in a plurality of energizing operating states and a non-energizing operating state, wherein the plurality of energizing operating states comprises:
        a first operating state in which the transducer vibrates at a first vibration magnitude; and
        a second operating state in which the transducer vibrates at a second vibration magnitude, wherein the first vibration magnitude is different than the second vibration magnitude, and wherein the switch is configured to selectively switch the ultrasonic energy delivery system between the first operating state, the second operating state, and the non-energizing operating state.

17. The ultrasonic surgical instrument of claim 16, wherein the at least one electrical input comprises a voltage.

18. The ultrasonic surgical instrument of claim 16, wherein the ultrasonic blade comprises a body, and wherein the body comprises:
   a proximal end;
   a distal end; and
   a longitudinal axis defined between the proximal end and the distal end, wherein the longitudinal axis defines at least one curve.

* * * * *